United States Patent [19]
Bauer et al.

[11] Patent Number: 5,182,205
[45] Date of Patent: Jan. 26, 1993

[54] NUCLEOTIDE SEQUENCES WHICH ARE SELECTIVELY EXPRESSED IN PRE-B CELLS AND PROBES THEREFOR

[75] Inventors: Steven R. Bauer, Birsfelden; Akira Kudo, Basel, both of Switzerland; Georg F. Melchers, Grenzach, Fed. Rep. of Germany; Nobuo Sakaguchi, Saga, Japan

[73] Assignee: Hoffmann-La Roche Inc., Nutley, N.J.

[21] Appl. No.: 701,328

[22] Filed: May 8, 1991

Related U.S. Application Data

[63] Continuation of Ser. No. 119,369, Nov. 10, 1987, abandoned.

[30] Foreign Application Priority Data

Nov. 27, 1986 [GB] United Kingdom ................ 8628433
Jul. 14, 1987 [GB] United Kingdom ................ 8716497
Oct. 14, 1987 [GB] United Kingdom ................ 8724100

[51] Int. Cl.$^5$ ..................... C12N 5/10; C12N 15/85; C12N 15/12; C12N 1/21
[52] U.S. Cl. ..................... 435/240.2; 435/172.3; 435/252.3; 435/252.33; 435/320.1; 536/24.31; 536/23.5
[58] Field of Search ................ 435/69.1, 172.3, 320.1, 435/252.3, 252.33, 240.2; 536/27

[56] References Cited

PUBLICATIONS

Wu et al., PNAS pp. 993–997, vol. 87, 1990.
Yancopoulos et al. PNAS pp. 5759–5763, vol. 87, 1990.
Rolink et al. EMBOJ. pp. 327–336, vol. 10, 1991.
Clark et al. Science vol. 236, pp. 1225–1237, 1987.
Cooper et al. Nature 321:616 (1986) Abstract.
Hedrich et al. (1984) Nature 308:149–153.
Davis et al. (1984) PNAS 81:2194–2198.
Torelli et al. Differentiation 27(2) 133–40 1984.
Soma et al., BBRC 132:100–9 (1985).
Chou et al., UCLA Symp Mol Cell Biol, 19(Mol Biol Dev) 459–80 (1984).
Yancoupoulos, et al., Nature 311:727–733 (Oct. 25, 1984).
Sakaguchi, et al., EMBO Journal 5:2139–2147 (Sep. 1986).
Sakaguchi and Melchers, Nature 324:579–582 (Dec. 11, 1986).
Sakaguchi, et al., Current Topics in Microbiology and Immunology 135:139–148 (1987).
Kudo, et al., EMBO Journal 6:103–107 (Jan. 1987).
Kudo and Melchers, EMBO Journal 6:2267–2272 (Aug. 1987).
Alt et al., Cell 27:381 (1981).
Alt et al., EMBO J. 3:1209 (1984).
Burrows et al., Nature 306:243 (1983).
Coffman et al., Nature 289:681 (1981).
Coffman et al., J. Mol. Cell. Immunol. 1:31 (1983).
Hieter et al., Nature 290:368 (1981).
Kincade et al., J. Immunol. 127:2262 (1981).
Lewis et al., Cell 30:807 (1982).
Maki et al., Science 209:1366 (1980).
McKearn et al., J. Immunol. 132:332 (1984).
Paige et al., J. Immunol. 121:641 (1978).
Perry et al., Cell 18:1333 (1979).
Perry et al., Proc. Natl. Acad. Sci. USA 78:247 (1981).
Reth et al., Nature 317:353 (1985).
Rosenberg et al., Proc. Natl. Acad. Sci. USA 72:1932 (1975).
Sakaguchi et al., J. Immunol. 125:2654 (1980).
Sakaguchi et al., EMBO J. 5:2139 (1986).
Sklar et al., European Patent Application Publication No. 149 547.
Sugiyama et al., Nature 303:812 (1983).
Tonegawa, Nature 302:575 (1983).

*Primary Examiner*—Richard A. Schwartz
*Assistant Examiner*—John LeGuyader
*Attorney, Agent, or Firm*—George M. Gould; William H. Epstein; Catherine R. Roseman

[57] ABSTRACT

The present invention provides nucleotide sequences which are selectively expressed in pre-B cells, probes comprising a polynucleotide hybridizing specifically to such a nucleotide sequence and methods for the production of such probes. These probes may be used for identifying pre-B cells. The invention further provides polypeptides translated from a transcript comprising a nucleotide sequence which is selectively expressed in pre-B cells or parts thereof, antibodies against these polypeptides and methods for the preparation and use of the polypeptides and antibodies raised against them.

15 Claims, 35 Drawing Sheets

FIG. 6
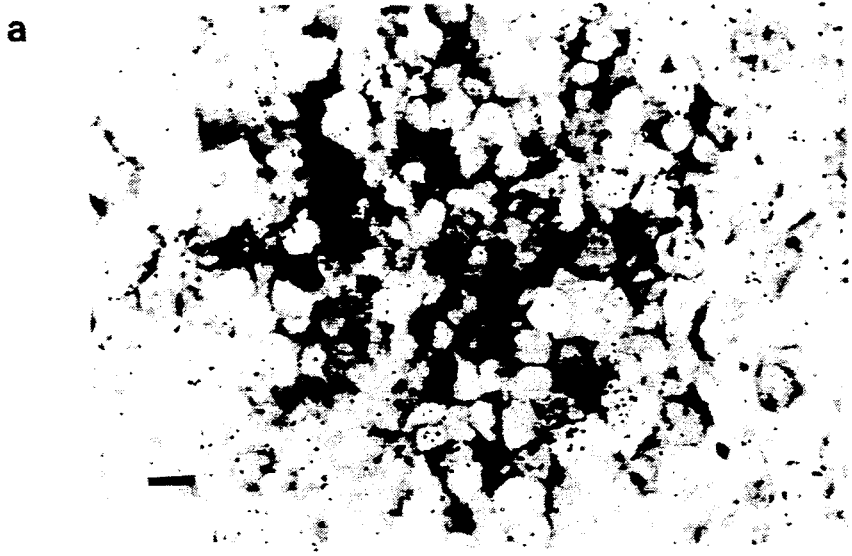
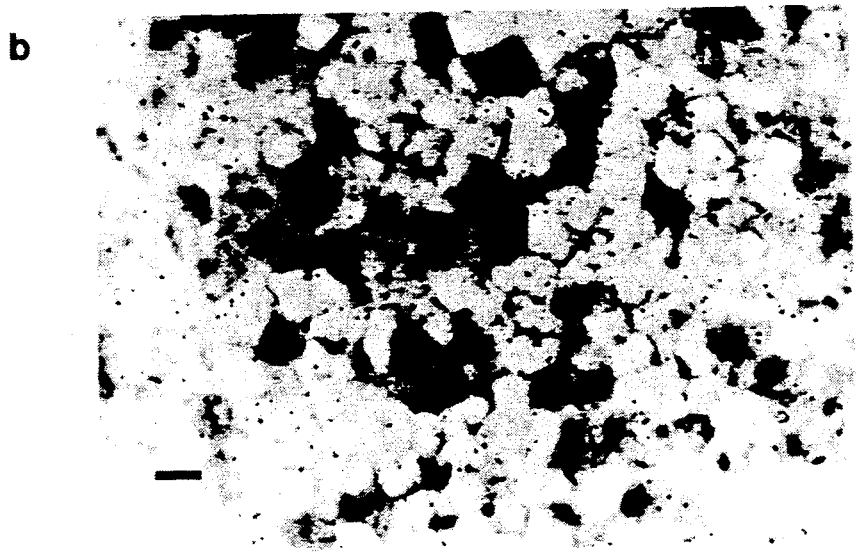

Fig. 8

```
      10        20        30        40        50        60        70        80        90       100
TTGGGTCTAGTGGATGGTGTCCACCACATACTTTCCCCAAGCTCACGCGAAAGGACGAGAGCTGTGGGCCCTGAGCTTCAGTGGGAACAACAGGCCTA 110       120       130       140       150       160       170       180       190       200
GCTATGGCCCTTCCCGGCAGCTCCTGTTCCAGATCATCCCACGGGGAGCAGGTCCCAGGTGCTCGTTTATAGGCTTCCATCTAAGCCCCAGTTTTGGTA 210       220       230       240       250       260       270       280       290       300
TGTCTTTGGTGGTGGGACCCAGCTCACAATCCTAGGTCAGCCCAAGTCTGACCCCTGGTCCTGCCTTCCTTAAAGAATCTTCAGCCAACA 310       320       330       340       350       360       370       380       390       400
AGGCCACAGCTAGTGTGTTGGTGAGCGAATTCTACCCTGTACTTTGGTGGTGGACTGGAAGGTAGATGGGGTCCCTGTCACTCAGGGTGTAGAGACAA 410       420       430       440       450       460       470       480       490       500
CCCACCCTCCAAACAGACCAACAACAACAAATACATGGTCAGCAGCTACCTGACACTGATATCTGACACTGATATCTGACCAGTGGATGCCTCACAGTAGATACAGCTGCCGGGT 510       520       530       540       550       560       570       580       590       600
CACTCATGAAGGAAACACTGTGGAGAAGAGTGTGTCACCTGCTGAGTGTTCTTAGACCACAATCCTCCCTGAAGCCTCAGGGGCCTGGATCTGAAGTGCC 610       620       630       640       650       660       670       680       690       700
AGAAAAGTTGTTTTTGTTTTTGTTTTTTGTTTTTTTTCCCATTAACCATCTCACTGTCTTTCCTGTGCCTAATACTCAATAAATATCTTACCACCAACCA (24)
```

Fig. 9

F I G. 10

Fig. 14

```
         10         20         30         40         50         60         70         80         90        100        110        120
CTGCAGAGAC TCTTGTTCCA TGGGCAGGT GTTCAGTTGC TCTCTACGGC CCCTCTAAGC CCTGGGGACC TGCTCCACAG ACCCAGGGGC CCTCAGGGAC TGGATATCAG TCAGGCAGAG 130        140        150        160        170        180        190        200        210        220        230        240
CTGCCCAGAG CTCTAGGGAT GGGTTAAGAC AGGCAGCTGT GAGTGAAAAC AGTTAGGCTT GCATCCCAAC CACAACCGGG TAGTCCTTTG GGAGAGAACT CCACAGATGG TGACCATGGG

Exon I
        250        260        270        280        290        300        310        320        330        340        350        360
CACTGGGGTG TGCCTGCTGG TGGTGGAAAC TAGAGACAGC CTGGGGTTTG GCTACACAGA TCCACCTGCA CTGGAATAGC TTTTGGCTAC CAGAGGAGGA ACAATCCTTT TGCCCGGAGA 370        380        390        400        410        420        430        440        450        460        470        480
TCTTACTGCT AGTGAGGCT TTGGACTTGA GGTCAATGA AGTCAGAGT TTGGACTTGA AGGACAGAGT CTGGGCACTA TCCCCAGGCA GTGTGAAGTT CTCCCTCCTGC TGCTGCTGTT
                                           M   K   L   R   V   G   Q   T   L   G   T   I   P   R   Q   C   E   V   L   L   L   L 490        500        510        520        530        540        550        560        570        580        590        600
TCTTACTGCC AGTGTGTAGC ACCACATACT TCCCCAAGC TCAGCAGAAA GGAGCAGAGC TGTGGGCCCT GGAGCTTCAG TGGAAGCAA CAGGCCTAGC CTATGGGCCC TTCCCGGCAG
  L   L   L 610        620        630        640        650        660        670        680        690        700        710        720
GGGTCAGTG GATGGTGCC ACCACATACT TCCCCAAGC TCAGCAGAAA GGAGCAGAGC TGTGGGCCCT GGAGCTTCAG TGGAAGCAA CAGGCCTAGC CTATGGGCCC TTCCCGGCAG
G   L   V   D   G   V   H   H   I   L   S   P   S   S   A   E   R   S   R   A   V   G   P   G   A   S   V   G   S   N   R   P   S   L   W   A   L   P   G   R Exon II
        610        620        630        640        650        660        670        680        690        700        710        720
GTAAGAGACT TGCTTTTTGG GGAAGGTACG CGTGTAGGTC CACGGACTAG ACCGGACTAG GAGTGACTGG GAAGAAGGT GGCTATTGAG GCCATGGGTG TGAGAAGGAA GGATCTGCCT 730        740        750        760        770        780
AAGAGGAGGA GGCTGTGCAA ATGCTAGCTT AAACTTGGTA CCTCGATCAA TTGCAAGGCC AGTGTTCT----------650 bp----------

10         20         30         40         50         60         70         80         90        100        110        120
TTTGTGAGTT TGAGGCCAGC CTGGTCTACA TAGTAGTCTC ATGATAGAAA TAAAAACAAA AGAATCCTTG CAATATAGTG TGCATGGGTC CTGGGAGGAA GCATAGGGCC AGTAGGAACT 130        140        150        160        170        180        190        200        210        220        230        240
GATGCACACA CGCATGTATG CACACACGCA CAAGCACATA TGCACACACA AATATTCACC AGAGATTCCT GGTTCCACCA CACCCACCAG AGAGATATA CCACCCAGGA ATTTCTGAGA 250        260        270        280        290        300        310        320        330        340        350        360
ATCTGCTGGG CCTGATATTG CCATCAACAC TGAAAAATTC AGAGATGGAA GTAAGAGATO GATAGATGGA CTTGTCGGGA TACTGGCTGC TGATCTATTT TCTGCCAAGG ACATAGTTTA
```

```
                                                              Exon II
                                                                400
        339          350
7pB12        TTCTGCCAAGGACATAGTTTATTTCCTGAAGTTCTGTGTCTGACTCACCCAACAG CTCCTGTTCCAGATCATCCCACGGGGAGCAGG
             ||  |||    ||| |||     |    | |||       ||     ||||       |||  | |||| |||||
J-λ-2        TACCACCCACTGC TTCTCAAGTGAGGTCATAGTCCACCCATTGTAGCTAGCTAGTAGTTTGATCAGCTCAGTGTGAGAGAACAGG 520
                                          500
        TCCCAGGTGCTGCGGCCCCATAGGCTTCCATCTAAGCCCCAG  TTTGGTATGTCTTTGGTGGGGGACCCAGCTCACAATCCTAGGTAAGTGGTT
        |||||||  |||||||||| |||||  |||   ||  |||   |||   ||| || |||| |||| ||       |||||    ||||||||  |||
        ACCAGGTGCTGGCCCCATAGGTTTTGGGTTGGGTTTGGGTTTAGTCATTGTGGGCGGTGAACCAAGGTCACTGTCCTAGGTAAGTAGTT
                            450
```

Fig. 16

```
              450         460         470         480         490
          Q   C   E   V   L   L   L   L   L       L   G   L   V   D   G
7pB12    CAGTGTGAAGTTCTCCTCCTGCTGCTG----TTGGGTCTAGTGGATGGTG
         ||| ||||||||| ||||||||| ||    ||||| |||||
         GTTCACCTCCTGCTCCTGGGTTTTGGG
         113                                            143
```

TCR-γ LEADER

```
        500         510         520         530         540         550         560
         V   H   H   I   L   S   P   S   S   A   E   R   S   R   A   V   G   P   G   A   S   V
        TCCACCACATACTTTCCCCAAGCT-CAGCAGAAAGGAGCAGAGCT-GTGGGCCCTGGAGCTTCAGTG
        |||| ||||| ||| ||||| ||| |||||| ||| |||||| |||  ||||  ||  ||| ||||||
        AGCTTCAGCAGTCAGGACCTGAGCTGGTGAAACCTGGGGCCTCAGTG
        348                                                              394
```

V_HII FR1

F I G. 19

```
                                                         +50                                          +60                                  +70                                 +80
               P  G  H  P  P  R  F  L  L  R  Y  F  S  H  S  D  K  H  Q  G  P  D  I  P  P  R  F  S  G  S  K  D  T  T  R  N  L  G  Y  L
7pB12-2        CGGGCCACCCCTCCCAGGTTCCTGCTGCGCTACTTCTCACACTCAGAGAAGCACCAGGGTCCGATATCCCACCTGCTTCTCCGGGTCCAAAGATACGACCAGGAACCTGGGTATCTGA    720
pZ121          ------------------------------------------------------------------------------------------------G------------------
7pB70-1                                                                                                                    (A)

+90                                   +100                                      +110                                       +120
               S  I  S  E  L  Q  P  E  D  Q  A  V  Y  Y  C  A  V  G  L  R  S  Q  E  K  K  R  M  E  R  E  M  E  G  E  K  S  Y  T  D  L
7pB12-2        GCATCTCTGAACTCTGAGCCTGAGGACGAGGCTGTGTATTACTGTGCCGTGGGGCTCCGGAGCCAGGAGAAGAAGAGAATGGAAGCAGTGGGAAGGAGAAAAGTCGTATACAGATTTGG    840
pZ121          --------------------------------------------C-T--------------------------------A----------------------------------
7pB70-1                                                  (H)

G  S  *
7pB12-2        GATCTTAGGCTCTCGGAGACATTCAGACCCCTGAACTGAAGACAGAGTTGCTTCGCTCGGCTAGTCTCGGTATGGAAGGAGGGTAGAACGTGAGGTTTGCAGAGCCTAGAAGATGGAAT    960
pZ121          -----------------------------------------C-----------------------------T---G--C-------------------------G-----------
7pB70-1

7pB12-2        TATGCAGCTTTTCCTTGTTCTGCGGGTTGCTATGAGCCCCATTGGAGGCTGGATTGTAGAATTAAAGCTGTTTTACTGAATTTGCTCTGG                         1053
pZ121          -------------C---------------------------C----------------------------------G-------- poly A ~20
7pB70-1
```

```
                                                                                                    120
Human  [GT] GAGGGAACCCCCAGATCCCAAAGACTCC TGCCCCTTCCTTCATCCTGCCCTGCCCCCACGGGCCACATGCA
            *   *** *** ** **          * ** *** * ****     *        ***  ****
Mouse  [GT] AAGGGAACTCTTGGGGTCCAGGGCTTCCTTGCTCCTCCTGCTGGCCTGCTTCTGCCCTGCCCCCAGTGATGGACATGCT 180
              + Leader | FRI →
              G   C   G   P   Q     V   L   H   Q   P   P   A   M   S   S
Human  TCTGTGTCACC [AG] GT TGT GGT CCT CAG GTG CTA CAT CAG CCG GCC ATG TCC TCG
       *  * *** *        *              **   *       *       *  *** *   *
Mouse  TCTATCTTCTC [AG] GT TGT GGC CCT CAG CCC ATG GTG CAT CAG CCA TCA GCA TCT TCT
                         G   C   G   P   Q   P   M   V   H   Q   P   S   A   S   S 240
                          + FRI | CDRI →
       13    A   L   G   T   T   I   R   L   T   C   T   L   R   N   D   H   D   I   G   V
Human  GCC CTT GGA ACC ACA ATC CGC CTC ACC TGC ACC CTG AGG AAC GAC CAT GAC ATC GGT GTG
       *    *   *   *   *               *   *       *          *   *   *       *  ***
Mouse  TCC CTT GGA GCC ACC ATC CGC CTC TCC TGT ACC CTG AGT AGC AAC GAC CAT GAC CAT GGC ATT
        S   L   G   A   T   I   R   L   S   C   T   L   S   S   N   D   H   D   H   G   I 300
              + CDRI | FRII →                                + FRII | CDRII →
       33    Y   S   V   Y   W   Y   Q   Q   R   P   G   H   P   P   R   F   L   L   R   Y
Human  TAC AGC GTC TAC TGG TAC CAG CAG AGG CCG GGC CAC CCT CCC AGG TTC CTG CTG AGA TAT
        *   *       *                       *           *   *           *           *
Mouse  TAC AGC ATT TAC TGG TAC CAG CAG CAG CCG GGC CAC CCC AGG CGC AGG TTC CTG CTG AGA TAC
        Y   S   I   Y   W   Y   Q   Q   Q   P   G   H   P   R   R   R   F   L   L   R   Y
```

Fig. 27 (cont.)

```
                          ← CDRII | FRIII →
       53
        F   S   Q   D   K   S   Q   G   P   P   V   P   P   R   F   S   G   S   K
Human  TTC TCA CAA GAC AAG AGC CAG GGC CCC CAG GTC CCC CCT CGC TTC TCT GGA TCC AAA
                    **              *   ***              **           *
Mouse  TTC TCA CAC TCA GAC AAG CAC CAG GGT CCC GAT ATC CCA CGC TTC TCC GGG TCC AAA   360
        F   S   H   S   D   K   H   Q   G   P   D   I   P   R   F   S   G   S   K
                +           +   +       +   +   +   +       +   +   +   +   +   +

← FRIII →
       73
        D   V   A   R   N   R   G   Y   L   S   I   S   E   L   Q   P   E   D   E   A
Human  GAT GTG GCC AGG AAC AGG GGG TAT TTG AGC ATC TCT GAG CTG CAG CCT GAG GAC GAG GCT
                *               **          *                   *
Mouse  GAT ACG GCC AGG AAC CTG GGG TAT CTC AGC ATC TCT CTG GAA CTG CAG CCT GAG GAC GAG GCT   420
        D   T   A   R   N   L   G   Y   L   S   I   S   L   E   L   Q   P   E   D   E   A
        +       +   +   +       +   +       +   +   +       +   +   +   +   +   +   +   +

← FRIII | Non Ig →
       93
        M   Y   C   A   M   G   A   R   S   S   E   K   E   E   R   E   W
Human  ATG TAT TAC TGT GCT ATG GGG GCC CGC AGC TCG GAG AAG GAG AGG GAG TGG
        *                   *   ***       **      ***   *   *       *
Mouse  GTG TAT TAC TGC GCT GTG GGG CTC CGG AGC CAC GAA AAG ATG AGA GAG TGG   480
        V   Y   Y   C   A   V   G   L   R   S   H   E   K   M   R   E   W
            +   +       +       +       +   +           +           +   +

113
        E   E   E   M   E   P   T   A
Human  GAG GAA GAA ATG GAA CCC ACT GCA  -   -   -    -    -
        *       **          *   **
Mouse  GAA GGA GAA AAG TCG TAT ACA GAT TTG GGA TCT TAG ■
        E   G   E   K   S   Y   T   D   L   G   S   *
        +       +       +       +       +
```

Human
Mouse

Human
Mouse

Human
Mouse

Human
Mouse

Human $V_{preB}$

NUCLEOTIDE SEQUENCES WHICH ARE SELECTIVELY EXPRESSED IN PRE-B CELLS AND PROBES THEREFOR

This application is a continuation of application Ser. No. 07/119,369 filed Nov. 10, 1987, now abandoned.

TECHNICAL FIELD

The present invention relates to nucleotide sequences which are selectively expressed in pre-B cells an to probes comprising a polynucleotide hybridizing specifically to such a nucleotide sequence. The invention further relates to replicable microbial vectors containing a polynucleotide hybridizing to a nucleotide sequence mentioned above, to host organisms transformed with such a replicable microbial vector, which hosts are capable of producing copies of said polynucleotide, to methods for the production of the probes and to a method and a test kit used for determining whether a cell is a pre-B cell using such a probe.

Moreover the invention relates to replicable microbial vectors containing a polynucleotide having a sequence which is selectively expressed in pre-B cells to host organisms transformed with such a replicable microbial vector, which hosts are capable of translating the amino acid sequence encoded by a transcript comprising said nucleotide sequence and to a polypeptide having said amino acid sequence. Furthermore the invention relates to methods for the production of said polypeptide, to methods for the production of antibodies against said polypeptide, to methods and a test kit used for the determination of said polypeptide and to the antibodies per se.

B-cells, a subclass of lymphocytes, develop from pluripotent stem cells in a series of differentiation steps in specialized organs such as fetal liver and bone marrow. During this development immunoglobulin (Ig) gene segments are rearranged to form complete Ig genes for heavy (H) and light (L) chains (Tonegawa, Nature 302, 575-581, [1983]). Rearrangements appear ordered in time of development: H chain gene segments are rearranged before L chain gene segments (Maki, et al., Science 209, 1366-1369, [1980]; Alt, et al., Cell 27, 381-390, [1981]; Perry, et al., Proc. Natl. Acad. Sci. USA 78, 247-251, [1981]; Coffman, et al., J. Mol. Cell. Immunol. 1, 31-38, [1983]; Reth, et al., Nature 317, 353-355, [1985]). This distinguishes different stages of precursor (pre)-B cell development.

The most immature pre-B cell appears to have only $D_H$ segments rearranged to $J_H$ segments. Pre-B cells follow in which $V_H$ segments have been rearranged to $D_HJ_H$ segments (Alt et al., supra; Sugiyama, et al., Nature 303, 812-815, [1983]; Alt, et al., EMBO J. 3, 1209-1219, [1984]). The next stage is a pre-B cell which has not only rearranged $V_HD_HJ_H$, but also $V_K$ to $J_K$ (Maki, et al., supra; Lewis. et al., Cell 30, 807-816, [1982]; Burrows, et al., Nature 306, 243-246, [1983]), and finally, $V_\lambda$, to $J_\lambda$ (Hieter, et al., Nature 290, 368-372, [1981]).

The result of this process of B cell development is a resting, IgM- and/or IgD-positive B cell which can be stimulated by antigens or mitogens to divide and to mature into memory cells and into Ig-secreting plasma cells which often have switched their IgH gene expression and therefore synthesize other classes of Ig. By analysing the rearrangement pattern of its Ig genes the stage of development of a given B cell may be determined. Since for each cell at a given stage of normal lymphocyte differentiation there exists a malignant counterpart, an analysis of the rearrangement pattern may also be used for the classification of leukemias as shown in European Patent Application Publication No. 149 547 (published Jul. 24, 1985). However the Southern blot technique (Southern, J. Mol. Biol. 98, 503-517, [1975]) used in the method described in the above mentioned patent application is time consuming and relatively complicated in comparison with other methods used routinely in clinical laboratories.

The identification of stages of pre-B and B cell development (the B cell lineage) is also aided by monoclonal antibodies which characterize surface membrane markers that are preferentially expressed on subsets of pre-B and B lymphocytes or plasma cells (McKearn et al., J. Immunol. 132, 332-339, [1984]; Coffman, et al., Nature 289, 681-683, [1981]); Kincade, et al., J. Immunol. 127, 2262-2268, [1981]). But the markers recognized by these antibodies have been found to be also expressed on other lineages of blood cells and can accordingly not be used to specifically and unambiguously determine the stage of differentiation of a given B cell or its malignant counterpart.

SUMMARY OF THE INVENTION

The present invention solves the problems mentioned above by providing a new tool for the determination of the stage of differentiation of B cells, more precisely for the determination of pre-B cells. Such a tool may be used to determine if a given leukemia is of the non-T acute lymphoblastic leukemia type (non-T ALL) or not. Furthermore the present invention provides methods for obtaining and using said tool.

The present invention provides isolated nucleotide sequences selectively expressed in pre-B cells, and fragments thereof. Said pre-B cells are mammalian cells, preferably human or mouse cells. Such a nucleotide sequence may be obtained by subtraction hybridization, a method in which nucleotide sequences which are expressed in pre-B cells and in other cells are eliminated and only those sequences are selected which are selectively expressed in pre-B cells.

The nucleotide sequence is characterized in that DNA complementary to mRNA from pre-B cells hydridizes to said nucleotide sequence under conditions generally known in the art as conditions for the detection of low to medium abundance mRNA's (Maniatis, et al., supra, pp. 224-228) such as the conditions described in the Example, whereas DNA complementary to mRNA from non-pre-B cells (e.g., mature B cells, plasma cells, T cells and other lineage cells) does not hybridize. By using a cell line derived from a B cell tumor, large numbers of identical cells are available. A pre-B lymphoma cell line is preferably used to select said sequence. An example of such a lymphoma cell line is the mouse pre-B lymphoma cell line 70Z/3 (deposited at the American Type Culture Collection [ATCC], 12301 Parklawn Drive, Rockville, Md. 20852, U.S.A., its accession number being ATCC No. TIB 158). The following nucleotide sequences were found to be selectively expressed in pre-B cells:

GGAATAGCTTTTGGCCACCAGAGGA

-continued

```
GGAACAATCCTTTTGCCGGGAGATCTACACTGCAAGTGAGGCTAGAGTTGACTTTGGACT
TGAGGGTCAATGAAGCTCAGAGTAGGACAGACTCTGGGCACTATCCCCAGGCAGTGTGAA
GTTCTCCTCCTGCTGCTGCTGTTGGGTCTAGTGGATGGTGTCCACCACATACTTTCCCCA
AGCTCAGCAGAAAGGAGCAGAGCTGTGGGCCCTGGAGCTTCAGTGGGAAGCAACAGGCCT
AGCCTATGGGCCCTTCCCGGCAGGCTCCTGTTCCAGATCATCCCACGGGGAGCAGGTCCC
AGGTGCTCGCCCCATAGGCTTCCATCTAAGCCCCAGTTTTGGTATGTCTTTGGTGGTGGG
ACCCAGCTCACAATCCTAGGTCAGCCCAAGTCTGACCCCTTGGTCACTCTGTTCCTGCCT
TCCTTAAAGAATCTTCAGCCAACAAGGCCACACGTAGTGTGTTTGGTGAGCGAATTCTAC
CCAGGTACTTTGGTGGTGGACTGGAAGGTAGATGGGGTCCCTGTCACTCAGGGTGTAGAG
ACAACCCAACCCTCCAAACAGACCAACAACAAATACATGGTCAGCAGCTACCTGACACTG
ATATCTGACCAGTGGATGCCTCACAGTAGATACAGCTGCCGGGTCACTCATGAAGGAAAC
ACTGTGGAGAAGAGTGTGTCACCTGCTGAGTGTTCTTAGAGCACAATCCTCCCTGAAGCC
TCAGGGGCCTGGATCTGAAGTGCCAGAAAAAGTTGTTTTTTGTTTTGTTTTTTGTTTTTT
TTCCCATTAACCATCTCACTGTCTTTCCTGTGCCTAATACTCAATAAATATCTTACCACC
AACC.
CCAGAAAGCCTGGGAGGGTGGTGAGCAGGAACCAGGGGTGCAGTGACCCTCTCCCCAAAG
CAGGGAGGAGAGTGCTTCCCAGCTGGTCAGGGCCCAGGAGCAGTGGCTGTAGGGGGCAGG
GTGCTGCAGGTCTGGAGCCATGGCCTGGACGTCTGTCCTGCTCATGCTGCTGGCCTATCT
CACAGGTTGTGGCCCTCAGCCCATGGTGCATCAGCCACCATTAGCATCTTCTTCCCTTGG
AGCCACCATCCGCCTCTCCTGTACCCTGAGCAACGACCATAACATTGGCATTTACAGCAT
TTACTGGTACCAGCAGAGGCCGGGCCACCCTCCCAGGTTCCTGCTGAGATACTTCTCACA
CTCAGACAAGCACCAGGGTCCCGATATCCCACCTCGCTTCTCCGGGTCCAAAGATACGAC
CAGGAACCTGGGGTATCTGAGCATCTCTGAACTGCAGCCTGAGGACGAGGCTGTGTATTA
CTGTGCCGTGGGGCTCCGGAGCCAGGAAAAGAAGAGGATGGAGAGGGAGTGGGAAGGAGA
AAAGTCGTATACAGATTTGGGATCTTAGGCTCTGGAGACATTCAGACCCTGAACTGAAGA
CAGAGTTTGCTTTGCTCGGCTAGTCTGGTATGGGAAGGAGGGGTAGAACGTGAGGTTTTG
CAGAGCCTAGAAGATGGAATTATGCAGCTTTTCCTTGTTCTGCGGTGTTGCTATGAGCCC
CCATTGGAGGCTGGATTGTAGAATTAAAGCTGTTTTTACTG and
GAGCTCTGCATGTCTGCACCATGTCCTGGGCTCCTGTCCTGCTCATGCACTTTGTCTACT
GCACAGGTGAGGGAACCCCCAGATCCCAAAGACTCCTGCCCCTTCCTTCATCCTGCCCTG
CCCCCACGGGCCACATGCATCTGTGTCACCAGGTTGTGGTCCTCAGCCGGTGCTACATCA
GCCGCCGGCCATGTCCTCGGCCCTTGGAACCACAATCCGCCTCACCTGCACCCTGAGGAA
CGACCATGACATCGGTGTGTACAGCGTCTACTGGTACCAGCAGAGGCCGGGCCACCCTCC
CAGGTTCCTGCTGAGATATTTCTCACAATCAGACAAGAGCCAGGGCCCCCAGGTCCCCCC
TCGCTTCTCTGGATCCAAAGATGTGGCCAGGAACAGGGGGTATTTGAGCATCTCTGAGCT
GCAGCCTGAGGACGAGGCTATGTATTACTGTGCTATGGGGGCCCGCAGCTCGGAGAAGGA
GGAGAGGGAGAGGGAGTGGGAGGAAGAAATGGAACCCACTGCAG
```

The invention therefore provides these nucleotide sequences or homologous or degenerate sequences thereof, i.e., nucleotide sequences having the same function but originating from a different species, or nucleotide sequences being degenerate in the genetic code.

The invention further provides probes comprising a polynucleotide hybridizing specifically to a transcript comprising one of the nucleotide sequences mentioned above and a label used for the detection of hybrids formed between a transcript comprising a nucleotide sequence defined above and the polynucleotide of the probe. Said label may be directly associated with the polynucleotide of the probe or may recognize the formation of hybrids between the polynucleotide of the probe and the transcript with a nucleotide sequence selectively expressed in pre-B cells. Preferably the sequence of the polynucleotide of the probe is complementary to one of the nucleotide sequences shown above or to parts thereof. Such a polynucleotide may be prepared by using conventional polynucleotide synthesis procedures or by methods known in the art of recombinant DNA technology for the production of multiple copies of said polynucleotide (see for example Maniatis, et al., "Molecular Cloning—A Laboratory Manual", Cold Spring Harbor Laboratory [1982]).

The invention further provides replicable microbial vectors containing the polynucleotide of the probe and host organisms containing such a replicable microbial vector, which hosts are capable of producing copies of said polynucleotide. By incorporating a label into the polynucleotide obtained by the methods indicated above a probe capable of showing hybridization to a nucleotide sequence which is selectively expressed in pre-B cells is obtained. The present invention also provides such probes and methods for their production. In addition, the invention provides a method and a test kit for determining whether an unknown cell is a pre-B cell using said probe. Moreover the invention provides replicable microbial vectors containing a polynucleotide with a sequence which is selectively expressed in pre-B cells; host organisms transformed with such replicable microbial vectors, which hosts are capable of expressing the amino acid sequence encoded by the polynucleotides of said replicable microbial vectors; and polypeptides having said amino acid sequences. Furthermore the invention provides methods for the production of said polypeptides, methods for the production of antibodies against said polypeptides methods and test kits used for the determination of said polypeptides, and the antibodies per se.

BRIEF DESCRIPTION OF THE FIGURES

The invention will be better understood on the basis of the following detailed description when considered in connection with the accompanying FIGS. 1–29. These Figures show:

FIG. 6 Localization of cells containing pZ 183 specific mRNA molecules in day 16 fetal liver. Cells were digested with 30 μg/ml pronase. Exposure time 63 days. Bars 5 μm. a) Hybridization with pZ 183 negative strand probe. b) Hybridization with pZ 183 positive strand probe.

FIG. 8 Nucleotide sequence of the 0.7 kb insert of clone pZ 183-1. The proposed poly(A) attachment site is underlined.

FIG. 9 Amino acid sequence of the J-like (a) and C-like (b) portions of pZ 183-1 encoded by the nucleotide sequence in FIG. 8 in frame 1 and alignment with the corresponding sequences of $\lambda 1L$, $\lambda 2L$, $\kappa L$, $J_H$ and $C_\mu 1$ (for references see: Bothwell, et al., Nature 298, 380–382, [1982] and Kabat, et al., in "Sequences of proteins of immunological interest", NIH, Bethesda, U.S.A., [1983]) and $J_\alpha C_\alpha 1$, $J_\beta C_\beta$ and $J_\lambda C_\lambda$ of the $\alpha$, $\beta$ and $\gamma$ chains of the T cell receptor (Saito, et al., Nature 312, 36–40, [1984]; Hedrick, et al., Nature 308, 149–158, [1984]).

For nucleotide positions corresponding to the first and the last deduced amino acid of the J-like and C-like sequences of pZ 183-1 see Table II. Those residues common between pZ 183-1 and any other sequence are boxed. Residues conserved in all sequences or conserved in light chains are boxed together.

FIG. 10 Southern blot analysis of HindIII digested DNA from 70Z/3 cells. The pZ 183-1 gene is carried on a HindIII fragment in the genome of 70Z/3 cells which is different from the HindIII fragments carrying the $c\lambda 1$ or the $c\lambda 2$ sequences. The following probes were used for hybridization: pZ 183-1 (lane 1), $c\lambda 1$ sequence on the XhoI-PstI fragment of pAB1-1 (Bothwell et al., supra) (lane 2), pZ 183-1 and $c\lambda 1$ (lane 3) and $c\lambda 2$ sequence on the 450 bp SacI fragment described in Weiss et al., Eur. J. Immun. 15, 765–768 [1985] (lane 4).

Figure 11:
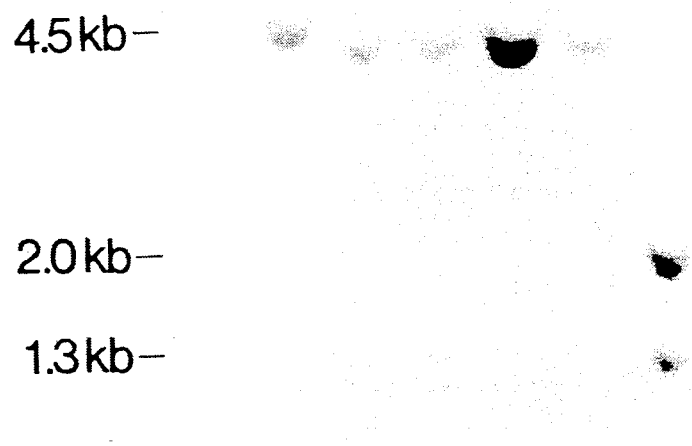

FIG. 11 Southern blot analyses of DNA from liver of (C57BL/6J×DBA/2) $F_1$ mice (a) and from 70Z/3 pre-B cells (b). showing that the gene is cut by PstI and EcoRI. DNA was digested with the indicated enzymes. The filter was hybridized with $^{32}$P-labelled insert DNA of cDNA clone pZ 183-1.

Figure 12:
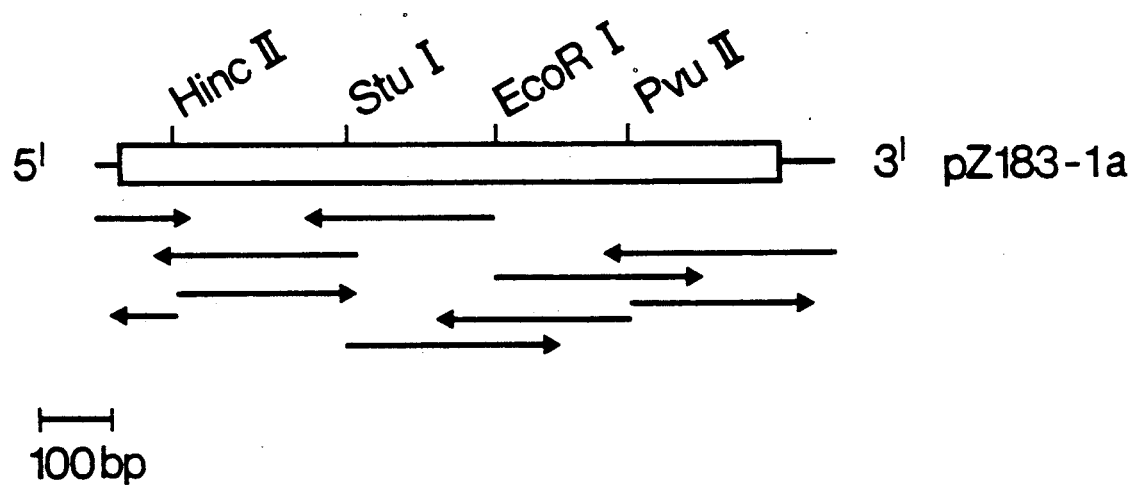

FIG. 12 Strategy for sequencing the cDNA clone pZ 183-1a. The arrows indicate the direction and the length of sequence determined by subcloning the indicated fragments into M13.

Figure 13:
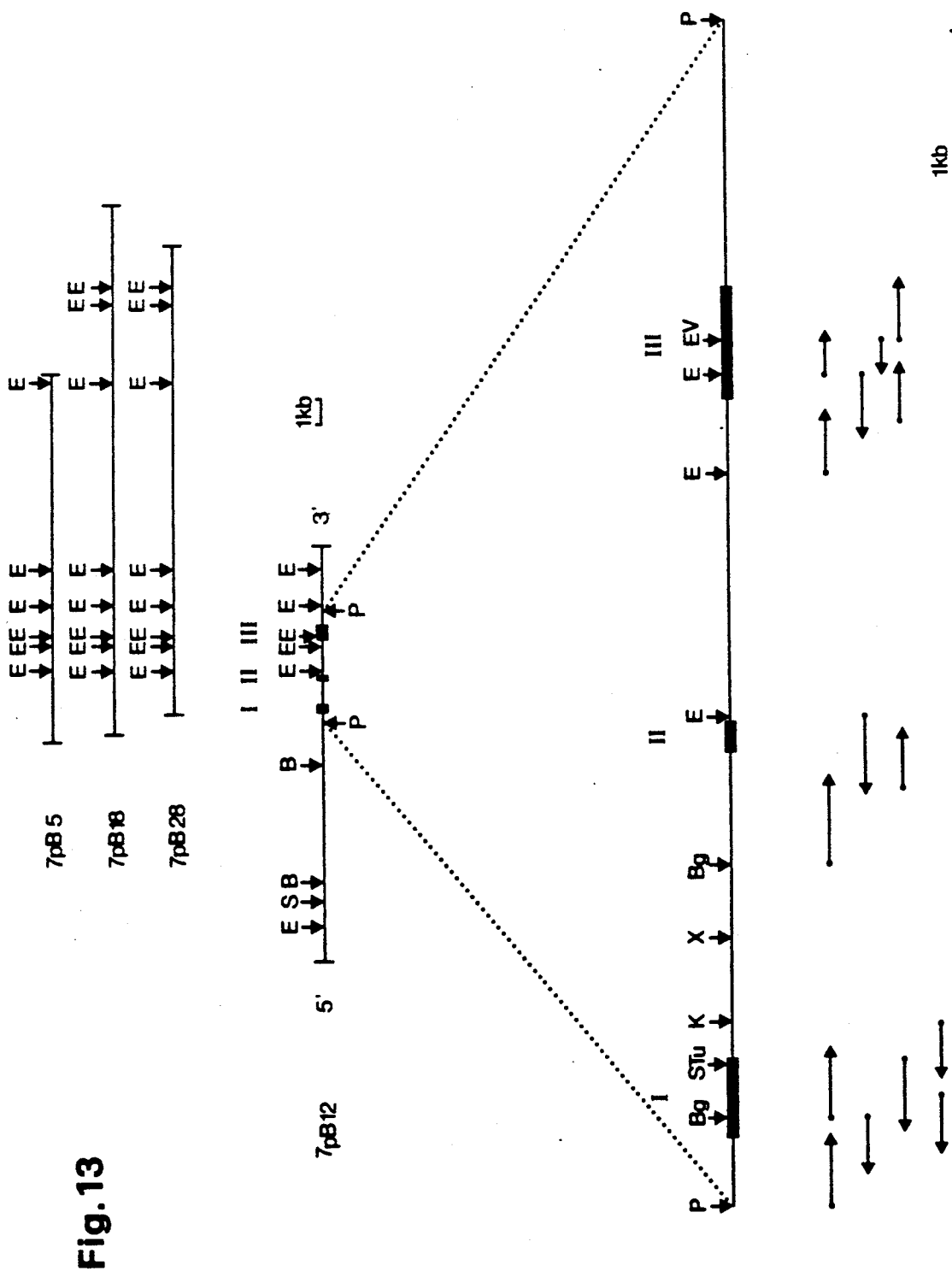

FIG. 13 The restriction maps of four overlapping $\lambda 5$ genomic clones, 7pB5, 7pB12, 7pB18 and 7pB28 are shown. The 4.7 kb PstI fragment of 7pB12 was subcloned into pUC-18 and a more detailed restriction map was determined.

Restriction sites are B=BamHI; Bg=BglII; P=PstI; E=EcoRI; EV=EcoRV; K=KpnI; S=SalI; STu=StuI; X=XbaI. The fragments indiated by arrows were sequenced by the M13 dideoxy chain termination method. The positions of the three exons in the $\lambda 5$ gene (see FIG. 14) are indicated with I, II and III.

Figure 14:
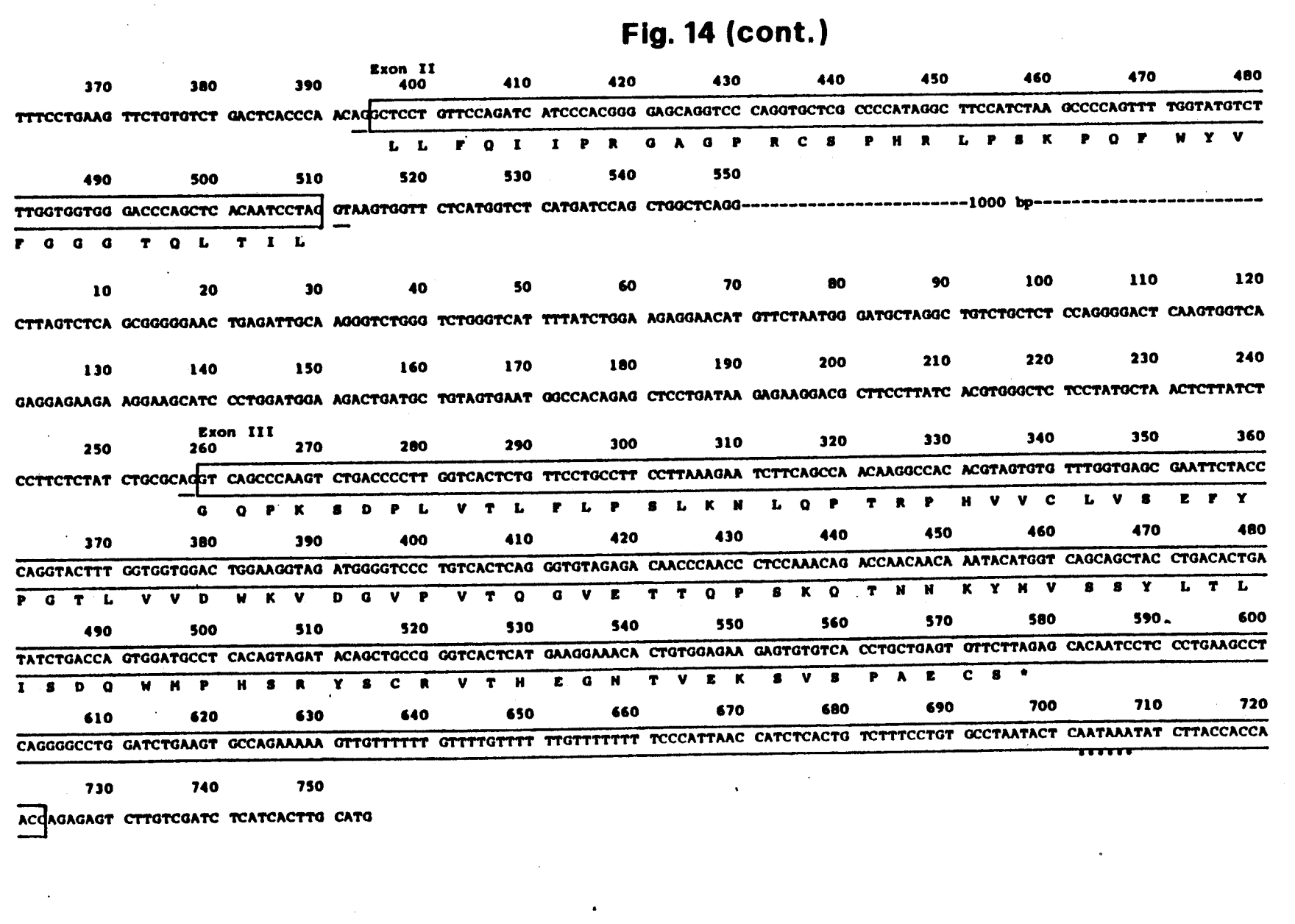

FIG. 14 Nucleotide sequence of the genomic form of $\lambda 5$ containing all cDNA sequences and the amino acid sequences deduced from them. cDNA sequences of the pZ183-1a clone are boxed. The sequences are divided into three parts which show the three exons and genomic sequences 5' and 3' adjacent to them. a and b indicate the major sites of initiation of transcription determined by the primer extension experiment shown in FIG. 17. The 18 nucleotides synthesized as a primer for the extension method are indicated with a broken line over the sequence. Sequences boxed in broken lines indicate the 5' part of exon I determined by this primer extension method (see FIG. 17). GT (donor) and AG (acceptor) splicing signal sequences of introns are underlined. The triplet indicated by three closed circles (•) above the sequence shows the possible translation start codon ATG. The sequence underlined by six circles shows the poly (A) addition signal sequence.

Figure 15:
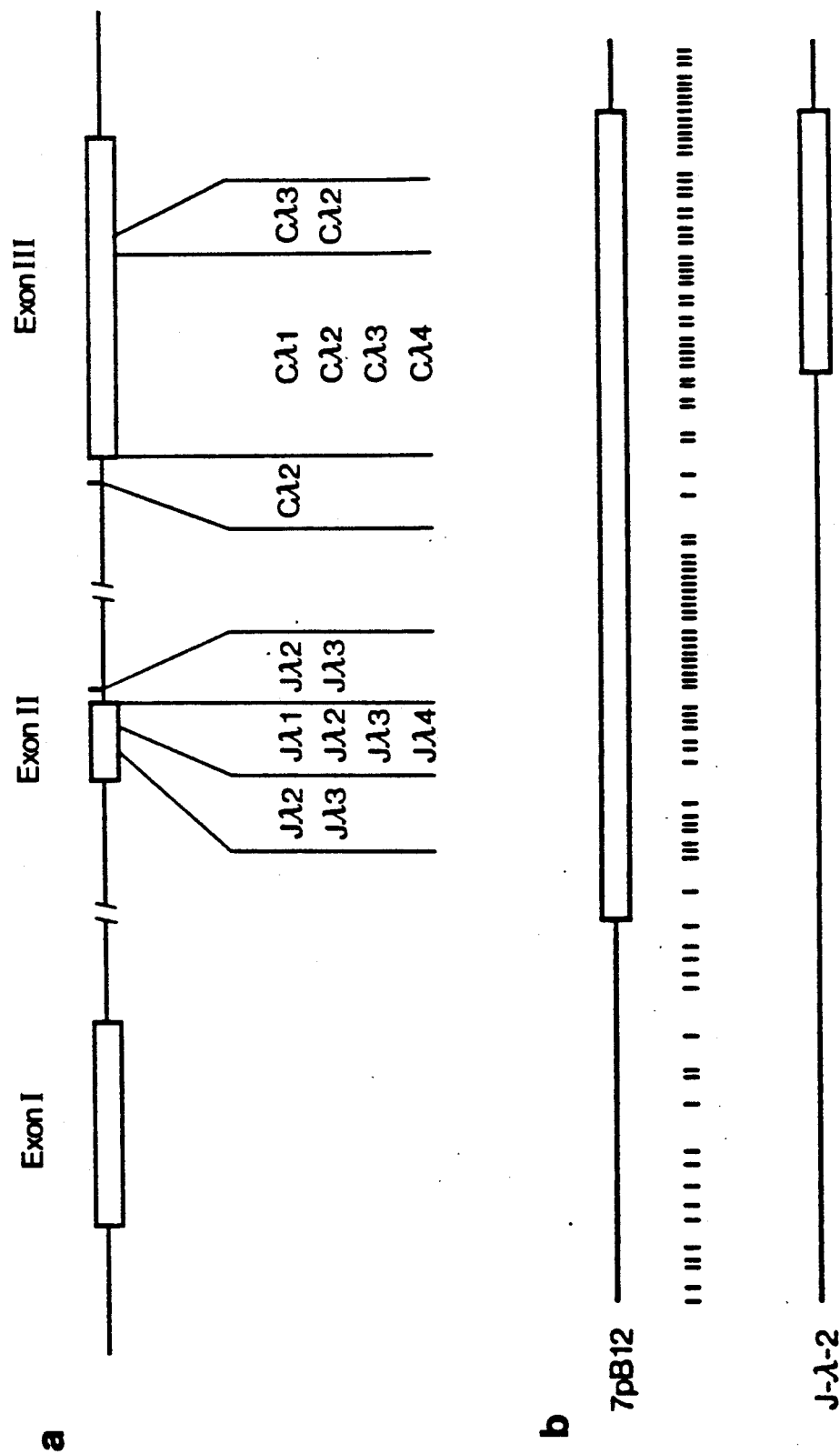

FIG. 15
a) Homologies of $\lambda 5$ genomic sequences with genomic $\lambda L$-chain sequences. The homologies are listed in detail in Table III. In general, homologies of $\lambda 5$ to $\lambda L$ chain sequences appear higher in exons than in introns.
b) Sequence homologies between areas in and around exon II of $\lambda 5$ (7pB12), and areas in and around the exon for J$\lambda 2$. Genomic sequences in and around exon II of 7pB12 were aligned with those in and around the exon for J$\lambda 2$, allowing one deletion in the sequence of 7pB12, and two in J$\lambda 2$. Dashes indicate identity of nucleotide for the two sequences. Exons are boxed. Recombination signal heptamer and nonamer sequences (Sakano. et al., Nature, 280, 288–294, [1979]) adjacent to the exon of J$\lambda 2$ are underlined.

FIG. 16 Comparison of the nucleotide sequence of Exon I of the $\lambda 5$ gene with those of the murine T cell receptor $\gamma$ chain and the immunoglobulin heavy chain $V_{HII}$ segment. Dashes show identity of nucleotide. The sequences between position 448 and 562 in Exon I or 7pB12 are compared with murine T cell receptor $\gamma$ chain leader sequences (TCR-$\gamma$ leader, site: DFL12 113–143; Kranz, et al., Nature 313, 752–755, [1985]) and murine immunoglobulin heavy chain $V_{HII}$ framework 1 region ($V_{HII}$ FR1, site; $V_H$108 348–394; Givol, et al., Nature 292, 426–430, [1981]) by computer analysis (GenBank TM, Los Alamos National Laboratory, Los Alamos, U.S.A., release 35.0, [1985]).

Figure 17:
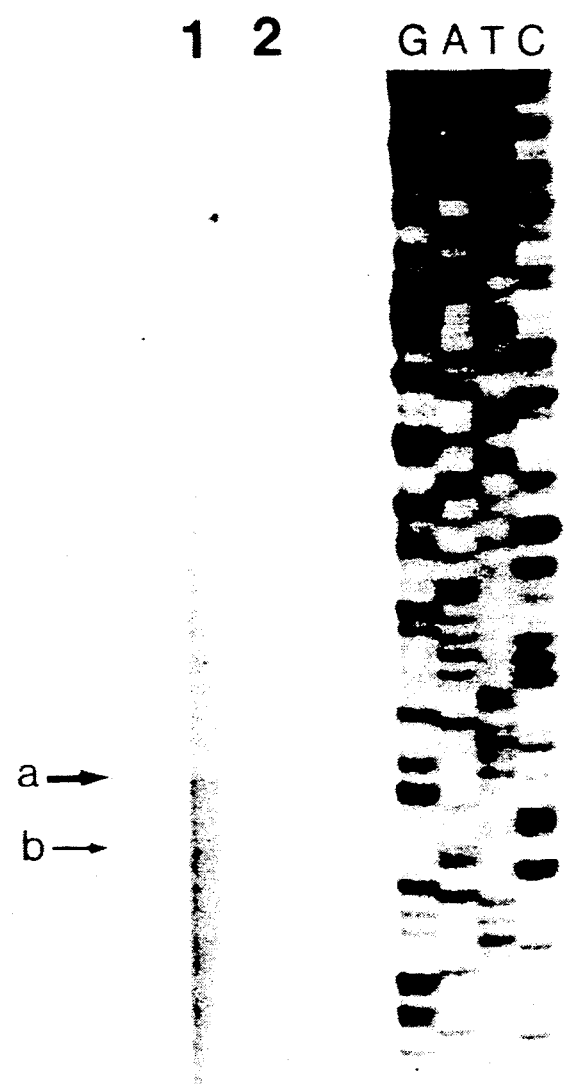

FIG. 17 Primer extension analysis of the 5' end of $\lambda 5$ mRNA. The synthetic oligonucleotide 5'-CAGAGTCTGTCCTACTCT-3' complementary to a 18 nucleotide sequence in Exon I (see FIG. 14, position 416–433) was labeled and hybridized to pre-B cell line 40E-1 poly A containing RNA (lane 1) and yeast t-RNA (lane 2).

Sequencing of the 5' region of the $\lambda 5$ gene using the synthetic oligonucleotide was carried out to determine the transcription start site. The sequencing pattern shown for comparison is that of the opposite strand of 7pB12 whose sequence is shown in FIG. 14.

Two major transcription start sites were found. The site located more 5' contains an A (indicated by a), while the one located more 3' does not (indicated by b).

Figure 18:
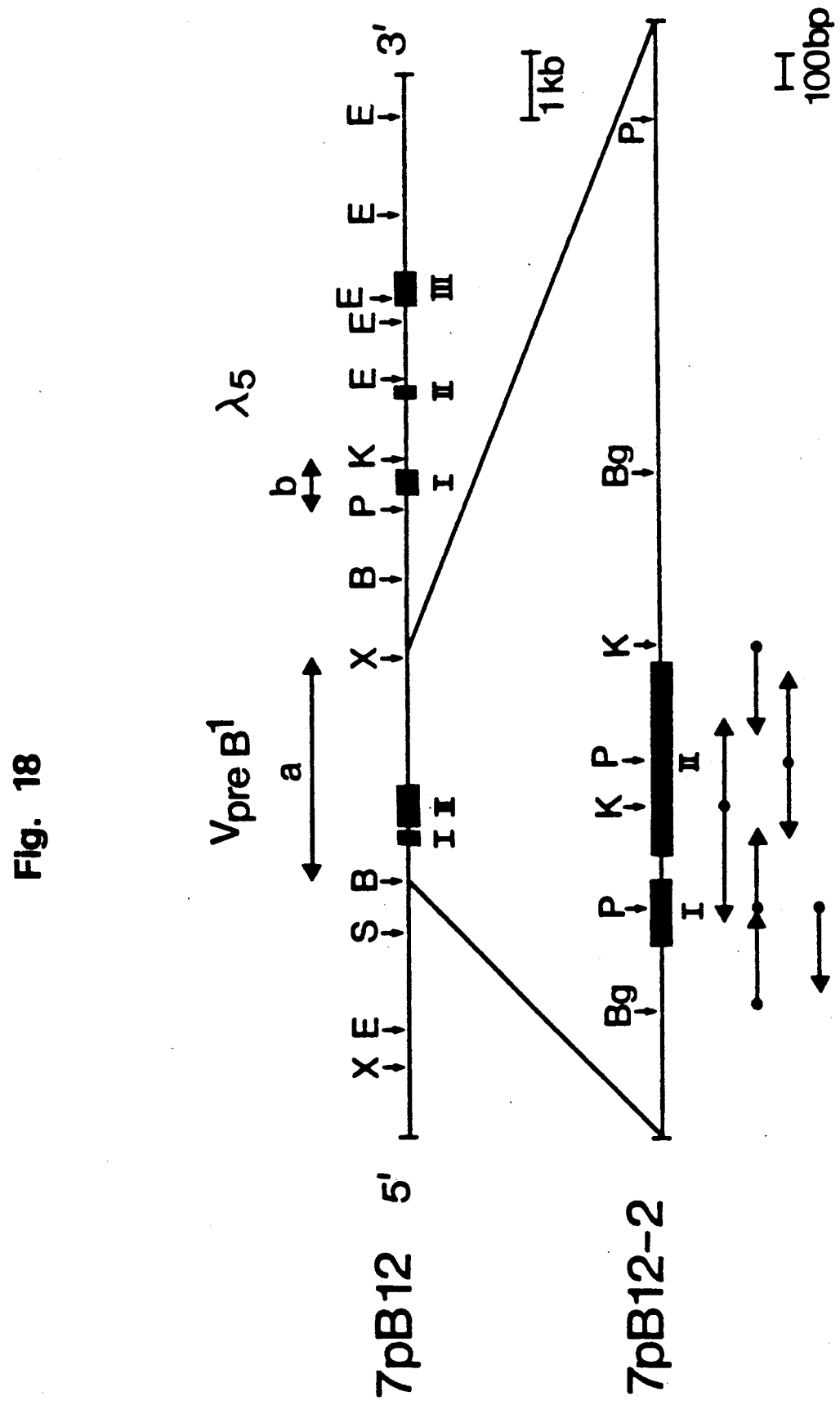

FIG. 18 Restriction enzyme map of the subclone 7pB12-2 containing a BamHI-XbaI fragment of the genomic clone 7pB12 cloned into pUC18. The arrows indicate the length of the fragments used for subcloning into M13 and the direction in which the given fragment was sequenced. The abbreviation for the restriction enzymes are the same as in FIG. 13. The positions of the two exons in the $V_{preB}1$ gene are indicated by I and II.

FIG. 19 Northern analysis (Rave, et al., Nucleic Acids Res. 6, 3559-3567, [1979]) of 10 µg total RNA from 70Z/3 pre-B lymphoma and from EL4 thymic lymphoma cells probed with the BamHI-XbaI fragment of 7pB12 (see FIG. 18, subclone a) and with the λ5 KpnI-PstI fragment (see FIG. 18, subclone b). The same filter was hybridized first with the oligolabelled pZ 121 in 50% formamide at 39° C., washed with 0.1×SSC, 0.1% SDS at 50° C., exposed to X-ray film (Kodak XS-1) then the radiolabelled probe was washed off at 0.1×SSC, 0.1% SDS at 95° C., and thereafter exposed to the second oligolabelled probe, pZ 183-1, again washed in 0.1×SSC, 0.1% SDS at 50° C., and again exposed to X-ray film.

Figure 20:
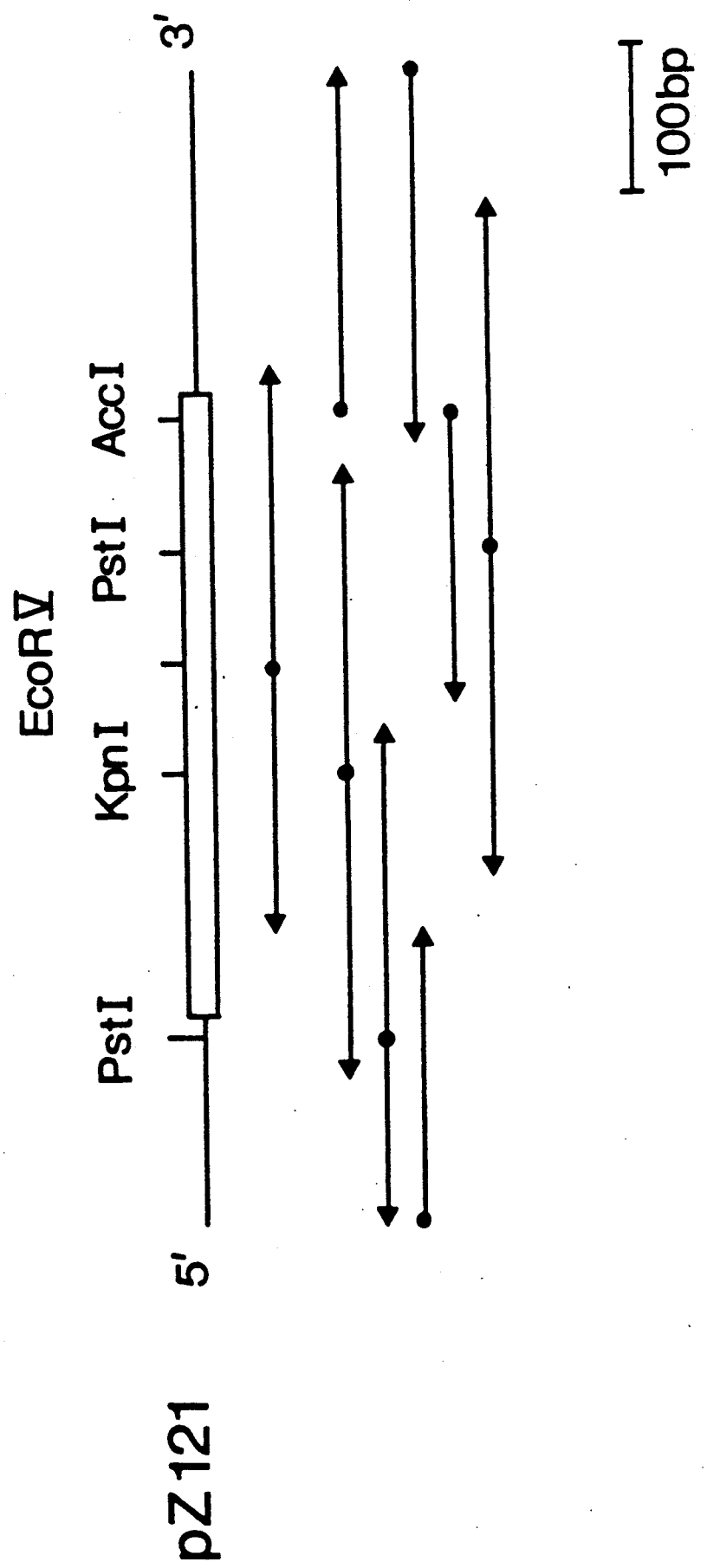

FIG. 20 Restriction enzyme map of the pZ 121 cDNA clone. The arrows indicate the length of the fragments used for subcloning into M13 and the direction in which the given fragment was sequenced.

Figure 21:
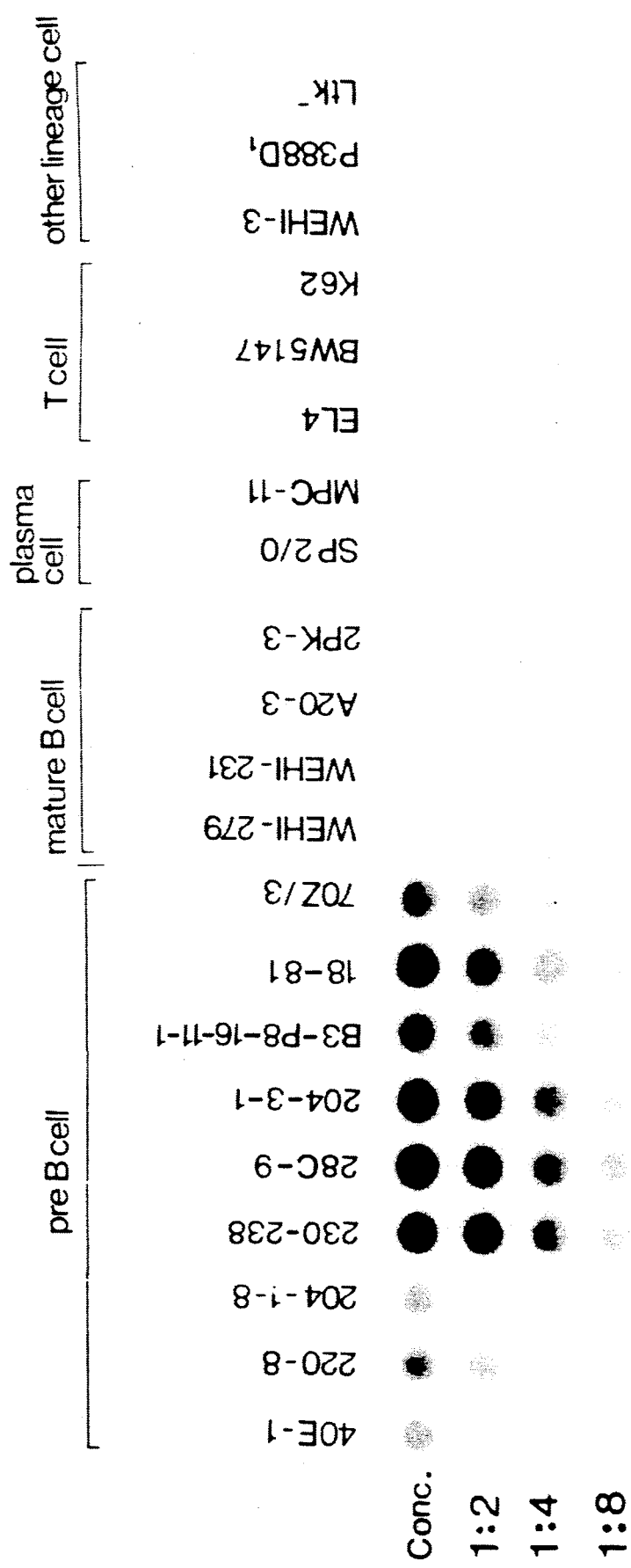

FIG. 21 Quantitative Northern dot blot analysis of pZ 121 ($V_{preB}1$) transcripts in different cell lines. Serial two fold dilutions were blotted on nitrocellulose filters for hybridization with the oligo-labelled EcoRI-AccI fragment of pZ 121. The cell lines used to show the pre-B cell specificity have already been used before (see FIGS. 1 and 2 and Table I) with the exception of B3-P8-16-11-1 which is an Abelson virus transformed pre-B cell and which was obtained as described below. Prehybridization and hybridization were performed with 1.5×SSPE, 1.0% SDS, 0.5% nonfat powdered milk, 0.5 mg/ml carrier salmon sperm DNA. Filters were washed finally with 0.1×SSC, 0.1% SDS at 60° C. Filters were probed with radiolabelled pZ 121 cDNA. "Conc." indicates RNA amounts between 1 and 5 µg per dot.

Figure 22:
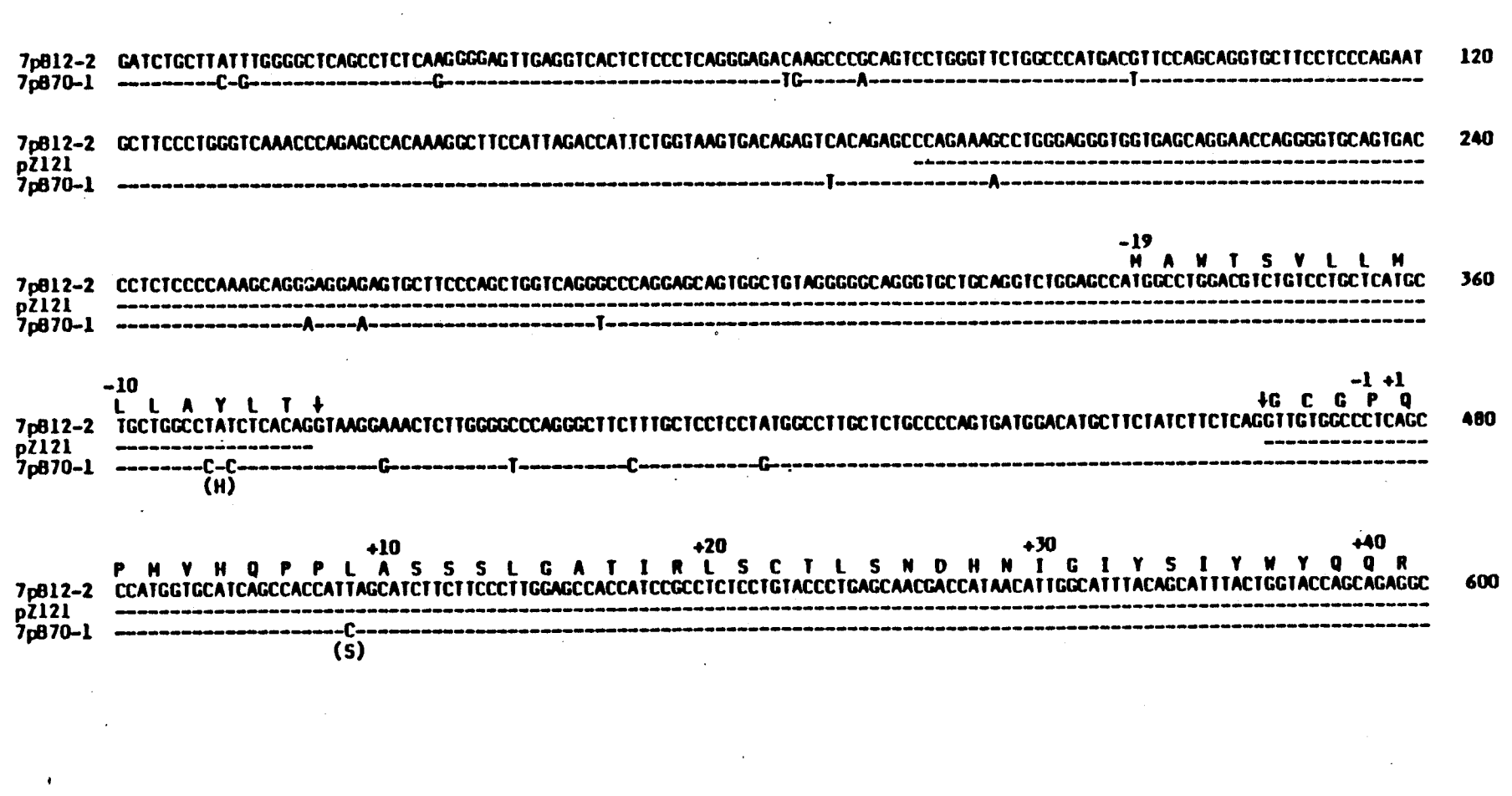

FIG. 22 Nucleotide sequence and deduced amino acid sequence of the $V_{preB}1$ and $V_{preB}2$ gene. For $V_{preB}1$ nucleotide sequences of both the genomic form (7pB12-2) as well as of the cDNA (pZ121) are given. The cDNA sequences are identical with the genomic sequences and are, therefore, only indicated by dashes (—) and follows the genomic sequence in numbering. Numbering of amino acid residues starts with −19 as the first position of the leader and proceeds to +1 as the first position of the mature protein. The sequence marked by closed circles (......) shows the poly A addition signal sequence. Arrows (↓) indicate potential splice sites. The asterisk (*) points to the termination codon TAG. DNA sequencing was carried out using the dideoxy chain termination method by subcloning of fragments into M13mp18 and M13mp19 vectors, using a 17-mer universal M13 primer (Amersham). The $V_{preB}2$ nucleotide sequence of the genomic form (7pB70-1) is given. (For a restriction map of 7pB70-1, see FIG. 25). $V_{preB}2$ sequences identical to $V_{preB}1$ sequences are indicated by dashes (—). Wherever the deduced amino acid sequence of $V_{preB}2$ differs from that of $V_{preB}1$ the changed am acid is given in brackets ( ).

Figure 23:
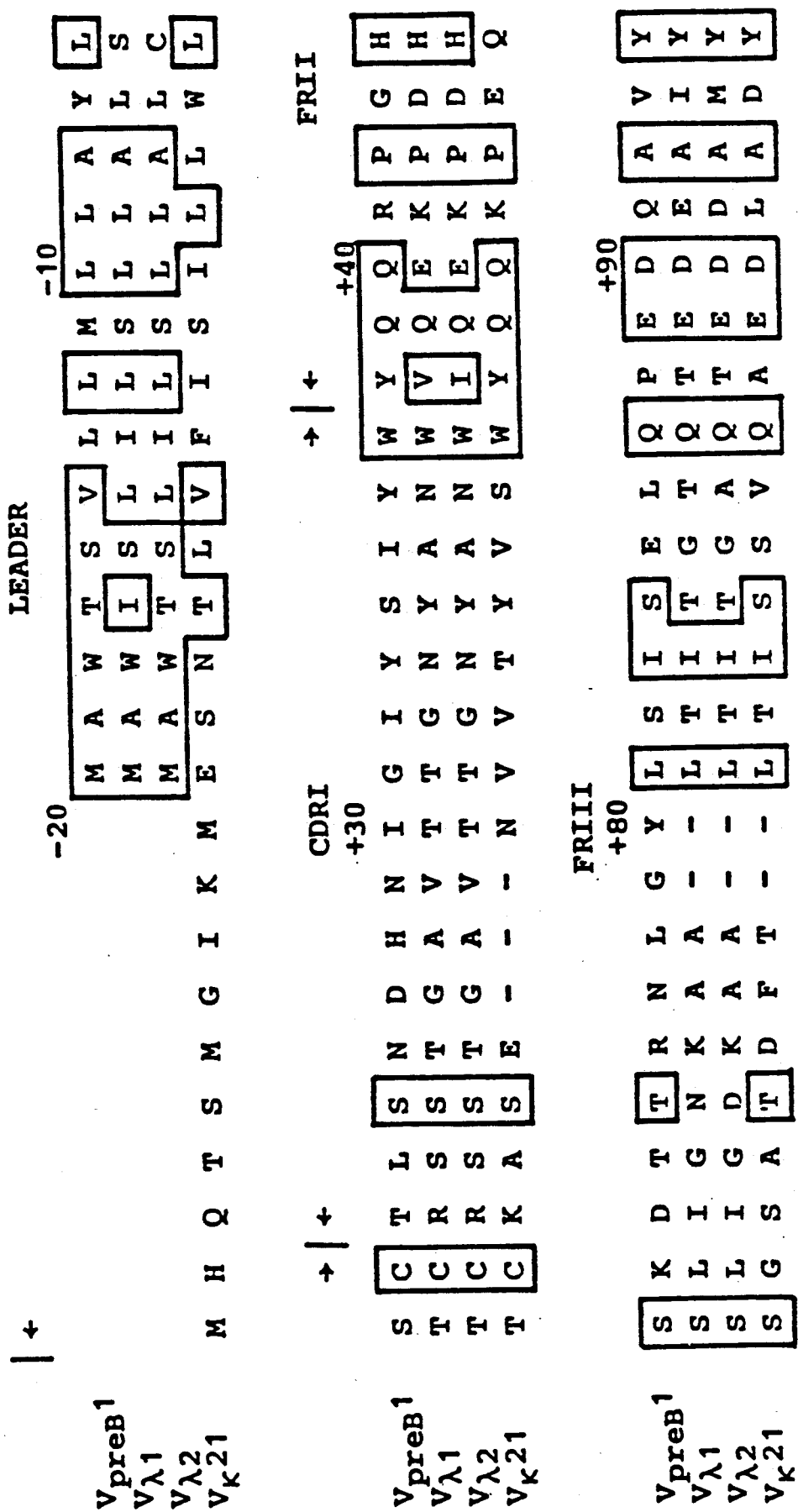

FIG. 23 Alignment of the deduced amino acid sequence of $V_{preB}1$ with sequences of $V_{\lambda1}$, $V_{\lambda2}$ (Tonegawa, et al., Proc. Natl. Acad. Sci. USA, 75 1485-1489, [1978]) and $V_{\kappa}21$ (Fong. et al., Biochem. Biophys. Res. Commun. 90, 832-841, [1979] and Hamlyn, et al., Nucl. Acids, Res. 9, 4485-4494, [1981]). Those residues homologous to $V_{preB}1$ and any of the other sequences are boxed. The numbering of positions follows that given for $V_{preB}1$ in FIG. 22. Leader, CDR I and II and FR I, II and III indicate the locations of the leader, the complementarity-determining and of framework residues found in variable response of L chain (Kabat, et al., supra).

Figure 24:
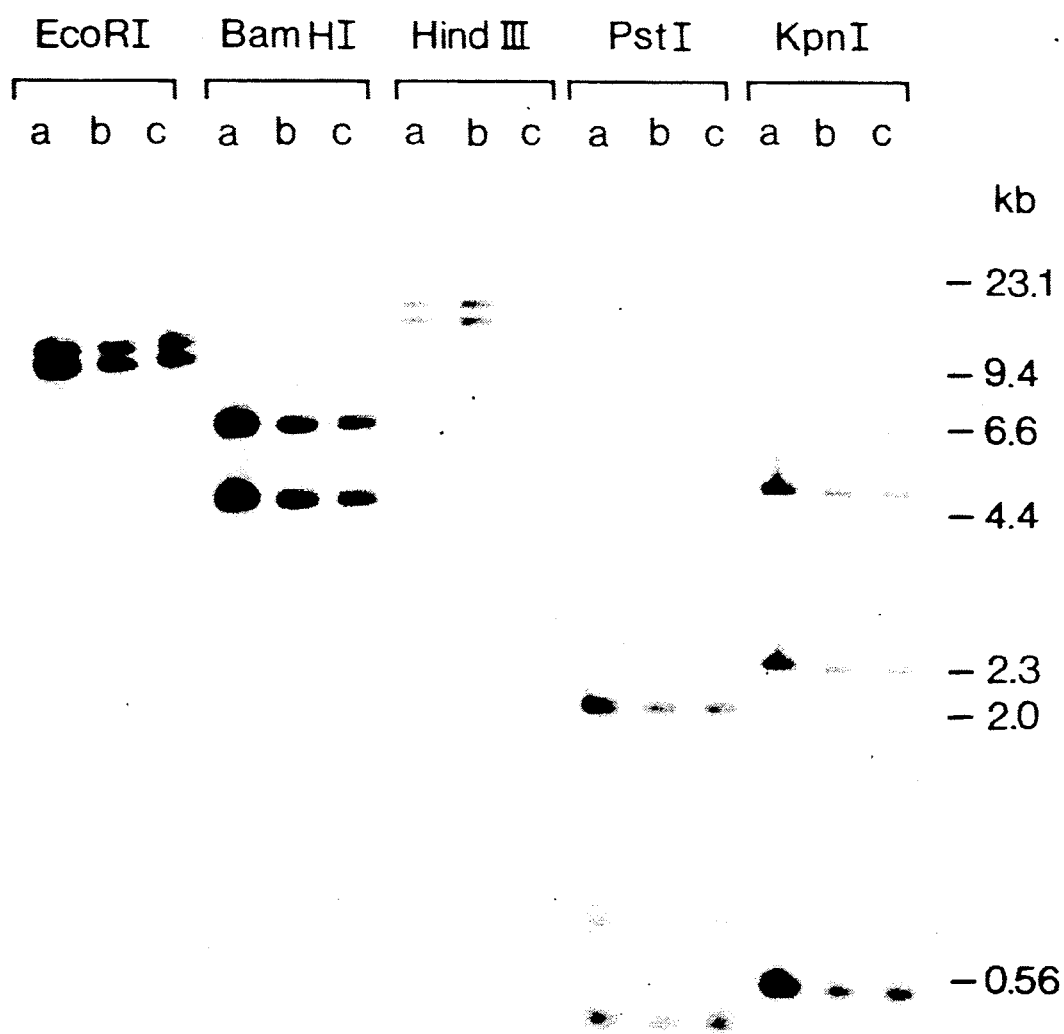

FIG. 24 Southern blot analyses of DNA from DBA/2 liver (a), C57BL/6 liver (b) and from the 70Z/3 (DBA/2×C57BL/6) pre-B lymphoma cell line (c). DNA was digested with the indicated enzymes. 10 µg of DNA fragments were separated by electrophoresis on agarose gels and transferred to the Zeta probe membrane (BioRad) using 0.4N NaOH as transfer buffer (Reed, et al., Nucl. Acids Res. 13, 7207-7221, [1985]). After transfer, the filter was rinsed twice in 2×SSC and dried at 80° C. under vacuum. Prehybridization and hybridization were carried out with 1.5×SSPE (0.27M NaCl 0.015M sodium phosphate, 0.015M EDTA), 1.0% SDS, 0.5% nonfat powdered milk, 0.5 mg/ml carrier salmon sperm DNA and 10% dextran sulfate at 65° C. by using $^{32}P$-oligo labelled insert DNA of cDNA clone pZ 121 as a probe. The filter was washed finally with 0.1×SSC, 0.1% SDS at 65° C.

Figure 25:
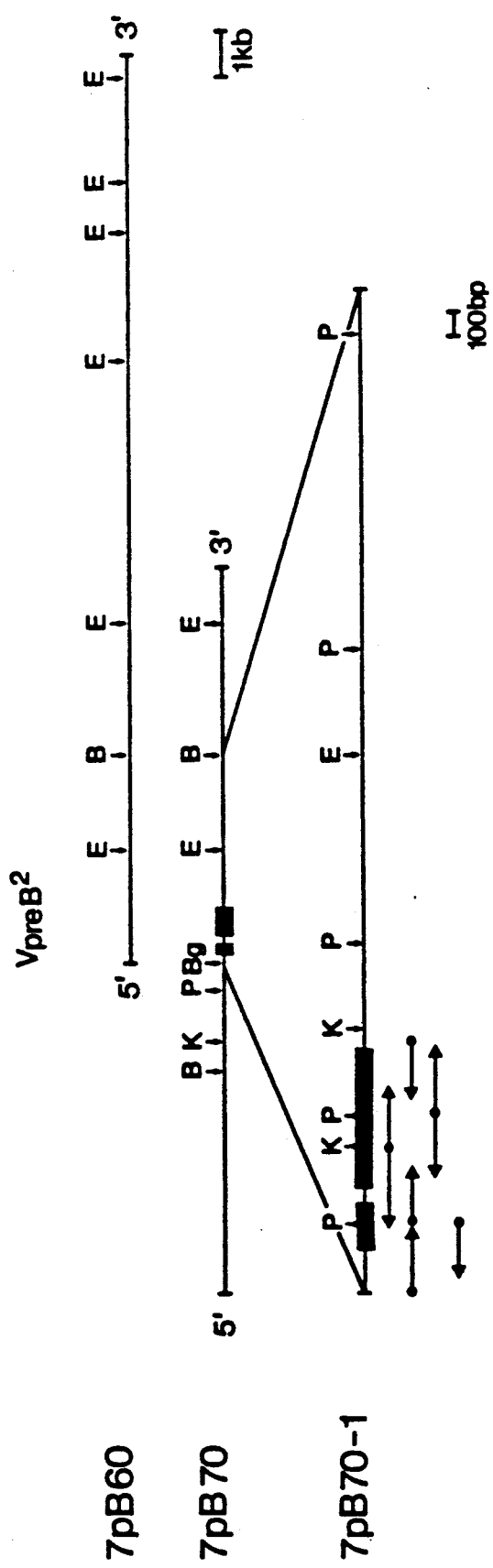

FIG. 25 Restriction map and sequencing strategy of $V_{preB}2$ genomic clones. The restriction maps of two overlapping $V_{preB}2$ genomic clones, 7pB60 and 7pB70 are shown. The 4.4 kb BglII-BamHI fragment (7pB70-1) of 7pB70 was subcloned into pUC-18 and a more detailed restriction map was determined. Restriction sites are abbreviated as in FIG. 13. The sequence is shown in FIG. 22.

Figure 26:
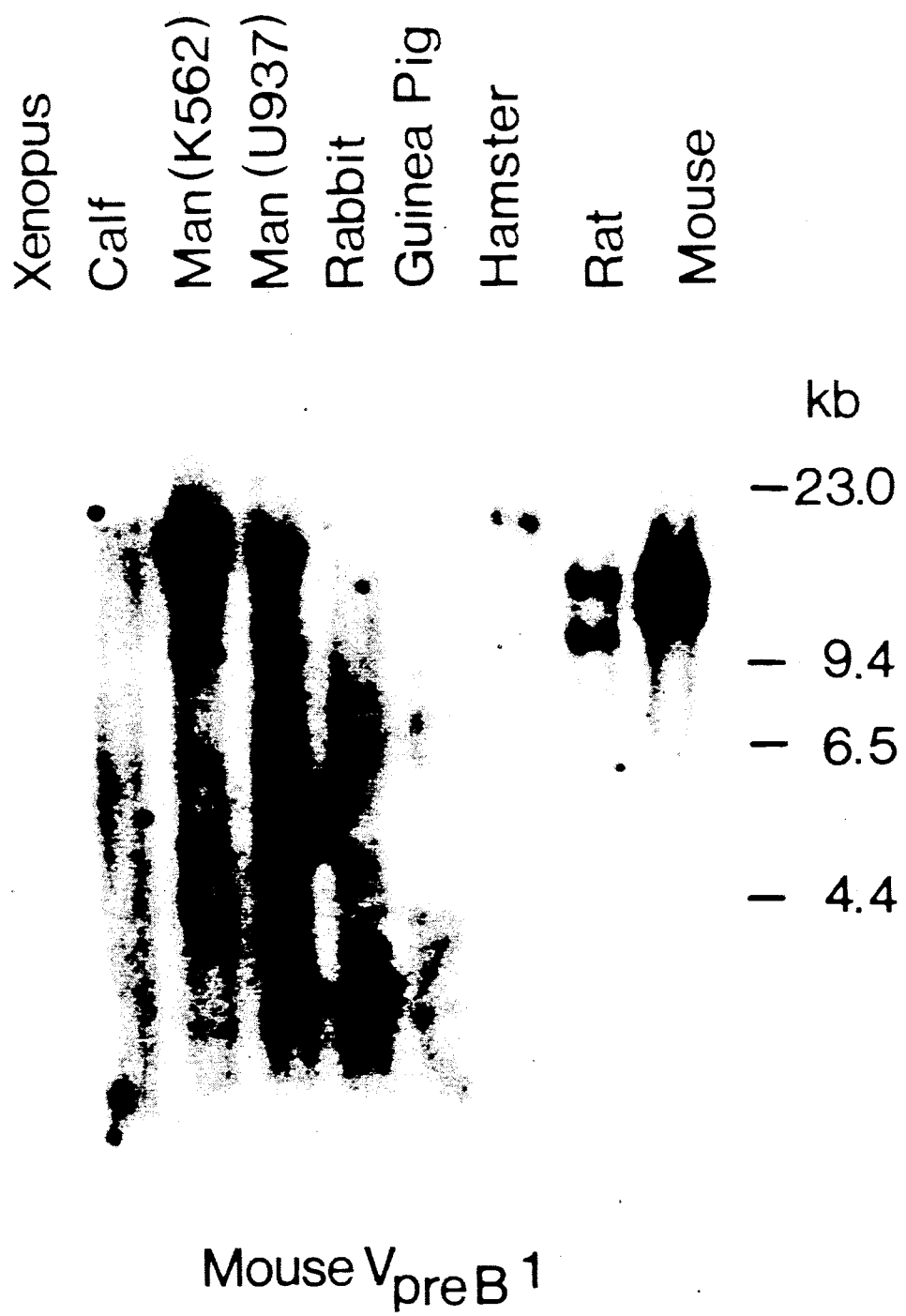

FIG. 26 Southern blot analysis of EcoRI digested DNA from different species.

7 µg digested DNA from liver of rat, hamster, mouse, guinea pig and rabbit, from red blood cells of frog, from calf thymus, and from human cell lines were electrophoretically separated, blotted onto nitrocellulose and hybridized with a $^{32}P$-labelled mouse VpreB1 probe.

Figure 27:
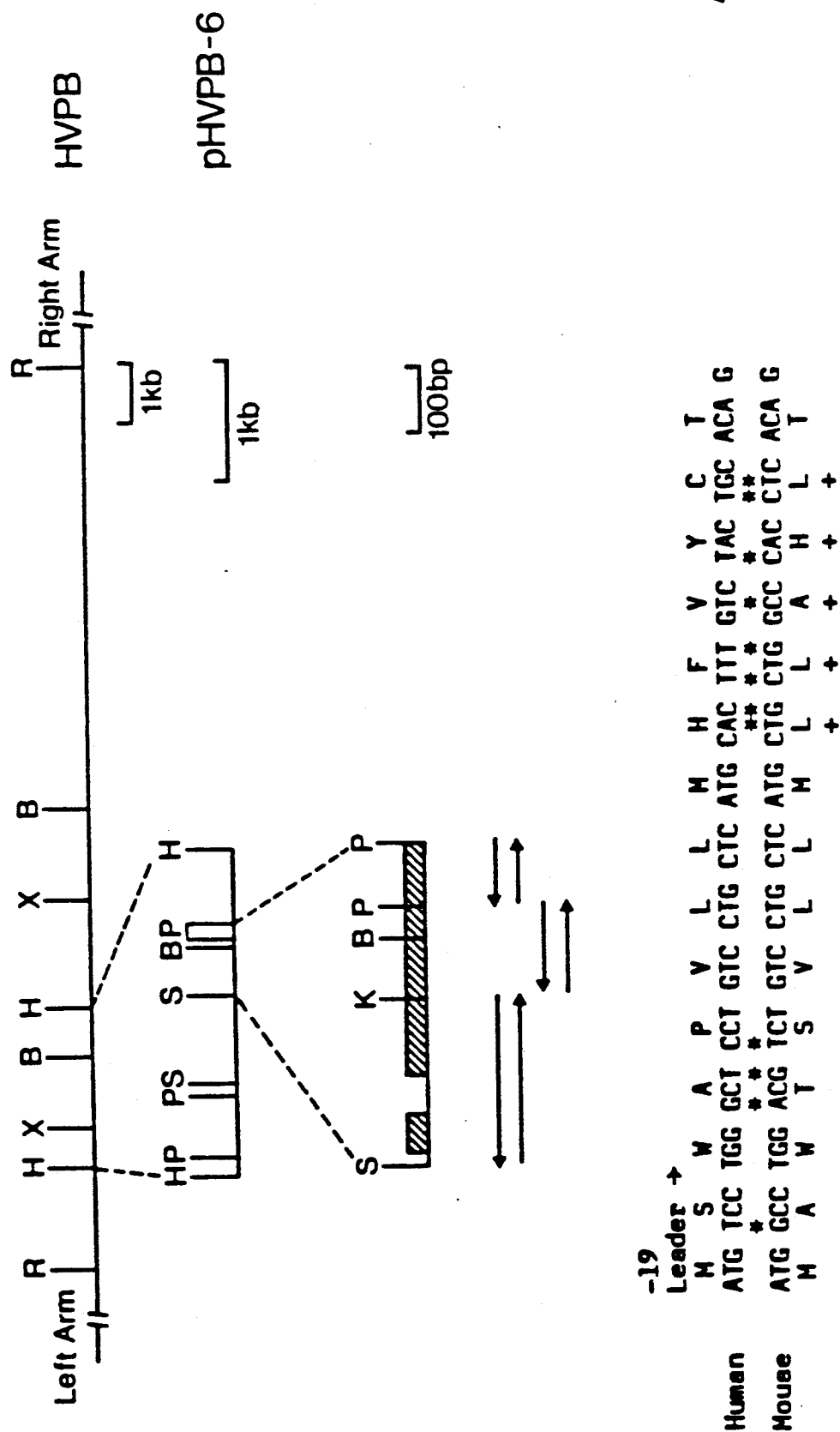

FIG. 27 Restriction map and sequencing strategy for HVPB phage clone and plasmid subclone pHVPB-6 and nucleotide sequence comparison of human VpreB and mouse VpreB1 genes With their deduced amino acid sequences. Restriction enzyme sites are symbolized as: R=EcoRI; B=BamHI; P=PstI; K=KpnI; S=SacI; X=XbaI. Exons I and II are shown as rectangles enclosing slanted lines with the 5' end at the left. Arrows show the direction and length of DNA sequences derived from indicated restriction fragments subcloned into M13. Putative exon structures are based on comparison with the sequence of mouse VpreB1 cDNA. potential splice sites are enclosed in boxes. An asterik (*) indicates nucleotide differences while a plus(+) below the mouse amino acid residues indicates a putative protein difference. A black rectangle indicates the mouse termination codon. Dashes (—) indicate human residues not yet determined. Numbering of deduced amino acid residues starts with −19 as the first position of the leader and proceeds from +1 as the first position of the putative mature protein (top left of each row). Nucleotide residues (right of each sequence row) begin with the A of the initiation codon. Note the 1 base gap in the IVS of the human sequence. Leader, CDRI and II and FRI, II and III indicate the locations of the leader, complementarity determining region, and framework regions typically found in immunoglobulin light chain variable regions (Kabat et al., supra) and following the alignment with V region genes of $V_{preB}1$ and $V_{preB}1$.

Figure 28:
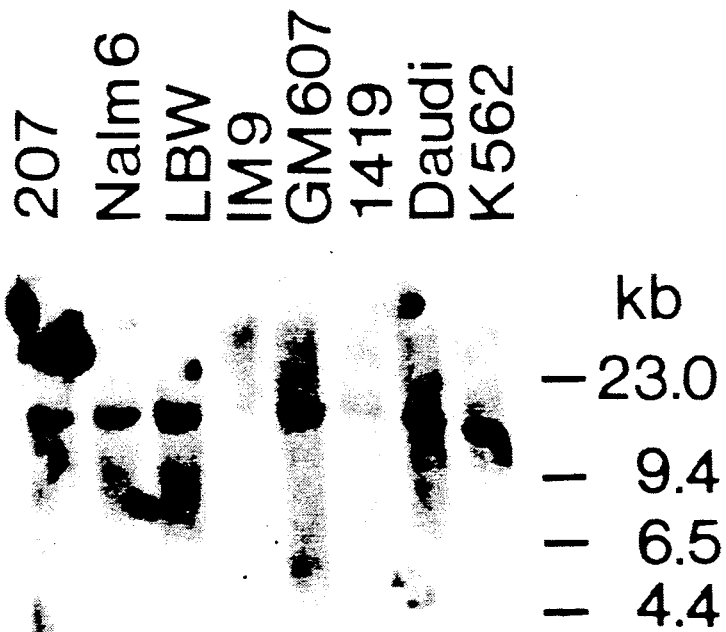

FIG. 28 Southern blot analysis of EcoRI digested DNA from human cell lines.

7 μg digested DNA was applied to a 0.8% agarose gel, electrophoretically separated, then transferred onto nitrocellulose filter. The filter was hybridized with a $^{32}$P-labelled 1.2 kb PstI fragment of pHVPB-6, a 2.7 kb HindIII pUC18 subclone of phage clone HVPB. Washing of the filters was done as described below for the Southern blot analysis shown in FIG. 26. Sizes of hybridizing bands were calculated using HindIII digested phage λ DNA as standards.

Figure 29:
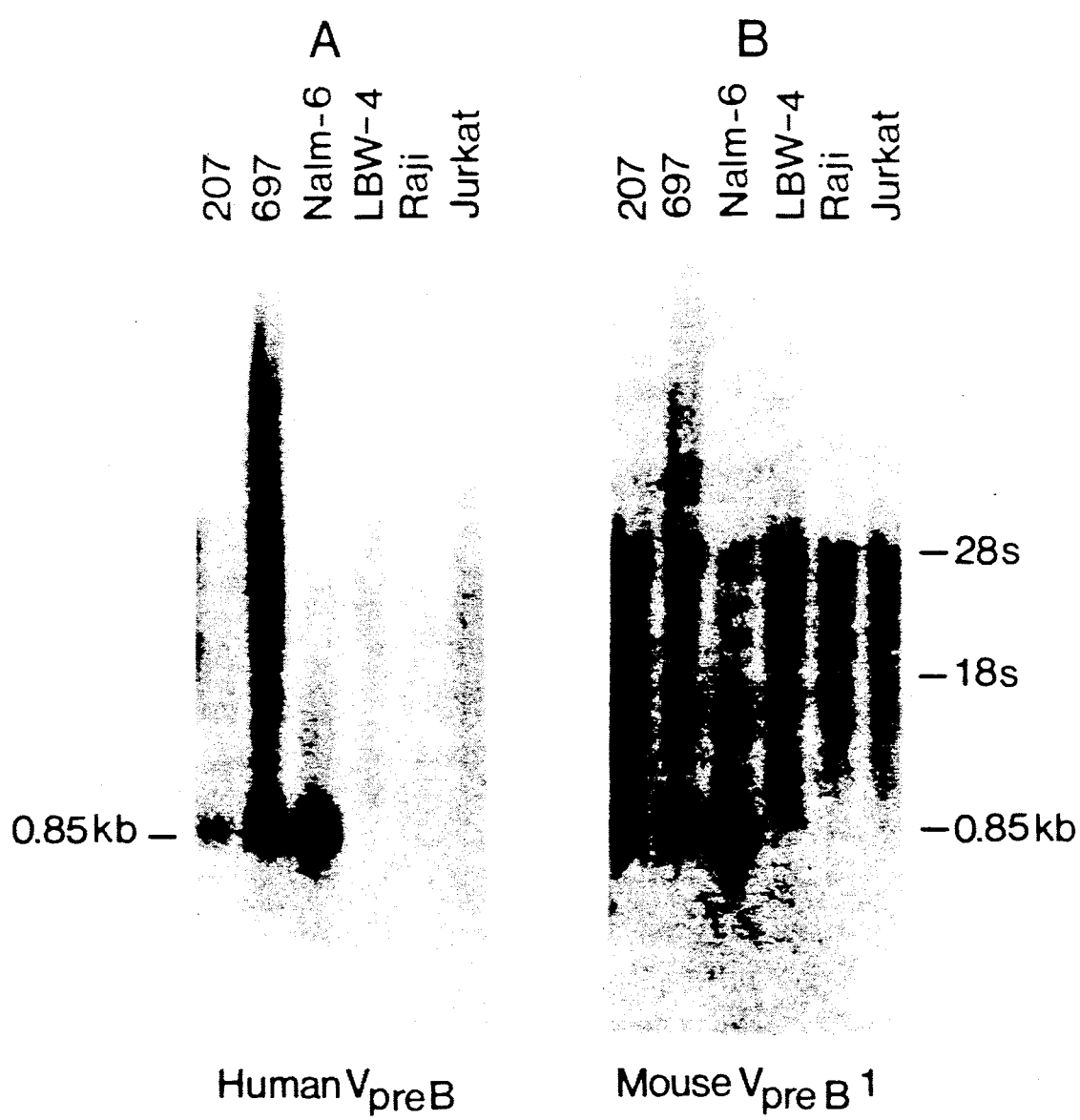

FIG. 29 Northern blot analysis of poly(A)-selected RNA from lymphoid cells.

5 μg poly(A)+ RNA was applied to each lane, electrophoresed and blotted onto activated DPT paper. Identical filters were probed with: (A) a $^{32}$P-labelled 1.2 kb PstI fragment of pHVpB-6 or (B) a $^{32}$P-labelled 560 bp EcoRI-AccI fragment from pZ121. a mouse $V_{preB}1$ cDNA clone. The filter in panel (A) was washed finally in 0.2×SSC. 0.1% SDS at 65° C., then exposed to x-ray film overnight at −80° C. with intensifying screens. The filter in panel (B) was washed finally in 0.2×SSC, 0.1% SDS at 37° C. and exposed as described above. Sizes of hybridizing bands were calculated using RNA molecular weight standards purchased from BRL (Bethesda, Md.).

DETAILED DESCRIPTION OF THE INVENTION

The nucleotide sequences which are selectively expressed in pre-B cells may be identified by subtraction hybridization, i.e., by a method in which nucleotide sequences which are expressed in pre-B cells and in other cells are eliminated and only those sequences are selected which are solely expressed in pre-B cells. More specifically the nucleotide sequence is identified by preparing a cDNA library from poly A containing RNA from a pre-B cell and selecting from that library cDNA clones which hybridize to polysomal poly A containing RNA from a pre-B cell and not to polysomal poly A containing RNA from a different cell which is not a pre-B cell.

Alternatively a nucleotide sequence which is selectively expressed in pre-B cells may be identified by screening a cDNA library with a homologous nucleotide sequence from another species, which nucleotide sequence has been identified by subtraction hybridization as described above. Suitable cDNA libraries are described in the Example. Homologous nucleotide sequences are nucleotide sequences with the same function but originating from different species and with practically a identical nucleotide sequence.

For identifying a first nucleotide sequence selectively expressed in pre-B cells mRNA, preferably microsome-bound polysomal poly A containing RNA can be isolated from pre-B cells by methods known in the art (e.g. Maniatis, et al., supra. pp. 188-209) or as described in the Example. Since it is difficult to isolate a sufficient number of such cells from a mammalian organism, especially from a human organism, a cell line derived from such a subset of the lymphoid cell population may be chosen.

Pre-B cell lines may be easily prepared as described by Rosenberg, et al., Proc. Natl. Acad. Sci. USA 72, 1932-1936, [1975]. The pre-B cell line used in the present invention is the pre-B lymphoma cell line 70Z/3. This cell line is derived from a chemically induced pre-B cell tumor (Paige, et al., J. Immunol. 121, 641-647, [1978]). The cell line has been shown to express μ-heavy (H) chain, but no light (L) chain and, therefore, was identified as a surface Ig-negative pre-B cell (Paige, et al., supra; Sakaguchi, et al., J. Immunol. 125, 2654-2659, [1980]; Perry, et al., Cell 18, 1333-1339, [1979]).

A cDNA library, i.e., a collection of DNA's complementary to the poly A containing RNA from pre-B cells can be prepared by methods known in the art (e.g. Maniatis, et al., supra, pp. 211-246) or as described in the Example. Repeated subtraction hybridization using polysomal poly A containing RNA from a pre-B cell and from a cell which is not a pre-B cell is used to isolate a cDNA clone comprising a nucleotide sequence which is selectively expressed in pre-B cells. Suitable cells which are not pre-B cells are those distinctly different from cells of the early stages of the B cell lineage but related to the latter cells, so that they both express a similar subset of genes. Examples of such cells are lymphoid cells, e.g., T cells, preferably a T cell hybridoma.

In the present invention the T cell hybridoma K62 was used. This T cell line was obtained in the fusion of the thymic lymphoma BW 5147 with an allo-reactive, H-$2^k$-specific helper T cell clone. It is within the scope of the invention to use other T cell lines or any other suitable cell which is not a pre-B cell.

In a preferred embodiment of the present invention the hybridization reactions may be performed at 68° C. for 16-20 hours to achieve a Cot of about 2000 (Britten, et al., Science, 161, 529-540, [1968]). The nonhybridized fraction of cDNA molecules can then be used to construct a phage library according to the method described by Davis, et al., Proc. Natl. Acad. Sci. U.S.A. 81, 2194-2198, [1984]. For a first screening this selected cDNA library may then be tested either with radioactive pre-B cDNA or with radioactive K62 T cell hybridoma cDNA.

In the present invention the frequency of pre-B cell-specific cDNA clones in the T cell cDNA-subtracted library was found to be 14 in 5'000, while there were 10 in 50'000 in the unsubtracted, original 70Z/3 pre-B cDNA library. Clones positive with only the pre-B cDNA but not with the K62 T cell cDNA can be selected and used for a second screening. For that purpose the selected clones are individually grown up. The phage DNA containing the pre-B cell-specific sequences is isolated and after radiolabeling used for hybridization with a panel of RNA preparations from different cell lines of different differentiation lineages at different stages of differentiation.

In the present invention clone pZ 183 was selected from two hundred 70Z/3 specific cDNA clones. The clone contained a 380 nucleotide pair long insert of 70Z/3 cDNA. The selected nucleotide sequence was found to be expressed 1.5 times more than μ-heavy chain-specific mRNA in the 70Z/3 tumor cells. This level of expression is in the range of medium abundance and, thus, is estimated to represent 100–300 mRNA copies per cell (Hastie, et al., Cell 9, 761-774, [1976]). Mature B cells, plasma cells, T cells, macrophages and a variety of cells from other lineages and tissues were found not to express the corresponding gene.

The selected 70Z/3 cDNA sequences or fragments thereof can therefore be used as a probe for the detection of transcripts of genes which are selectively expressed in pre-B cells, for the determination of pre-B cells in a diagnostic test. Such a probe (a negative strand probe) comprises a polynucleotide hybridizing specifically to a transcript wich is selectively expressed in pre-B cells. Said polynucleotide is preferably single stranded and has a nucleotide sequence substantially complementary to that of said transcript.

The length of said complementary nucleotide sequence determines the specificity of the probe. A length of at least about 20 nucleotides is in most cases required for a high enough specificity. Said polynucleotide may be in linear or circular from and may be comprised of two or more individual segments interrupted by non complementary sequences. These non-hybridizable sequences can be linear, or they can be self-complementary and, form hairpin loops. In addition, the complementary region of the probe can be flanked at the 3'- and the 5'-termini by non hybridizable sequences, such as those comprising the DNA or RNA of a vector into which the complementary nucleotide sequence had been inserted for amplification. A polynucleotide having the same nucleotide sequence as the transcript (a positive strand probe) may be used as negative control.

Large amounts of the polynucleotide used for the probe can be obtained by chemical synthesis using conventional polynucleotide synthesis procedures, preferably on a solid phase support by the triester or phosphite method (for a review see e.g. Kiefer, et al., Immunol. Methods 3, 69-83, [1985]) or by cloning said polynucleotide into a suitable replicable microbial vector, transforming said vector into a suitable host and culturing the host under conditions permitting production of multiple copies of the cloned polynucleotide. Suitable vector/host-systems are described in the Example. Preferably the bacteriophage M13 vector system (Messing, Methods in Enzymol. 101, 20-78, [1983]) is used since in that system directly single stranded polynucleotides can be prepared.

Alternatively large amounts of the polynucleotide used for the probe can be obtained by inserting a complementary polynucleotide into a vector containing a very active transcription promoter such as the *Salmonella typhimurium* bacteriophage SP6 transcription promoter (Green, et al., Cell 32, 681-694, [1983]) and producing multiple RNA copies which can be used for the probe. The polynuleotide may contain modified nucleotides.

For use in a diagnostic test a suitable label has to be incorporated into the probe. Suitable labels include but are not limited to radioactive labels, fluorescent labels, enzyme labels and other labels generally known in the art. Such labels may be linked covalently or noncovalently to the polynuleotide or to the hybrid formed after contact of the polynucleotide with a transcript which is selectively expressed in pre-B cells. Typical labels and methods which may be used in a diagnostic test to determine whether a cell is a pre-B cell or not are described. e.g., in the following European Patent Applications with the Publication Nos. 139 489 (published May 2, 1985). 144 913 (published Jun. 19, 1985). 144 914 (published Jun. 19, 1985) 146 039 (published Jun. 26, 1985), 146 815 (published Jul. 3, 1985), 149 339 (published Jul. 24, 1985) and 163 220 (published Dec. 12, 1985). Such a diagnostic test may be useful for the clasification of leukemias which may guide therapeutic decisions (Foon, et al., Blood 68, 1-31, [1986]). Further diagnostic test methods are described in the Example (e.g., "in situ" hybridization, Northern-blot).

In the present invention the selected 70Z/3 cDNA sequence hybridized specifically to a 1.2 kb size transcript present in a variety of pre-B cells. No hybridization was found under the same conditions using poly A containing RNA from mature B cells, plasma cells, T cells and other cells which are not from the B cell lineage. The selected 70Z/3 cDNA sequence is 380 nucleotide pairs long. It represents therefore only a partial cDNA of the 1.2 kb long transcript of the gene selectively expressed in pre-B cells.

The selected 70Z/3 cDNA can be used to prepare a full-length cDNA of said pre-B cell transcript. Such a full-length cDNA can again be used as a probe as described above. Preferably a polynucleotide corresponding to a part of the full-length cDNA sequence is used as a probe. The polynucleotide used as a probe is selected in a way that it recognizes sequences or portions thereof which are unrelated to any other nucleotide sequence known to be expressed by B-cells. Such a selection can be done by comparing the sequence of the full-length 70Z/3 cDNA with sequences stored in a gene sequence data bank such as the GenBank TM (supra).

The selected polynucleotide can then be amplified in a manner known in the art, e.g., by cloning said polynucleotide into a replicable microbial vector. Suitable microbial vectors are described by Maniatis et al. (supra, pp. 1-54) and include plasmids and single- as well as double-stranded bacteriophages. After transformation of the replicable microbial vector into a suitable host organisms, said host can be cultured under conditions permitting production of multiple copies of said vector.

Upon incorporation of a label, said vector or a part thereof containing the selected polynucleotide can be used as a probe as described above. Such a probe can also be used to isolate the genomic sequence λ5 encoding the transcript selectively expressed in pre-B cells.

The full-length cDNA of the transcript selectively expressed in pre-B cells or a fragment thereof can be used to prepare a recombinant polypeptide having an amino acid sequence encoded by said transcript. For this purpose the nucleotide sequence of the cloned cDNA is determined by methods known in the art (e.g., Sanger, et al., Proc. Natl. Acad. Sci. USA 74, 5463-5467, [1977]). The nucleotide sequence is then searched for initiation and termination signals. Any long open reading frame may represent a polypeptide which is selectively expressed in pre-B cells.

It is known that extracellular polypeptides are synthesized in a precursor form comprising a signal peptide sequence. Specific peptidases cleave the precursor polypeptide at the signal peptidase recognition site (Perlman, et al., J. Mol. Biol. 167, 391-409, [1983]) to yield the mature polypeptide.

Such a polypeptide or a fragment thereof may be produced by methods known in the art of recombinant DNA technology in that in a first step a DNA sequence coding for the desired polypeptide is brought under the control of a microbial expression control sequence contained on a replicable microbial vector. The resulting expression vector for said polypeptide is inserted into a suitable host organism capable of expressing said polypeptide. Said host organism may be cultured under conditions permitting production of large amounts of polypeptide. The recombinant polypeptide may then be isolated and purified by methods known in the art. Suitable expression control sequences are described in European Patent Application, Publication No. 186 069, published Jul. 2, 1986. Those of skill in the art may select from these expression control sequences those that are most effective for expressing the desired polypeptide without departing from the scope of this invention.

The selection of a particular host for use in this invention is dependent upon a number of factors recognized by the art. These include, for example, compatibility with the chosen expression vector, toxicity of the polypeptide encoded by the hybrid plasmid, ease of recovery of the desired polypeptide, expression characteristics, biosafety and costs. Within these general guidelines, examples of useful bacterial hosts are gram-negative and gram-positive bacteria, especially strains of *E. coli* and *B. subtilis*.

Once the organisms capable of carrying out the expression of the polypeptides of the present invention have been prepared, the process of the invention can be carried out in a variety of ways, depending upon the nature of the construction of the expression vector and upon the growth characteristics of the host. Typically, the host organism will be grown under conditions which are favorable for the production of large quantities of cells. When a large number of cells have accumulated, suitable inducers or derepressors in the growth medium or a temperature-shift cause the control sequence supplied with such DNA sequence to become active, permitting the transcription and translation of the coding sequence.

In the present invention the expression of the DNA fragment encoding the polypeptide is inhibited by the lac repressor. When a large number of cells have accumulated, the gene is derepressed by the addition of isopropyl-β-D-thiogalactopyranoside (IPTG). The polypeptide produced by the recombinant cell can be released by lysing the cell by conventional means well known in the art. The particular means of lysing will depend upon the host cell utilized.

Alternatively a polypeptide encoded by the nucleotide sequence which is selectively expressed in pre-B cells or preferably by fragments thereof can be synthesized by any known conventional procedure for the formation of a peptide linkage between amino acids. Such conventional procedures include, for example, any solution phase procedure permitting a condensation reaction between the free alpha amino group of an amino acid or residue thereof having its carboxylic group or other reactive groups protected and the free primary carboxylic group of another amino acid or residue thereof having its amino group or other reactive groups protected.

The process for synthesizing the polypeptides may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide.

Such conventional procedures for synthesizing the polypeptides of the present invention include for example any solid phase peptide synthesis method. In such a method the synthesis can be carried out by sequentially incorporating the desired amino acid residues one at a time into the growing peptide chain according to the general principles of solid phase methods (Merrifield, J. Am. Chem. Soc. 85, 2149-2154, [1963]; Barany, et al., The peptides, Analysis, Synthesis and Biology, 2, Gross, E. and Meienhofer, J., Eds., Academic Press, 1-284, [1980]).

The polypeptide of the present invention can be purified by known methods, such as by precipitation with ammonium sulfate, dialysis to remove salts (under normal or reduced pressure), gel filtration, preparative flat-bed iso-electric focusing, gel electrophoresis, various chromatographical methods, e.g., high performance liquid chromatography (HPLC), ion exchange chromatography, reverse phase chromatography and affinity chromatography, (e.g., on dye bound carrier or on Sepharose coupled with monoclonal antibodies against said polypeptide) and the like.

The polypeptide of the present invention may form multimers such as dimers, trimers or tetramers or may be present as a fusion polypeptide. Such a fusion polypeptide may be obtained by linking the above mentioned DNA fragment with a DNA sequence selected from a large variety of DNA sequences that encode procaryotic or eucaryotic polypeptides. After expression of the fusion polypeptide encoded by the combined DNA sequences in a suitable host, the fusion polypeptide may be purified by affinity chromatography using a ligand specific for said procaryotic or eucaryotic polypeptide.

In a preferred embodiment the polypeptides of the present invention can be synthesized as a fusion protein of active β-galactosidase and the peptide encoded by the nucleotide sequence selectively expressed in pre-B cells, or by a fragment thereof. Such fusion proteins can be prepared and purified as described by Rüther, et al., EMBO J., 2, 1791-1794, [1983].

The polypeptides of the present invention may form heterodimers via cysteine residues, possibly with immunoglobulin H chains as partners.

Antibodies can be raised against the polypeptides of the present invention in a manner known per se. Suitable host animals for eliciting antibodies include mammals such as rabbits, horses, goats, ginea-pigs, rats, mice, cows, sheep, etc. The resulting antiserum will contain antibodies which will selectively react with and bind to said polypeptides. The antiserum will either be used directly or the specific antibodies will be purified by methods known in the art, e.g., by ammonium sulfate precipitation. The antiserum or the specific antibodies can be used in a well known manner for diagnostic or therapeutic purposes, e.g., antibody mediated cytotoxic reactions as well as for purification purposes (e.g., affinity chromatography).

Alternatively monoclonal antibodies may be used. Such monoclonal antibodies may be prepared based on the method developed by Köhler and Milstein (Nature, 256, 495-497, [1975]).

In a diagnostic assay various methods which are generally known may be employed for the determination if pre-B cells express the above mentioned polypeptides. In one such procedure a lymphocyte preparation is first treated with unlabeled antibody against the polypeptide of the present invention and after washing treated with a labeled antibody against said antibody. After a further washing step the presence or absence of the label is determined. Only pre-B cells are labeled.

Suitable labels are enzymes, e.g., peroxidase, radiolabels or fluorescent labels. When peroxidase is used as the label, the determination is performed with a substrate such as o-phenylenediamine or tetramethyl benzydine.

The methods for the determination of the polypeptides of the present invention described above can be conducted in suitable test kits comprising in a container antibodies elicited by a polypeptide of the present invention and one or more reagents needed to perform the diagnostic assay procedures described above.

Another method for the determination of a polypeptide of the present invention is the so-called "Western Blotting" technique (Towbin, et al., Proc. Nat. Acad. Sci. U.S.A. 76, 4350–4354, [1979]) According to this technique polypeptides isolated from a lymphocyte preparation are separated on an SDS-polyacrylamide gel and then transferred from the gel electrophoretically on to nitrocellulose paper. This nitrocellulose paper is then treated with antibodies to the polypeptide to be tested. After washing, the nitrocellulose paper is then treated with an anti-antibody labeled with peroxidase. The peroxidase is then detected with a suitable substrate such as o-phenylenediamine. Of course other labels like radioactive or fluorescent labels may be used.

Alternatively the polypeptides of the present invention can be used to titrate antibodies against said polypeptide.

in serum from patients having an abnormal proliferation of lymphocytes of the B cell lineage (e.g., a non-T ALL).

A convenient technique for the determination of such antibodies is an enzyme linked immunosorbent assay (ELISA). According to this test a polypeptide of the present invention is adsorbed to a solid phase. Suitable solid phases are organic and inorganic polymers [amyloses, dextrans, natural or modified celluloses, polyacrylamides, agaroses, magnetite, porous glass powder, polyvinylidene fluoride (Kynar TM) and latex], the inner wall of test vessels (test tube, titer plates or cuvettes of glass or artificial material) as well as the surface of solid bodies (rods of glass and artificial material, rods with terminal thickening, rods with terminal lobes or lamellae). Preferably the test is performed in the wells of a microtiterplate. The solid phase is then treated with the sera to be tested. After washing, anti-human IgG labeled with peroxidase is added. The determination of the peroxidase is performed with a corresponding substrate, e.g., with o-phenylenediamine. Also in this procedure the peroxidase can be exchanged by another label, e.g., by a radioactive or fluorescent label.

Furthermore the "Western-Blotting" technique described above may also be used for the determination of antibodies against said polypeptides. In this case a sample of the polypeptide of the present invention is transferred onto nitrocellulose paper. This nitrocellulose paper is then treated with a serum sample to be tested. After washing and treatment with an anti-antibody labeled with peroxidase, the peroxidase is determined by a suitable substrate, e.g., with o-phenylene diamine. As mentioned above other labels like radioactive or fluorescence labels may be used.

Having now generally described this invention, the same will become even better understood by reference to the following Example which is included herein for purpose of illustration only and is not intended to limit the invention.

EXAMPLE

Microsome-bound Polysomal RNA Preparation

Pre-B cells, e.g., 70Z/3 cells (ATCC No. TIB 158), were grown in RPMI-1640 medium containq 2 mM glutamine, 5% heat inactivated fetal calf serum (Gibco), B-mercaptoethanol ($5 \times 10^{-5}$M) streptomycin (100 μg/ml) and penicillin (100 units/ml) in a 10% $CO_2$ atmosphere to a density of $1 \times 10^6$ cells/ml. Before harvesting, the cells were incubated for 15 minutes with cycloheximide (20 μg/ml). Microsome-bound polysomes were prepared as described by Mechler, et al., (J. Cell Biol. 88, 29–36, [1981]).

Briefly, cells were resuspended in 20 volumes of hypotonic buffer, 10 mM Tris-HCl, pH 7.4, 10 mM KCl, 1.5 mM $MgCl_2$, 10 mM vanadium ribonucleoside complex, 20 μg/ml cycloheximide and allowed to swell for 15 minutes on ice. After homogenization by 30 strokes of a tight-fitting (B) Dounce glass homogenizer and centrifugation at $1000 \times g$ for 5 minutes, the cytoplasmic extract was diluted five fold in 2.5M sucrose with TKM buffer (80 mM KCl, 5 mM $MgCl_2$, 50 mM Tris-HCl pH 7.4) and layered over 2 volumes of 2.5M sucrose TKM buffer. Two layers of sucrose TKM buffer were successively added, one with 2.05M sucrose and a second with 1.3M sucrose.

The gradients were centrifuged for 5 hours at 4° C. in a SW27 rotor (Beckman Instruments, Inc.) at 25,000 rpm. Microsomes floating at the interface between the 2.05 and 1.3M sucrose layers were collected, dissolved in 0.5% NP-40 and layered over two layers of 2M sucrose-TKM and 0.5M sucrose-TKM. After centrifugation at 35,000 rpm for 4 hours with a Beckman 60 Ti rotor, the polysomal pellet was dissolved in 10 mM Tris-HCl, pH 7.5, 5 mM EDTA, 0.2% SDS and then extracted with an equal volume of phenol:chloroform:isoamylalcohol (24:24:1).

Poly A containing RNA was prepared by repeated oligo(dT) cellulose chromatography (P-L Pharmacia, Uppsala, Sweden) in the presence of dimethyl sulfoxide as described by Bantle (Anal Biochem. 72, 413–427, [1976]).

Construction of the Selected cDNA Library

A subtracted cDNA library for pre-B cell specific clones was constructed essentially according to the method of Davis et al. (supra). The first cDNA strand was synthesized with 10 μg of microsome-bound polysomal poly A containing RNA from 70Z/3 in 50 mM Tris-HCl, pH 8.3, 6 mM $MgCl_2$, 60 mM NaCl, 20 mM dithiothreitol (DTT), 10 μg/ml of oligo ($dT_{12-18}$), 1 mM of each four deoxyribonucleotides 100 μCi of $^{32}$P-dCTP (~3000 Ci/mmol), 60 units/ml of placental ribonuclease inhibitor 100 μg/ml of actinomycin D and 100 units of AMV reverse transcriptase (Stehlin, Co., Basle, Switzerland) at 40° C. for 2 hours.

After RNA hydrolysis, hybridization reactions were performed in 0.5M phosphate buffer, 5 mM EDTA, 0.1% lithium laurylsulfate with twenty times excess amount of polysomal poly A containing RNA from a T cell hybridoma, e.g., from the T cell hybridoma K62 at 68° C. for 16–20 hours to achieve a Cot of 2000. The single-stranded fraction after hydroxylapatite (Bio-Rad Laboratories, Richmond, CA, USA) chromatography in 0.12M phosphate buffer, 0.1% lithium laurylsulfate, 5 mM EDTA at 65° C. was re-subtracted in the same conditions as above.

The enriched single stranded cDNA obtained by these procedures (1.75% of the starting amount of cDNA) was made double stranded by the Klenow reaction in 50 mM Hepes-KOH, pH 6.9, 70 mM KCl, 20 mM $MgCl_2$, 10 mM DTT, 50 µg/ml bovine serum albumin, 0.5 mM of each deoxyribonucleotides, and 300 units/ml of Klenow fragment of DNA polymerase I (Stehlin.) at 12° C. for 20 hours and followed by the reverse transcriptase reaction in 0.1M Tris-HCl, pH 8.3, 140 mM KCl, 10 mM $MgCl_2$, 30 mM β-mercaptoethanol, 1 mM of each of the four deoxyribonucleotides and 800 units of AMV reverse transcriptase at 42° C. for 1 hour.

After removal of the hairpin loop with S1 nuclease (P-L Pharmacia), the cDNA was methylated with EcoRI methylase (New England Bio-Labs) and the ends were filled in with T4 polymerase (P-L Pharmacia). EcoRI linkers (New England Bio-Labs) were ligated to both ends by the T4 ligase (Stehlin) reaction with 15% polyethylene glycol 6000 at 12° C. for 16 hours and were digested with EcoRI. After the digestion, the cDNA preparation was purified from the digestion product by passage through a column of Bio-Gel A15M, 100–200 mesh (Bio-Rad). Samples (~30 ng) were ligated to 3 µg λgtll DNA (ATCC No. 37194) that had been cut with EcoRI and treated with calf intestinal phosphatase. Ligated samples were packaged into phage (Young, et al., Proc. Natl. Acad. Sci. USA 80, 1194–1198, [1983]) and plated onto E. coli Y 1088 (ATCC No. 37195). Approximately $5 \times 10^4$ total recombinants were obtained.

Differential Hybridization of Recombinant Clones With Radioactive B Cell and T Cell cDNAs Recominant phage clones were plated onto agar plates (Maniatis, et al., pp 68–73) with ampicillin (25 µg/ml) and transferred to nitrocellulose filter as described by Benton, et al. (Science 196, 180–182, [1977]). The duplicate filters were screened with radioactive cDNA probes from the mRNA of either the pre-B cell or the T cell hybridoma used to construct the selected cDNA library. Radioactive cDNA probes were synthesized from each mRNA preparation by the AMV reverse transcriptase reaction with the random primer of oligodeoxyribonucleotide mixtures produced from calf thymus DNA (P-L Pharmacia).

Prehybridization and hybridization were performed in 5×SSPE (750 mM NaCl, 50 mM $NaH_2PO_4$, 5 mM EDTA; pH 7,4), 5×Denhardt's solution (Maniatis et al., supra, p. 327), 1% SDS, 1 µg/ml tRNA from E. coli, 1 µg/ml poly(A), 100 µg/ml of denatured salmon sperm DNA at 68° C. and the filters were washed finally with 0.1×SSC (1×SSC=standard saline citrate=150 mM NaCl, 15 mM trisodium citrate, pH 7,0), 1% SDS at 65° C. The clones which showed positive after 7 days of exposure with intensifying screen at −70° C. were re-screened with both probes. 200 individual phage clones were selected by this procedure out of 50,000 clones.

For a second screening these clones were then individually grown up and the DNA was extracted by a method described by Yamamoto, et al., Virology 40, 734–744, [1970]. EcoRI digested insert fragments from phage clone DNA were separated by electrophoresis through a 1% low melting point agarose gel, and radiolabeled with $^{32}$P-dATP by the Klenow fragment reaction with the random hexanucleotide primers from calf thymus DNA (Feinberg, et al., Anal. Biochem. 137, 266–267, [1984]).

One radiolabeled insert DNA fragment designated pZ 183 was selected and used for hybridization with a panel of RNA preparations from various cells to show that the insert DNA fragment hybridizes selectively to poly A containing RNA from pre-B cells. Preferably, different cell lines of different lineages at different stages of differentiation are used. These cell lines are considered to be "frozen" at a certain stage of normal cell development and, thus, represent the phenotype of these normal counterparts.

Figure 1:
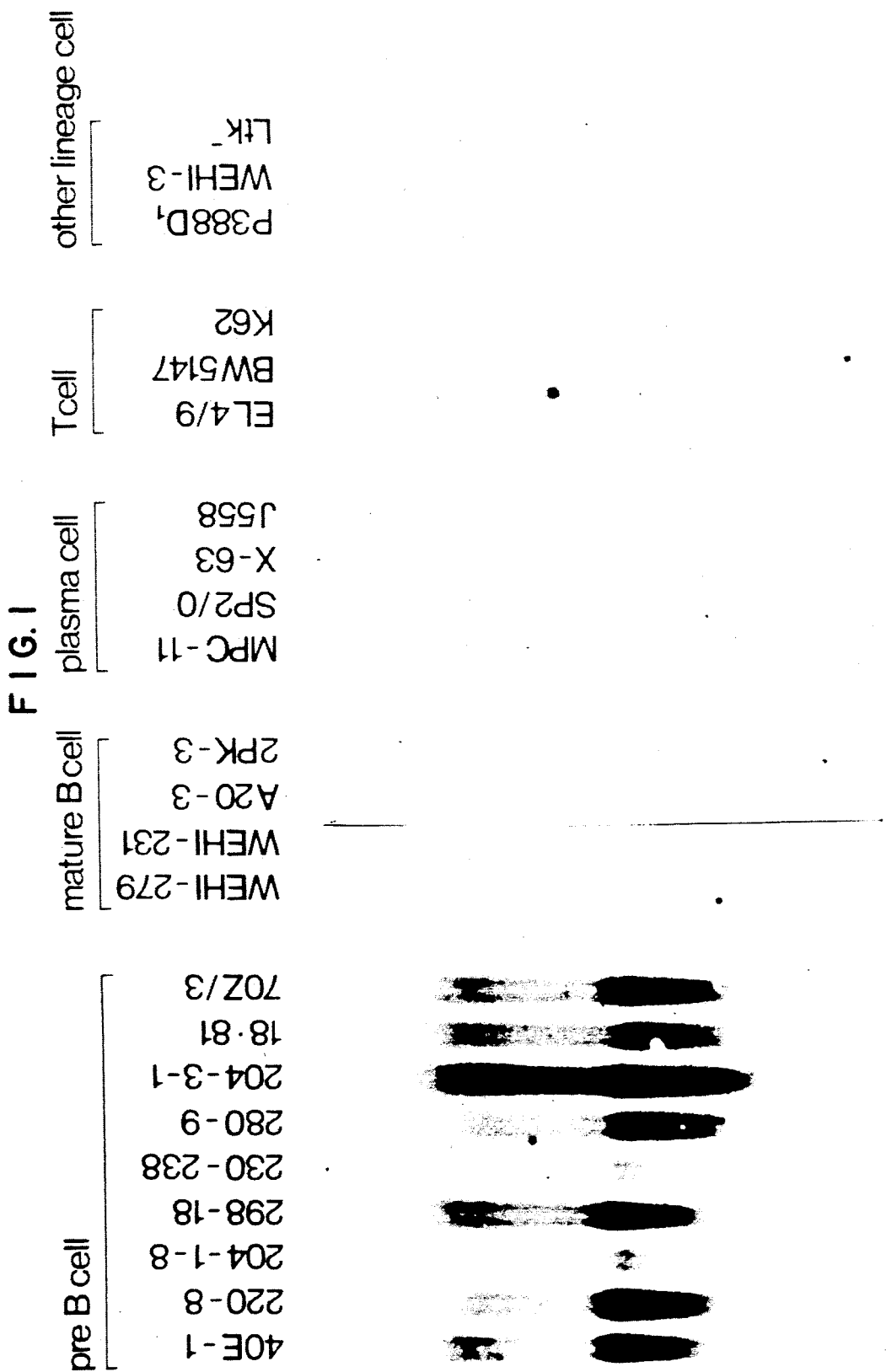
FIG. 1 Expression of pZ 183 transcripts in cell lines representing different stages of the B cell lineage and in cell lines of other lineages. Only pre-B cells show expression of pZ 183 transcripts.
Figure 2:
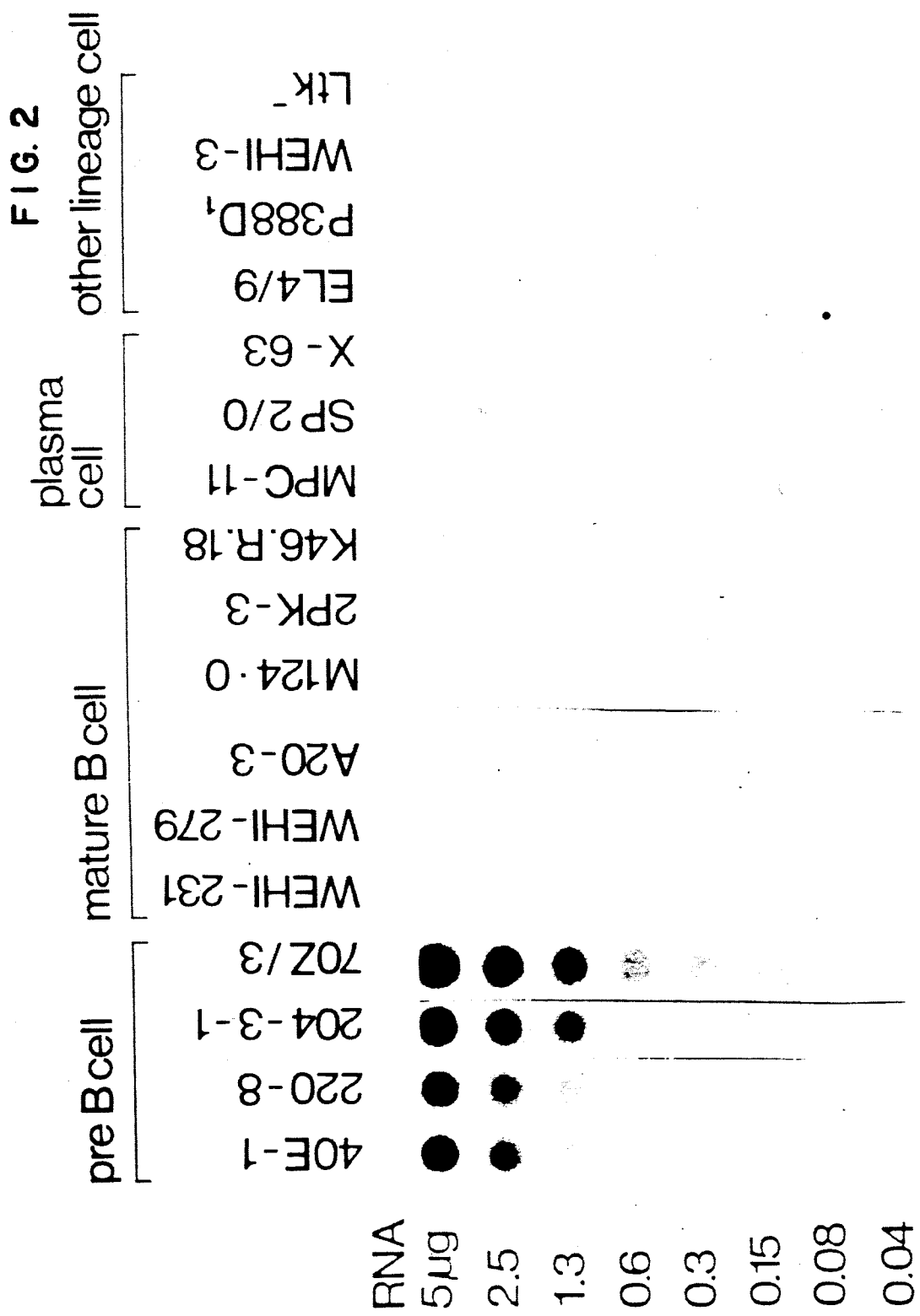
FIG. 2 Quantitative dot blot analysis of pZ 183 transcripts in different cell lines. Such transcripts were only found in pre-B cells but not in mature B cells, plasma cells and not in various non-B lineage cells.

A large variety of such cell lines are known to one skilled in the art and include the cell lines indicated in FIG. 1 and FIG. 2. Besides the desirability that at least one cell line selected is a pre-B cell line, a mature B cell line, a plasma cell line, a T cell line and a non-T/non B-cell line, none of the specific cell lines mentioned is indispensable. Suitable cell lines are, e.g., the pre-B cell line 70Z/3 (ATCC No. TIB 158) or any other pre-B cell line, e.g., as obtained by in vitro transformation of lymphoid cells by Abelson murine leukemia virus (Rosenberg, et al., supra). Examples of mature B cell lines are WEHI-231 (deposited at the European Collection of Animal Cell Cultures [ECACC], PHLS Centre for Applied Microbiology and Research, Porton Down, Salisbury, SP4 OJG. U.K. its accession number being ECACC No. 85022107). A 20-3 (ATCC No. TIB 208) and 2PK-3 (ATCC No. TIB 203). Examples of plasma cells are MPC-11 (ATCC No. CCL 167), SP2/0 (identical with SP2-0-Ag14, ECACC No. 85072401), X63 (identical with P3X63Ag8. ATCC No. TIB 9) and J558 (ATCC No. TIB 6). Examples of T cell lines are EL 4/9 (identical with EL4 ATCC No. TIB 39), BW5147 (ATCC No. TIB 47) and K62. Examples of other lineage cells are p388DI (identical with P388.DI, ECACC No. 85011439) and WEHI-3 (ATCC No. TIB 68). Again none of the above listed cell lines is indispensable for performing the invention.

Those of skill in the art may select other suitable cell lines from the large number of lymphoid cell lines which are known or which may be produced and characterized (e.g., by surface markers or by the rearrangement pattern of their immunoglobulin genes) by methods known in the art. Cell lines are preferred since they provide large amounts of homogenous cells as a source of genes expressed in a lineage- and differentiation-specific manner.

Total cytoplasmic RNA (30 µg) from the cell lines selected was electrophoresed on 1.2% agarose/formaldehyde gel, transferred to nitrocellulose filter, and hybridized with the radioactive probe pZ 183. After hybridization the filters were washed with 0.2×SSC, 1% SDS at 65° C. and then exposed to film in the presence of intensifying screen at −70° C. for 72 hours (so-called Northern blot, Alwine, et al., Proc. Natl. Acad. Sci. 74, 5350–5354, [1977]).

The results in FIG. 1 show that pZ 183 sequences are transcribed preferentially in the cell lines of the precursor B cell stages, including $c\mu^+$, $sIg^-$ pre-B, 28C-9, 204-3-1, 18-81, 70Z/3 as well as $c\mu^-$, $sIg^-$ progenitor cells, 40E-1, 220-B, 204-1-8, 230-238. All of such cells tested proved to be pZ 183 positive (FIG. 1 and Table I). On the other hand pZ 183 transcripts are not detected in early mature B cells ($sIgM^+$), e.g., WEHI-231; intermediate mature B cells ($sIgM^+$, $sIgD^+$), e.g., WEHI-279; pre-secreting B cells ($sIgD^+$). e.g., 2PK-3 or plasma blasts e.g. SP2/0. MPC-11, X-63 or J558. pZ 183 transcripts are also not detected in cells of T lineages, e.g., BW5147, EL4 or K62; in monocytes, P388D1, WEHI-3 and in a fibroblast cell line, Ltk⁻.

These data further suggest that pZ 183 sequences are only transcribed at the pre-B cell stage of B cell differentiation. In this pattern of differentiation expression of pZ 183 is similar, but not identical to the expression of the surface antigen detected by the monoclonal antibody AA4 (McKearn, et al., supra). Exceptions to this rule are the cell lines 2PK-3 and P388.DI, which are pZ 183 negative but AA4 positive.

Expression of pZ 183 Sequences in Pre-B Cells at Various Stages of Ig-gene Rearrangements A set of Abelson-virus (A-MuLV) transformed pre-B cell lines exists that are "frozen" at different stages of Ig gene rearrangements (Alt, et al., supra; Yancopoulos, et al., Nature 311, 727–733, [1984]). Differential expression of pre-B cell-associated surface antigens characterized by the monoclonal antibodies 14.8, AA4 and GF1 has been observed with these cell lines (McKearn, et al., Eur. J. Immunol. 15, 295–298, [1985]). B cell precursors with fully rearranged ($V_H \rightarrow D_H \rightarrow J_H$) or with incompletely rearranged ($D_H \rightarrow J_H$) IgH genes both express in general the B 220 surface glycoprotein and the antigen recognized by the monoclonal antibody AA4, whereas some of these cells do not express an antigen recognized by the monoclonal antibody GF1. Therefore, pZ 183 expression was probed with RNA extracted from A-MuLV transformed pre-B cell clones obtained from different strains of mice, from different organs at different times of gestation, characterized by different stages of rearrangements of IgH and L chain genes and by other surface markers (listed in Table I).

Results in FIG. 1 show that pZ 183 is expressed in all pre-B cell lines, as they originate from pre-B cells of day 13–14 (40E-1) day 17–19 of gestation in fetal liver (28C-9) and adult bone marrow (220-8 204-1-8 230-238 204-3-1 18-81). It is, of course, also expressed in the 70Z/3 pre-B cell line obtained by chemical carcinogenesis from which the cDNA library was made. pZ 183 is expressed in lines which have only $D_H \rightarrow J_H$ rearranged, clones which have $V_H \rightarrow D_H \rightarrow J_H$ rearranged (28C-9, 220-8, 18-81, 70Z/3, 204-1-8, 230-238), clones which either express (cμ+) (28C-9, 204-3-1, 18-81, 70Z/3) or do not express (cμ-) heavy chain proteins (40E-1, 220-8, 204-1-8, 230-238), and clones which either express (40E-1, 204-1-8, 230-238, 28C-9, 204-3-1, 70Z/3) or do not express the GF1 surface antigen (204-18, 18-81). Again the cell lines mentioned are a selection of a wide variety of other cells which may be used for the same purpose.

RNA Dot Blot and Northern Blot Analysis

The level of expression of pZ 183-specific transcripts was estimated by RNA dot blot analysis of serially diluted cytoplasmic RNA samples from different cell lines (FIG. 2).

Preparation of cytoplasmic RNA for RNA dot blot analysis and transfer to nitrocellulose filters were done as described by White, et al. (J. Biol. Chem. 257, 8569–8572, [1982]). pZ 183 DNA was used as a hybridization probe. Prehybridization, hybridization and washing were the same as in the experiments of FIG. 1. Only pre-B cells show expression of pZ 183 transcripts. The level of expression was similar in all pre-B cells tested.

The size of the pZ 183-specific transcript(s) was analyzed in RNA prepared from either unstimulated or

TABLE I

Cell Lines Tested For the Expression of pZ 183 Transcripts

| Differentiation type | Name of clone | Transformation (induction) | Tissue source | Strain | IgH-IgL genes protein | | IgH-IgL chain | Phenotype[e] | | | |
|---|---|---|---|---|---|---|---|---|---|---|---|
| | | | | | | | | B220 | sIgM | AA4 | GF1 |
| Pre-B cell | 40E-1 | A-MuLV[a] | d 13-14 FL[b] | BALB/c | R[c] | E[d] | — — | + | — | + | + |
| | 220-8 | A-MuLV | Adult BM | BALB/c | R | E | — — | + | — | + | + |
| | 204-1-8 | A-MuLV | Adult BM | BALB/c | R | E | — — | + | — | + | — |
| | 298-18 | A-MuLV | Adult BM | BALB/c | R | E | — — | + | — | + | — |
| | 230-238 | A-MuLV | Adult BM | C57Bl/6 | R | E | — — | + | — | + | + |
| | 28C-9 | A-MuLV | d 17-19 FL | BALB/c | R | E | + — | + | — | + | + |
| | 204-3-1 | A-MuLV | Adult BM | BALB/c | R | E | + — | + | — | + | + |
| | 18-81 | A-MuLV | Adult BM | BALB/c | R | R | + — | + | — | + | — |
| | 70Z/3 | Nitrosourea | | (C57Bl/6 × DBA/2)F₁ | R | R | + — | + | — | + | + |
| Mature B cell | WEHI-279 | Radiation | | NZC | | | | + | sIgM sIgD | + | + |
| | WEHI-231 | Mineral oil | | (BALB/c × NZB)F₁ | | | | + | sIgM | — | — |
| | A20-3 | Spontaneous | | BALB/c | | | | N.T.[f] | sIg | N.T. | N.T. |
| | M124.0 | Spontaneous | | BALB/c | | | | N.T. | sIg | N.T. | N.T. |
| | K46.R.18 | Spontaneous | | BALB/c | | | | + | sIgM sIgD | N.T. | N.T. |
| | 2PK-3 | Mineral oil | | BALB/c | | | | — | sIgD | + | + |
| Plasma cell | MPC-11 | Mineral oil | | BALB/c | | | | — | — | — | — |
| | SP2/0 | Hybridoma | | BALB/c | | | | N.T. | N.T. | N.T. | N.T. |
| | X63 | Mineral oil | | BALB/c | | | | N.T. | N.T. | N.T. | N.T. |
| | J558 | Mineral oil | | BALB/c | | | | — | — | — | — |
| T cell | EL4/9 | | | BALB/c | | | | N.T. | N.T. | N.T. | N.T. |
| | BW 5147 | Spontaneous | | AKR/J | | | | N.T. | — | — | — |
| | K62 | Hybridoma | | AKR/J × C57Bl/6 | | | | N.T. | N.T. | N.T. | N.T. |
| Other lineage cell | p388D1 | | | DBA/2 | | | | | | | |
| | WEHI-3 | | | BALB/c | | | | | | | |
| | Ltk⁻ | | | C3H | | | | | | | |

[a]A-MuLV, Abelson murine leukemia virus.
[b]Day 13-14 fetal liver.
[c]R = rearranged in immunoglobulin genes.
[d]E = embryonic configuration in immunoglobulin genes.
[e]Referred from McKearn and Rosenberg, Eur. J. Immunol. 15, 295-298, [1985]
[f]N.T., not tested.

Figure 3:
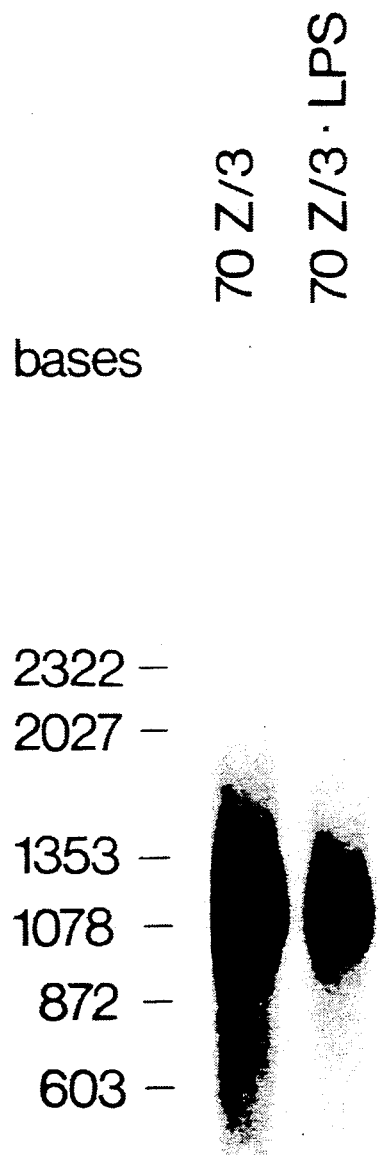
FIG. 3 Northern blot analysis of pZ 183 transcripts in RNA isolated from unstimulated and LPS stimulated 70Z/3 cells. One pZ 183-specific transcript was found, with a size of 1.2 kb (1 kb=1000 nucleotides). LPS stimulation (12 hrs., 10 μg/ml) of 70Z/3 cells showed no effect on the expression of this transcript.

LPS-stimulated 70Z/3 cells, by Northern blot analysis (FIG. 3). Cytoplasmic RNA was isolated (Chirgwin, et al., Biochemistry 18, 5294-5299, [1979]) from 70Z/3 cells cultured with or without LPS (10 µg/ml) for 12 hours. The RNA was enriched for poly A containing RNA by oligo (dT) cellulose chromatography. One to forty micrograms of an RNA sample wee electrophoretically separated in an agarose/formaldehyde gel and transferred to nitrocellulose filters as described (Maniatis et al., supra, pp 382-389). Prehybridization and hybridization were performed as described in the sections of differential hybridization but with 50% formamide at 42° C. The filters were finally washed with 0.2×SSC, 1% SDS at 65° C.

pZ 183-specific RNA from both types of cells was found to be 1.2 kb in size. LPS stimulation of 70Z/3 cells which induces further maturation of these cells so that they express kL chains (Paige, et al., supra; Sakaguchi, et al., supra) does not influence the level of transcription or the size of the pZ 183-specific transcript.

Expression of pZ 183 Sequences in the Cells of Normal Organs and Tissues

Figure 4:
FIG. 4 Northern blot analysis of pZ 183 transcripts in the cells of normal organs and tissues. Only in 70Z/3 cells such transcripts were detected. (a) Northern blot, (b) ethidium bromide stained gel.

RNA was prepared from cells of spleen, thymus, kidney bone marrow, lung, heart, brain and liver. Poly A containing RNA isolated from these organs (5 µg each) and poly A containing RNA from 70Z/3 cells (2 µg) were electrophoretically separated, stained with ethidium bromide (FIG. 4b), transferred to nitrocellulose filter and hybridized to radioactive pZ 183 probe (FIG. 4a). Blots were exposed to X-ray film for 7 days at −70° C. in the presence of an intensifying screen. It is clear from the data presented in FIG. 4 that this analysis yielded no positive signals from RNA of all the organs tested. This indicated that the relative contribution of pre-B cells expressing pZ 183 in all of these organs must be too low in the total mixture of all other cells to be detectable by Northern gel analysis.

Therefore an "in situ" hybridization technique developed for tissue sections and single cells of lymphoid organs (Berger, EMBO J. 5, 85-93, [1986]) was used to probe for expression of pZ 183 sequences in these organs. For this, an insert fragment of pZ 183 of 380 bp was introduced into the M13 phage mpll EcoRI site to obtain a single stranded pZ 183-specific probe which could be used in radiolabeled form in the "in situ" hybridization technique. The M13 vectors are described by Messing, et al., (supra) and by Yanisch-Perron et al. (Gene 33, 103-119, [1985]). The pZ 183-specific sequence was radiolabeled by primer extension DNA synthesis using $^3$H-labeled nucleotides and the labeled pZ 183 sequences, separated from the adjacent M13 sequences, were purified as the single strand probe molecules were, by gel electrophoresis. The positive strand phage DNA and the opposite strand phage DNA were tested by RNA dot hybridization on RNA samples of 70Z/3.

Ten thousand cells were attached to the glass slide, fixed, treated with pronase, prehybridized and hybridized with 10 µl of single strand radiolabeled DNA probe (6500 d.p.m./µl) in prehybridization solution (50% formamide, 0.6M NaCl, 1 mM EDTA, 10 mM Tris-HCl, pH 7.5, 1×Denhardt's solution, 150 µg/ml sonicated salmon sperm DNA, 500 µg/ml tRNA) for 3 days at 35° C. The slides were washed within 24 hours with three to four changes of 50% formamide, 0.6M NaCl, 1 mM EDTA, 10 mM Tris-HCl, pH 7.5. Photographic development of the slides and counting of the grains were done as previously described (Berger, supra).

Figure 5:
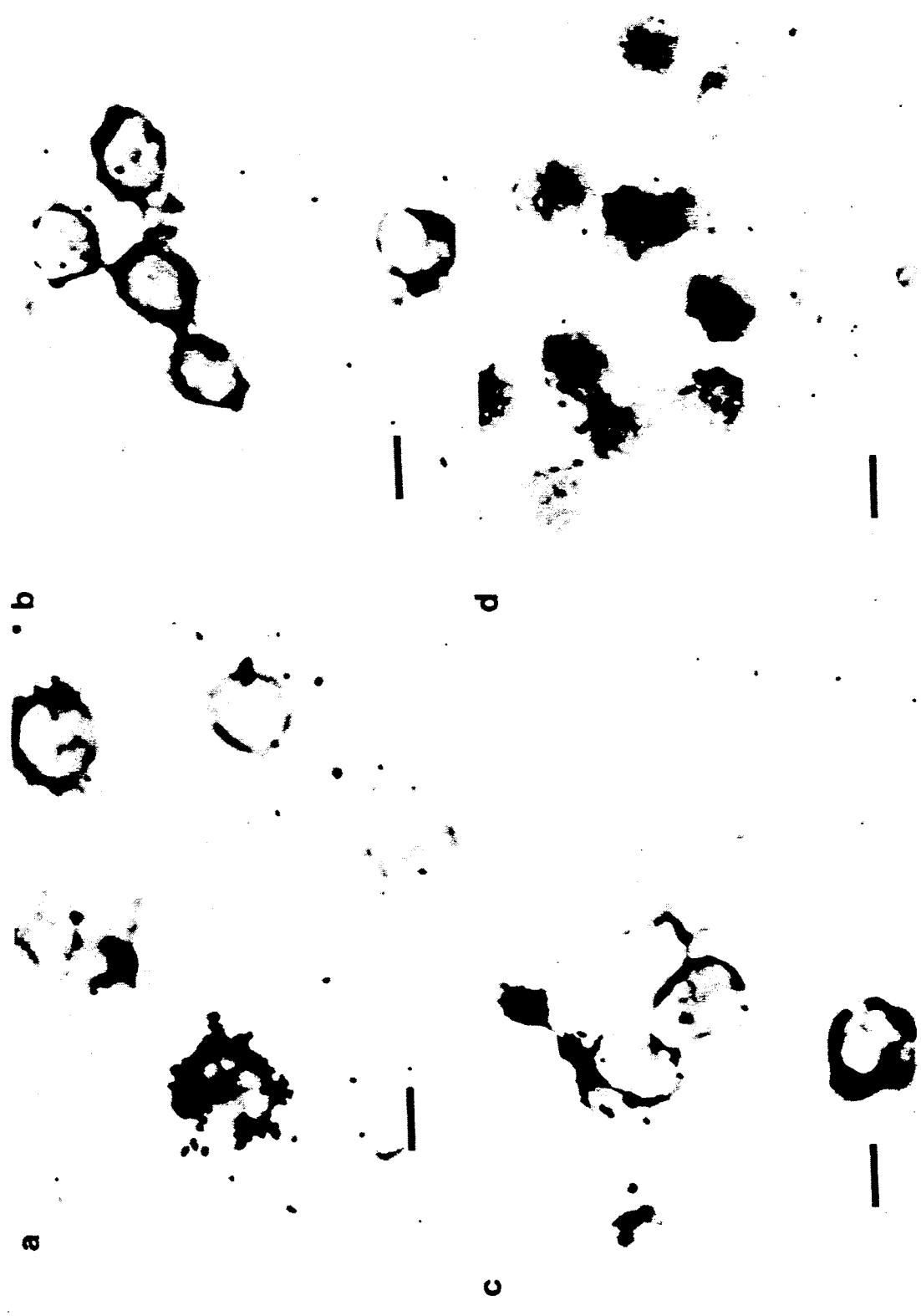
FIG. 5 Detection of pZ 183 specific mRNA molecules in single cells of lymphoid organs by in situ hybridization. Bars 10 μm.
a) Day 15 fetal liver cells hybridized with pZ 183 negative strand probe, pronase digestion 66 μg/ml, exposure time 62 days.
b) As in a) but hybridized with pZ 183 positive strand probe.
c) Adult bone marrow cells hybridized with pZ 183 negative strand probe, pronase digestion 33 μg/ml, exposure time 49 days.
d) Small resting spleen cells hybridized with pZ 183 negative strand probe, pronase digestion 11 μg/ml, exposure time 49 days.

As can be seen in FIG. 5, the radiolabeled pZ 183 probe readily detected specifically hybridizable cells expressing pZ 183-specific RNA within 15 day fetal liver cells (FIG. 5a), and in total adult bone marrow cells (FIG. 5c), but not in small resting spleen cells (FIG. 5d) (more than a thousand cells counted). As one control, 70Z/3 cells were found to be positive. As another control the positive strand probe, as expected, did not label any cells of the fetal liver (FIG. 5b) (more than a thousand cells counted). In fetal liver cells from day 15 of gestation, 2.5% of all cells (13 of 485 counted cells) were found to be pZ 183-positive while at day 16, 4% (8 of 216 counted cells) of all cells were positive. In the adult bone marrow, 1% of cells (6 of 619 counted cells) expressed pZ 183 transcripts.

Finally, the expression of pZ 183 sequences was studied in tissue sections on day 16 fetal liver. Fetal liver organs were snap frozen in liquid nitrogen and prepared as 5 µm thick sections on glass slides. The in situ hybridization was carried out as described above. FIG. 6 shows that the pZ 183 positive cells in fetal liver do not form foci, but are scattered in a diffuse way over large areas of the fetal liver.

Construction of Clone pZ 183-1

Figure 7:
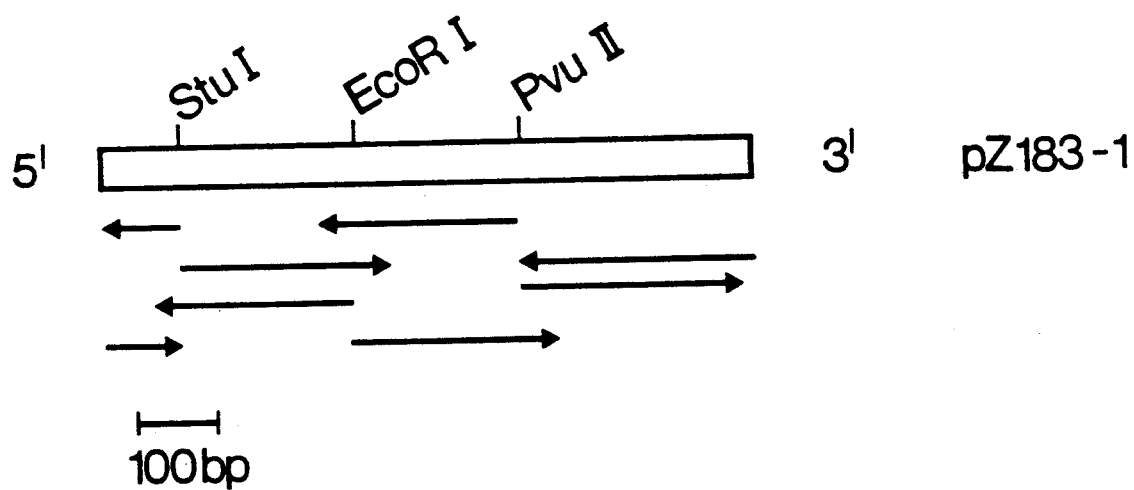
FIG. 7 Restriction enzyme map of the 0.7 kb insert of clone pZ 183-1. The arrows show the length of the fragments used for subcloning into M13 and the direction in which the given fragment was sequenced.

To obtain longer cDNA clones corresponding to the 1.2 kb transcript found in all pre-B cell lines, a new cDNA library was constructed. A poly A containing RNA preparation obtained from 70Z/3 cells by the tailing method (Maniatis, et al., supra, pp. 230-242) was inserted into the pUC-13 vector (Messing et al., supra). The new cDNA library was screened with the 380 nucleotide pair long insert of the cDNA clone pZ 183. Nine cDNA clones were found positive in a total of 50 000 clones. The cDNA clone with the longest i.e., a 0.7 kb insert called pZ 183-1, was sequenced by the dideoxy chain termination method (Sanger, et al., supra). FIG. 7 shows the restriction enzyme sites used for generating the fragments which were used for cloning into M13 phage vector. The arrows indicate the length of the fragments generated and the direction in which the fragments were sequenced.

The nucleotide sequence of the cDNA clone pZ 183-1 is shown in FIG. 8. The 5' to 3' orientation was deduced from the location of the poly A tail and the poly A attachment site (underlined). Nucleotide positions are numbered from the most 5' position of the insert cDNA fragment.

Deduction of the Amino Acid Sequence of the Insert in pZ 183-1

A DNA sequence data bank (GenBank TM, supra) was searched for possible evolutionary relationships of the pZ 183-1 sequence to known DNA sequences. Strong homology was detected for positions 240-554 to the C region nucleotide sequence of $\lambda_1$ L-chains. Equally strong homology was found for the adjacent 5' positions 201-239 to the J segment sequence of $\lambda_1$ L chains (Table II). The reading frame of the $\lambda_1$ L chain J plus C nucleotide sequence was then imposed on the pZ 183-1 sequence as a reading frame. This happened to be reading frame 1 (starting with nucleotide 1) of the sequence shown in FIG. 8.

In this reading frame only two stop codons are found in positions 554 and 594, while reading frame 2 contains eleven (the first in position 9) and reading frame 3 nine (the first in position 101) stop codons. Comparison with the λ₁ L chain nucleotide sequence shows that the first stop codon in frame 1 of the pZ 183-1 sequence is found at the same position where the first, i.e., the functional stop codon of λ₁ L chains is positioned. Reading frame 1 is therefore, the most likely candidate for a translatable sequence.

Figure 9:
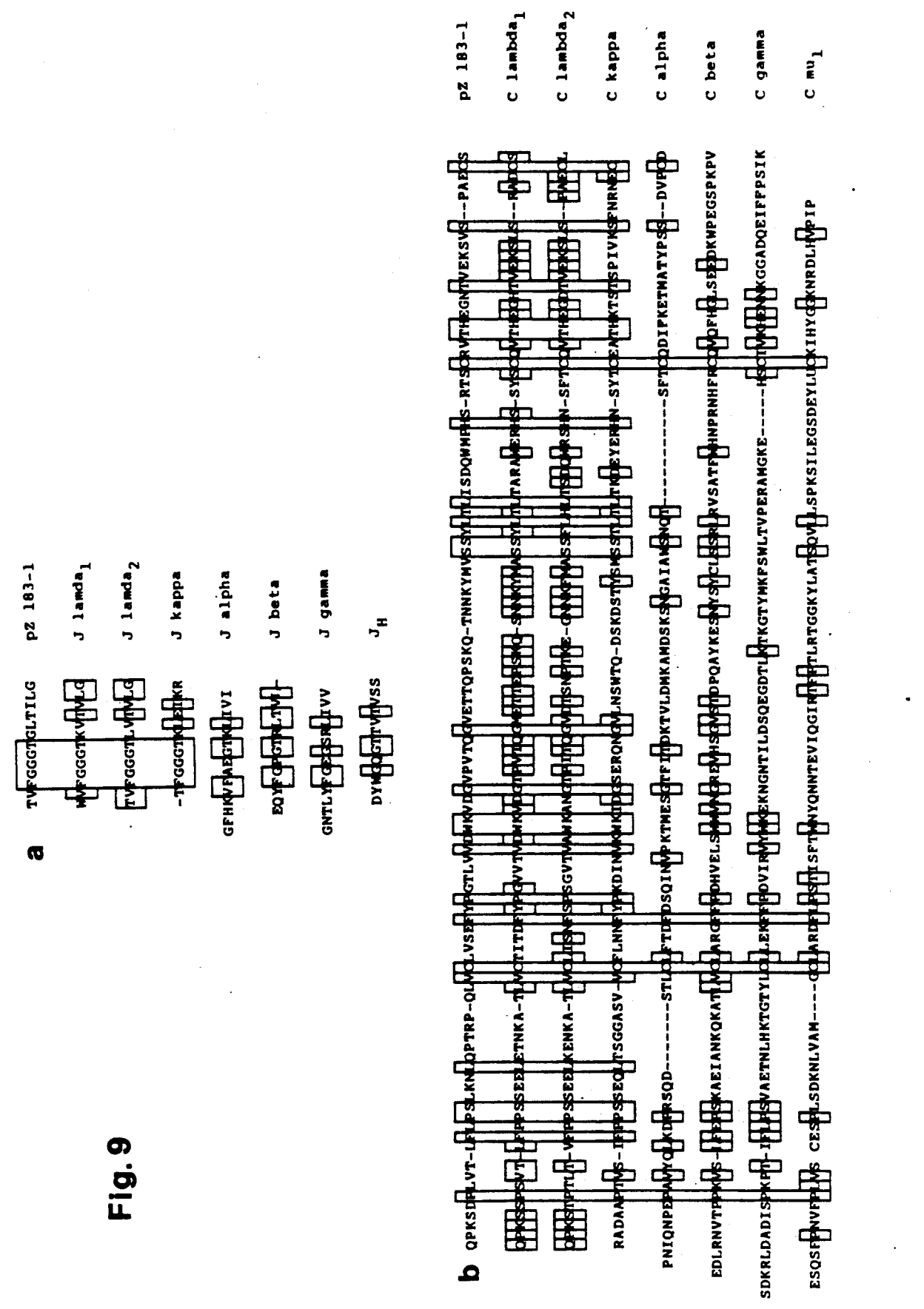

The amino acid sequence of the J-like and C-like regions of the pZ 183-1 gene deduced from reading frame 1 is shown in FIG. 9 and compared to corresponding sequences of Ig and T cell receptor proteins. The strongest homology, again, is detectable with the J-segment and the C domain of λ₁ L chains (Table II).

TABLE II

Homologies of pZ 183-1 Sequences With Immunoglobulin Light Chain Genes and Proteins

| Sequence position of pZ 183-1 | L-chain | Literature Reference | Homology with nucleotide sequence* | deduced amino acid sequence+ |
|---|---|---|---|---|
| 240 to 554 | Cλ₁ | (a, d) | 77.9% | 66.7% |
| | Cλ₂ | (a, d) | 70.2% | 61.1% |
| | Cλ₃ | (b, d) | 70.9% | 61.1% |
| | Cλ₄ | (b) | 73.5% | — |
| | Cχ | (c, d) | 22.5% | 30.8% |
| 201 to 239 | Jλ₁ | (a, d) | 67.5% | 66.0% |
| | Jλ₂ | (a, d) | 70.2% | 75.0% |
| | Jλ₃ | (b, d) | 67.6% | 50.0% |
| | Jλ₄ | (b) | 70.2% | — |
| | J₁χ | (c, d) | 59.4% | 58.0% |

*Nucleotide sequence comparisons were done by a computer program and are shown as percent matches per length.
+Alignment of the deduced amino acid sequence of pZ 183-1 with mouse λ₁, λ₂, λ₃, and λ₄ L chains, as well as with κ L was done in order to maximize identities and structure homologies with pZ 183-1, with attention paid to the alignment of certain key conserved residues.
Reference:
a) Bothwell, et al., supra
b) Selsing, et al., Proc. Natl. Acad. Sci. USA 79, 4681–4685, [1982]
c) Hamlyn, et al., Cell 15, 1067–1075, [1978]
d) Kabat, et al., supra.

Furthermore, pZ 183-1 shows cysteine residues at the consensus positions characteristic of all Ig domains, and has the consensus sequence WVFGGGTKVTVLG characteristic of J-segments of the Ig genes. These results suggest that the 3' portion of the pZ 183-1 cDNA clone belongs to a λ L chain-related gene locus called λ₅ (Jλ₅, Cλ₅).

In contrast, the 5' sequence adjacent to the Jλ₁-like sequence of pZ 183-1 does not show strong homology to Vλ₁, to any other known V-segment, or to any other gene known to us. It does not contain a cysteine at the position where a consensus cysteine residue would be expected in V-region domains of Ig. The 5' sequence adjacent to the J-like sequence of pZ 183-1 also does not show any detectable homologies to intron nucleotide sequences either 5' of Jλ₁ or 3' of Vλ₁.

Southern Blot Analyses of DNA from 70Z/3 Cells. (FIG. 10)

DNA was digested with the restriction enzyme HindIII, electrophoresed through a 1.0% agarose gel, blotted onto a nitrocellulose filter and hybridized with the $^{32}$P-labelled insert of the clone pZ 183-1 (lane 1). Hybridization was carried out at 42° in 50% formamide and 5xSSC. The filters were washed at 65° C. in 0.2×SSC. After exposure to X-ray film, the same filter was washed in distilled water containing 0.1% SDS at 95° C. for 10 minutes and repeatedly used to probe with Cλ₁ (XhoI-PstI fragment of pAB 1-1, Bothwell et al. supra) (lane 2). both pZ 183-1 and Cλ₁ (lane 3), and Cλ₂ (450 bp SacI fragment of Weiss, et al., Eur. J. Immunol. 15, 765–768, [1985]) (lane 4) successively.

FIG. 10, lane 1 shows that the pZ 183-1 gene is carried in the genome of 70Z/3 cells in a HindIII fragment of over 9.2 kb. Furthermore the Southern blot analysis shows that it is different in context from Cλ₁ (FIG. 10, lane 2) and Cλ₂ (FIG. 10, lane 4). The unknown 5' sequences as well as the Jλ₁- and Cλ₁-like 3' sequences of pZ 183-1 appear to be on the Pst 1-fragment of 4.5 kb. It is on one PstI/BamHI, and on one PstI/HindIII genomic fragment, each 4.2 kb in length. Double digestion with PstI and EcoRI yields two fragments of 1.3 and 2.0 kb (FIG. 11). No differences in the lengths of restriction enzyme fragments of DNA from liver (germ line) and from 70Z/3 cells (pre-B cell) are detectable (FIG. 11). This indicates that the 5' and 3' regions of the pZ 183-1 gene are near to each other, i.e., on one 4.2 kb fragment in germ line DNA.

Construction of Clone pZ 183-1a

From the above results it was clear that the clone pZ 183-1 did not correspond to the full-length 1.2 kb long transcript which is selectively expressed in pre-B cells. Therefore a cDNA library was constructed from poly A containing RNA of the uninduced murine pre-B lymphoma cell line 70Z/3 by the method described by Okayama et al. (Mol. Cell. Biol. 2, 161–170, [1982]). $5 \times 10^4$ individual recombinant clones were screened with the radioactive insert of pZ 183-1 as described above.

Nine positive clones were identified. After restriction map analysis one clone was chosen which appeared to have the longest insert. This insert was cloned into the PstI site of the polylinker of pUC13 (Messing, et al., supra). The plasmid pZ 183-1a obtained was transfected into E. coli DH1 (ATCC No. 33849). The resulting DH1 (pZ 183-1a) was deposited on Nov. 20, 1986 at the Deutsche Sammlung von Mikroorganismen (DSM) its accession number being DSM 3902. DNA sequencing was carried out by the dideoxy chain termination method by subcloning the fragments indicated in FIG. 12 into M13 mp18 and M13 mp19 vectors (Messing, et al., supra; also commercially available at New England Biolabs, Beverly Mass., U.S.A. under catalogue No. 408 and at GIBCO BRL GmbH, Eggenstein, West Germany, catalogue Nos. 520-8227 SA and 520-8229 SA), using a 17-mer universal M13 primer (Amersham). Plasmid pZ 183-1a comprises the nucleotide sequence selectively expressed in pre-B cells which is shown on page 4.

Isolation and Characterization of λ5 Genomic Clones

DNA from the 70Z/3 murine pre-B lymphoma, partially digested with MboI to an average size of 20 kb, was used to construct a genomic phage library in the vector EMBL-3 (Frischauf, et al., J. Mol. Biol. 170, 827–842, [1983]: Uematsu, et al., EMBO J. 5, 2123–2129, [1986]). The genomic library was screened successively with three kinds of $^{32}$P-labelled probes: with 5'-side cDNA (260 bp L. HindIII/StuI fragment of pZ 183-1a insert), 3'-side cDNA (150 bp PvuII/EcoRI fragment of pZ 183), and Cλ₁ (420 bp XhoI/PstI fragment of pAB-1-1, Bothwell, e al., supra).

After hybridization, filters were washed under two stringencies, in an attempt to avoid cross hybridization between λ1 and λ5. Condition 1: 1×SSC, 0.1% SDS at 65° C., condition 2: 0.2×SSC, 0.1% SDS at 65° C. After screening of one million recombinant clones, four independent clones. 7pB5, 7pB12, 7pB18, and 7pB28 were found to be strongly positive in hybridization with both the 5'-probe as well as the 3'-probe of pZ 183. They were further examined by restriction map analysis. The PstI fragment of clone 7pB12 was subcloned into the PstI site of pUC-18 (Messing et al., supra; Gibco BRL catalogue No. 520-5363 SA) and the resulting subclone 7pB12-1 was analyzed by restriction enzyme mapping (FIG. 13).

DNA sequencing was performed by the dideoxy chain termination method (Sanger, et al., supra) using M13 mp18 and M13 mp19 vectors with a 17-mer universal M13 primer and 17–18mer synthesized oligonucleotides (Messing et al., supra). The fragments sequenced are indicated by arrows in FIG. 13.

FIG. 14 shows partial nucleotide sequence of the genomic form of $\lambda 5$. Altogether 2.1 kb of DNA sequences were determined within a stretch of 3.75 kb. Comparison of these genomic sequences to the cDNA sequence of pZ 183-1a shows that $\lambda 5$ is encoded by three exons (boxed in FIG. 14). Exon I, 323 bp long is separated from Exon II, 116 bp in length by an intron of approximately 1.2 kb. Exon II is separated from exon III, 465 bp in size, by an intron of approximately 1.35 kb. No difference was found between the nucleotide sequence of the pZ 183-1a cDNA clone and the corresponding portion of the gene.

The exon-intron boundaries are characterized by splice signal sequences corresponding to the consensus sequences described by Breathnach, et al., (Ann. Rev. Biochem. 50, 349–383, [1981]). It thus appears that the $\lambda 5$ gene codes for a protein with 209 amino acids including a 30 amino acid-long signal peptide which are shown in FIG. 14 in the one letter code described by Dayhoff et al., ("Atlas of Protein Sequence and Structure", M.O. Dayhoff, ed., Vol. 5, p. 17, Natl. Biomed. Res. Found., Silver Spring, Md. U.S.A., [1979]).

The Structure of Exon III and Its Surrounding Introns

Exon III represents the portion of the $\lambda 5$ cDNA that has been shown to be highly homologous to $C\lambda_1$, $C\lambda_2$, $C\lambda_3$ and $C\lambda_4$ (Selsing, et al., supra). Moreover the intron sequences adjacent to the 5' end of exon III are highly homologous to the 5' flanking intron sequences of $C\lambda_2$. Sequences 3' of the coding region of exon III show strong homologies to sequences 3' of the coding region of the exons for $C\lambda_2$ and $C\lambda_3$ (FIG. 15). This shows that this entire region of the $\lambda 5$ gene is closely related to $\lambda$L-chain constant regions.

The Structure of Exon II and Its Surrounding Introns

Exon II is separated from exon III by an intron of approximately 1.35 kb in length, a distance very similar to that observed between $C\lambda_{1,2,3\,or\,4}$ and $J\lambda_{1,2,3\,or\,4}$ gene segments (Miller, et al., Nature 295, 428–430, [1982]; Blomberg, et al., Proc. Natl. Acad. Sci. USA 79, 530–533, [1982]). The 39 nucleotides at the 3' end of exon II show strong homology to $J\lambda_1$, $J\lambda_2$ and $J\lambda_3$ exons (Miller et al., supra). Intron sequences 3' of exon II show strong homologies to the corresponding intron sequences 3' of the exons encoding $J\lambda_2$ and $J\lambda_3$ (FIG. 15 and Table III).

In contrast to classical J segments of Ig genes, and, therefore, also of $\lambda_L$ chains, however, exon II extends its coding region at the 5' end for another 78 nucleotides. This coding sequence within exon II of $\lambda 5$ shows partially strong, partially weak homologies to corresponding intron sequences 5' or the exons of $J\lambda_2$ and $J\lambda_3$ (strong at positions 418–449, and weak at position 395–417 and 449–472). At the 5' end of exon II, in the intron adjacent 5' to this exon and for the rest of the 5' region of the genomic structure of $\lambda 5$ no further homologies can be detected to $\lambda$L-chain sequences (FIG. 15 and Table III).

TABLE III

Homologies of $\lambda 5$ Genomic Sequences With Genomic $\lambda$L-chain Sequences
In detail the following homologies were found (for numbering of positions see FIG. 14)

| 7pB12 - area of Exon II | |
|---|---|
| position 340 to 394: | 33% to $J\lambda 2$ |
| position 395 to 418: | 38% to $J\lambda 2$ |
| position 419 to 449: | 84% to $J\lambda 2$ |
| position 450 to 472: | 38% to $J\lambda 2$ |
| position 473 to 510 (J-like Part of Exon II): | 74% to $J\lambda 1$; 79% to $J\lambda 2$, 72% to $J\lambda 3$; 62% to $J\lambda 4$, |
| position 511 to 527: | 44% to $J\lambda 1$; 65% to $J\lambda 2$, 76% to $J\lambda 3$; 44% to $J\lambda 4$, |
| 7pB12 - area of Exon III | |
| position 233 to 258: | 38% to $C\lambda 1$; 58% to $C\lambda 2$, 46% to $C\lambda 3$; 35% to $C\lambda 4$, |
| position 259 to 578 (coding region of Exon III): | 78% to $C\lambda 1$; 70% to $C\lambda 2$, 71% to $C\lambda 3$; 74% to $C\lambda 4$, |
| position 579 to 608: | 50% to $C\lambda 1$; 53% to $C\lambda 2$, 53% to $C\lambda 3$; 43% to $C\lambda 4$, |

The Structure of Exon I and its Flanking Regions

Exon I does not have strong sequence homologies to the corresponding 5' sequences of $\lambda_L$ chains. i.e. to $V\lambda$ sequences. Sequences comparisons of exon I to other known sequences detected only short but significant homologies to leader sequences of T cell receptor $\lambda$ chains, between positions 458 and 483. Nucleotide sequence homologies were also detectable to parts of known variable regions of Ig genes, i.e., to framework 1 of $V_{H11}$ (FIG. 16). Exon I contains an ATG as potential initiation site for protein synthesis at positions 407 to 409. The deduced amino acid sequence in FIG. 14 shows an amino terminal signal peptide sequence which could be cleaved by a signal peptidase either at the consensus sequence V D G (nucleotide positions 488–496 in exon I) or I L S (nucleotide positions 506–514 in exon I) (Perlman, et al., supra).

Transcription Initiation in pre-B Cells

The 5' end of mature $\lambda 5$ mRNA in pre-B cells was determined by primer extension. A synthetic oligonucleotide 5'-CAGAGTCTGTCCTACTCT-3' complementary to a part of Exon I was labeled with $\gamma$-$^{32}$P ATP using T4 polynucleotide kinase (Ingraham. et al., Mol. Cell. Biol. 6, 2923–2931, [1986]). Poly A containing RNA of the murine pre-B cell line 40E-1 was purified as described above. 500 ng of labeled oligonucleotides were annealed to either 10 $\mu$g of 40E-1 poly A containing RNA or yeast transfer RNA in 50 mM Tris/HCl, pH 7.5, 75 mM KCl, 3 mM MgCl. Cloned Moloney murine leukemia virus reverse transcriptase (600 units) (Bethesda Research Laboratories) was added to each mixture and the reaction was carried out for 1 hour at 37° C. in the presence of 0.5 mM dATP, dGTP, dCTP and dTTP, 10 mM dithiothreitol, 1 mg/ml BSA, 1000 U/ml of ribonuclease inhibitor (Stehelin, Basle) and 100 $\mu$g/ml of actinomycin D.

After the termination of the reaction with EDTA (50 mM), the extended products were precipitated with ethanol. To precisely localize the cap site with respect to the genomic sequences, samples of primer extension reactions were analysed on 6% polyacrylamide DNA sequencing gels in parallel with sequencing reactions (FIG. 17). Two major sites of termination of extension were found. Site a (see FIG. 17) occurs at an A nucleotide and is, thus, the most likely site of transcription initiation and CAP formation (Breathnach, et al., supra).

Isolation of Human cDNA Homologous to Mouse cDNA pZ 183-1a

A human fetal liver cDNA library in the vector λgt11 was obtained from Clontech Laboratories, Inc. (4055 Fabian Way, Palo Alto, Calif. 94303, USA—Catalog #HL 1005). $2.5 \times 10^6$ recombinant phage clones were plated onto agar plates (Maniatis, et al., pp. 68–73) containing 25 µg/ml ampicillin and were transferred to nitrocellulose filters as described (Benton. et al., supra). The filters were screened with a $^{32}$P-labelled 700 nucleotide pair fragment generated by cutting the plasmid pZ 183-1a with PvuII and HindIII (=mouse probe). Following digestion, the insert was separated by electrophoresis through a 1% low melting point agarose gel and radiolabeled with $^{32}$P-dATP by the Klenow fragment reaction with random hexanucleotide primers from calf thymus DNA (Feinberg, et al., supra). Prehybridization of the filters was done at 37° C. in a solution containing 50% formamide, 5×SSPE, 0.1% SDS, 10× Denhardt's solution. 100 µg/ml salmon sperm DNA, 1 µg/ml E.coli RNA, and 1 µg/ml poly(A). Hybridization of the filters was done in the same conditions with the addition of $1 \times 10^6$ cpm/ml of $^{32}$P-labeled mouse probe.

To detect human cDNAs cross-hybridizing with the mouse probe, the filters were exposed to autoradiographic film following each of a series of increasingly stringent washes. The washes each contained 2×SSC, 0,1% SDS and were done with three 20 minute rinses at the following temperatures: 22° C. (wash 1), 45° C. (wash 2) and 65° C. (wash 3). 15 primary clones were picked which were positive following the 65° C. wash. After a second round of plating and screening of the 15 primary clones, 6 secondary clones were individually grown up and DNA was extracted by the method of Yamamoto et al. (supra).

The DNA was cut with EcoRI and separated by electrophoresis through a 1% agarose gel, blotted onto nitrocellulose filter and hybridized with probes specific for the 5' or 3' regions of pZ 183-1a. Plasmid subclones in pUC13 (pHFL-1) or pUC18 (pHFL-2) were prepared by isolating the EcoRI inserts of λgtII clones HFL-1 and HFL-2 from 1% low melting point agarose gels and ligating the inserts into the EcoRI sites of the pUC vectors. Restriction map analysis and DNA sequence analysis are used to characterize the cloned DNA sequence. RNA dot blots and Northern blots are used to show the selective expression of this sequence in human pre-B cells.

In a search for possible noncoding exons upstream of λ5 with functions in the regulation of expression of this gene, total RNA preparations of 70Z/3 pre-B lymphoma cells (λ5+) and of EL4 thymic lymphoma cells (λ5−) were probed by Northern blot analysis with different radiolabelled segments of the 7pB12 genomic clone containing the λ5 gene plus 10 kb upstream of it. The subclone 7pB12-2 containing a BamHI-XbaI fragment of the 5' region of 7pB12 (FIG. 18) was found to hybridize to 70Z/3, but not to EL4 total RNA (FIG. 19). The size of the hybridizing RNAs, however, was not that of λ5 mRNA. i.e., not 1.2 kb but 0.85 kb. Therefore a cDNA clone which would hybridize with this BamHI-XbaI fragment of the genomic 7pB12 clone was searched.

In a library of $10^6$ once amplified cDNA clones constructed from 70Z/3 pre-B lymphoma poly A+ RNA around 100 positive clones were found. One out of seven strongly hybridizing clones found was selected because it appeared to have the longest insert. This clone, named pZ121 (FIG. 20), contains a 780 base pair long pre-B specific insert including 20 base pairs of poly A. The clone pZ121 was deposited on Apr. 23, 1987 at the Deutsche Sammlung von Mikroorganismen (DSM) in the form of a sample of E. coli DHI (pZ121), its accession number being DSM 4088.

The expression of the gene corresponding to pZ 121 was probed with RNA from a variety of cell lines by Northern dot blot analysis (FIG. 21). It was found to be expressed in Abelson virus-transformed cell lines of day 13–14 (40E-1), day 17–18 of gestation in fetal liver (28C-9, B3-P8-16-11-1), and of adult bone marrow (220-8, 204-1-8, 230-238, 204-3-1, 18-81), and in 70Z/3 pre-B cells from where the gene has been isolated. It is not expressed in mature Ig positive B cells (WEHI-279, WEHI-231, A 20-3, 2PK-3). in plasma cells (SP2/0, MPC-11), in T cells (EL4, BW5147, K62). and in macrophages (WEHI-3, P338DI) and Ltk$^-$ cells. The pattern of expression is indistinguishable from that of the λ5 gene and indicates selective expression in pre-B cells.

The nucleotide sequence of pZ121 Was determined by the strategy outlined in FIG. 20 and is shown in FIG. 22. A DNA sequence data bank (Gen Bank TM, 1986) was searched for possible evolutionary relationships of the pZ121 sequence to known DNA sequences. For positions 477 to 785, homologies were found with sequences encoding murine variable regions $V_\kappa$ and $V_\lambda$ of L chains. This nucleotide sequence shows 48% homology to the corresponding sequence of $V_{\lambda 1}$, and 46% to $V_{\kappa 21}$ (43% to framework [FR] II of λ1, 57% to FR II of $V_{\kappa 21}$, 56% to FR III of $V_{\lambda 1}$, and 53% to FR III of $V_{\kappa 21}$).

The longest open reading frame of the pZ121 cDNA codes for a protein of 142 amino acids, including a 19 amino acid long leader sequence at its amino terminus (FIG. 22). Comparison of the deduced amino acid, sequence of pZ121 with the published sequences of $V_{\kappa 21}$ (Fong, et al., Biochem. Biophys. Res. Commun. 90, 832–841, [1979]), (Hamlyn, et al., Nucleic Acids Res. 9, 4485–4494, [1981]), $V_{\lambda 1}$ and $V_{\lambda 2}$ (Tonegawa, et al., Proc. Natl. Acad. Sci. USA 75, 1485–1489, [1978]) indicates that consensus cysteine residues as well as other consensus amino acids are conserved in the protein encoded by pZ121 which characterize Ig domains (Amzel, et al., Ann. Rev. Biochem. 48, 961–997, [1979]) (FIG. 23). The homologies of pZ121 to $V_{\kappa 21}$, $V_{\lambda 1}$ and $V_{\lambda 2}$ are in the same ranges as those between $V_\kappa$ and $V_\lambda$.

The amino acid sequence of $V_{preB1}$ between position +1 and +103 shows 31% homology to the corresponding sequence of $V_{\lambda 1}$, and 34% to $V_{\kappa 21}$, in an area where $V_{\lambda 1}$ and $V_{\kappa 21}$ are 39% homologous. With $V_\kappa$, $V_\lambda$ and $V_H$pZ121, therefore, detects a gene which constitutes a fourth locus of V-related sequences which was called $V_{preB}$1 and which is 4.6 kb upstream from the λ5 gene.

The evolutionary relationship of $V_{preB}$1 to Ig V-gene segments is further born out by its genomic organization. For the determination of this genomic organization, the BamHI-XbaI fragment of the 7pB12 genomic clone was subcloned and sequenced as outlined in FIG. 18. The sequence is given in FIG. 23. It shows that $V_{preB}1$ is composed of two exons. Exon 1 codes for most of the leader peptide and is separated from exon II by 87 bp.

Sequences 5' of the first exon of $V_{preB}1$ do not contain a TATA box as many Ig-V-gene segments do, nor an octamer consensus sequence (Parslow et al., Proc. Natl. Acad. Sci. USA 81, 2650-2654 [1984]) which is commonly found at 5' ends of $V_L$ and $V_H$ genes of mouse and man. This is reminiscent of a similar lack of such sequences 5' of the $\lambda_5$ gene and may indicate that different transcription regulating DNA sequences may be operative for pre-B cell specific expression of $V_{preB}1$ and $\lambda_5$. In fact, no homologies were detectable to any known nucleotide sequences.

The nucleotide sequences encoding the leader peptide show homology to those encoding $\lambda_1$ and $\lambda_2$ L chain leader peptides, but not to those encoding the $\kappa$L chain leader peptide in $V_\kappa 21$ (FIGS. 23 and 24). However, sequences of $V_{preB}1$ corresponding to the V segment of L chain genes shown almost equal homologies to those sequences encoding the V gene segment part of $\lambda$ as well as $\kappa V$ regions of L chains. The V-like sequences in the $V_{preB}1$ gene are followed by sequences from position 768 to the end at position 1053 (FIG. 23) where no homology to any known nucleotide sequence could be detected.

$V_{preB}1$ protein can associate with itself, with $V_H$ domains expressed in pre B cells or even with $\lambda_5$ proteins. In this case $V_{preB}1$ and $\lambda_5$ proteins may form a complete V domain via noncovalent bonds which normally hold V gene segment-encoded amino acid in the three dimensional structure of a V domain together with J-gene segment encoded amino acids (Amzel. et al., supra). The amino terminal 62 amino acids of $\lambda_5$ and the carboxy terminal 26 amino acids of $V_{preB}1$ become in this case localized as a large protrusion at the CDR3 site. Together with the unusual extra 4 amino acids found in CDR 2 and two extra ones within FR 3 (FIG. 23) $V_{preB}1$, in association with $\lambda_5$, constitutes an Ig domain with unusual, constant binding properties having some function in the regulation of pre-B cell development.

No recombination heptamer and nonamer signal sequences (Sakano et al., Nature, 280, 288-294 [1979]) can be found at the 3' end of $V_{preB}1$ gene. It is therefore unlikely that $V_{preB}1$ can eve rearranged as a V gene segment in the way that the Ig and T cell receptor gene loci do.

Southern Blot Analysis Detects Two $V_{preB}$ Genes

Southern blot analysis was carried out with liver DNA from DBA/2 and C57BL/6 mice, and with DNA from the mouse pre-B cell line 70Z/3, generated in C57BL/6×DBA/2 $F_1$ mice. High molecular weight DNAs were digested with five restriction enzymes, EcoRI, BamHI, HindIII, PstI or KpnI, and the fragments were separated by gel electrophoresis and probed with the $V_{preB}1$ cDNA clone pZ 121. The hybridization pattern shown in FIG. 24 indicates that two bands were detectable in EcoRI, BamHI and HindIII digested DNAs from the three sources, while three and four bands were seen with KpnI and PstI digested DNAs. Multiple hybridizing bands with all five enzymes indicated that there were multiple $V_{preB}$ genes in the mouse genome and prompted a structural analysis of the difference of the two genomic DNA fragments.

When DNA of the genomic clone 7pB12 containing the $\lambda_5$ associated $V_{preB}1$ gene was digested with either KpnI or PstI and probed in Southern blots with pZ 121, it was found to contain the first and the last of the three or four bands seen in FIG. 24. We conclude that the middle band of KpnI, and the middle two bands of PstI digestions seen in FIG. 24 must contain the other $V_{preB}$ gene, which we call $V_{preB}2$. It should be noted that the band with the smallest molecular weight of both KpnI as well as PstI digestions seen in FIG. 24, in fact, contains sequences of both $V_{preB}1$ and $V_{preB}2$ genes, as analyses with the appropriate genomic clones (see below) have shown. No differences in the lengths of restriction fragments of DNA from liver and from 70Z/3 cell lines have been detected for $V_{preB}1$ as well as $V_{preB}2$. This indicates that $V_{preB}1$ and $V_{preB}2$ genes are not rearranged during pre B-cell development.

Isolation and Characterization of the $V_{preB}2$ Gene

A genomic library was constructed from DNA of the pre-B cell line 70Z/3, which was partially digested with MboI to an average size of 20kb, using the EMBL-3 vector (Frischauf et al., supra). The genomic library was screened with a $^{32}$P-labelled pZ 121 probe. Prehybridization and hybridization were carried out with 50% formamide at 42° C. (Maniatis et al., supra). Filters were finally washed with 0.2×SSC, 0.1% SDS at 65° C. After screening of one million recombinant amplified clones, six independent clones were found and further examined by restriction map analysis. DNAs of possible clones were then digested with PstI and KpnI and probed in Southern blots with pZ 121. Two clones 7pB60 and 7pB70 contained the appropriate bands i.e., the $V_{preB}2$ gene.

The 4.4 kb BglII-BamHI fragment of 7pB70 was subcloned into BamHI site of pUC18 and was analyzed by restriction enzyme mapping (FIG. 25) and DNA sequencing (FIG. 22). Comparison to $V_{preB}1$ indicates that $V_{preB}2$ has a 97% nucleotide homology to $V_{preB}1$ in an area of 1 kb which covers the cDNA coding region of $V_{preB}1$.

More specifically $V_{preB}2$ differs in the nucleotide sequence of the coding exons from $V_{preB}1$ in nine bases, five of which constitute replacement mutations within the presumed amino acid sequences of the two $V_{preB}$ genes. The two $V_{preB}$ genes are apparently preserved as two copies in many laboratory strains of mice, in wild mice and in other closely related rodents such as hamsters, rats and guinea pigs. $V_{preB}2$ has not yet been linked at the molecular level to $V_{preB}1$ and $\lambda_5$, nor have any of them been linked to any other known genes such as those encoding the $\lambda$L chains. All three genes are located on chromosome 16 of the mouse, which also harbors and $\lambda$L chain genes (D'Eustachio et al., J. Exp. Med. 153, 793-900, [1981]).

In a little more than the 10 kb of DNA on chromosome 16 in which $V_{preB}1$ and $\lambda_5$ are located, five areas of DNA sequences can be discerned which appear to have evolved in quite separate ways. $V_{preB}1$ and $\lambda_5$ are flanked at the 5' and 3' end by sequences with no homologies to known DNA sequences. The exon encoding the leader sequence of $V_{preB}1$ as well as the intron between this leader and the second exon of $V_{preB}1$ has strong homology to corresponding gene segments of V gene segments of $\lambda$L chain genes (Tonegawa, et al., Proc. Natl. Acad. Sci. USA 75, 1485-1489, [1978]). $V_{preB}1$ (and $V_{preB}2$) has a much lower degree of homology to $V\lambda$, a homology which is equally high to $V_K$ segments. This is followed by a third area encoding the 3' end of V$_{preB}$1, the intervening non coding sequences between V$_{preB}$1 and λ5 as well as the 5' located first exon of the λ5 gene which shows no homology to any known sequence This area of sequence may well have evolved by an insertion into a preexisting V (V$_{preB}$1) and C (λ5). The fourth area of DNA, exon II exon III and the intervening intron of λ5 gene, shows again strong homology to λL chain genes, as do the leader sequence of V$_{preB}$1. The difference in homologies within the V segments of V$_{preB}$1 (and V$_{preB}$2) indicates that this area of the two genes may have been selected for functions which differ from those of λL chain V regions. The λ5-encoded protein is a potential candidate for heterodimer formation with H chains in pre-B cells therefore, the V$_{preB}$1 (and V$_{preB}$2) encoded proteins could well associate itself with H chains through the noncovalent association with λ5.

Detection of DNA Sequences with Homologies to the Mouse VpreB Genes in Many Mammalian Species A Southern blot survey of DNA from several species was conducted to determine if sequences homologous to the mouse V$_{preB}$ genes V$_{preB}$1 and V$_{preB}$2 could be detected by cross hybridization at various stringencies. High molecular weight DNAs were extracted from liver of mouse (C57BL/6), rat (Lewis), guinea pig (TRIK, Kleintierfarm Madörin AG, Füllinsdorf CH), rabbit (New Zealand white), hamster (Syrian), and from red blood cells of frog (Xenopus leavis) and from the human myeloid cell line U937 (ATCC No: CRL 1593) (Sundström et al., Int. J. Cancer 17, 565–577 [1976]) and the erythroid line K-562 (ATCC No. CCL 243) (Andersson et al., Int. J. Cancer 23 143–147 [1979]). High molecular weight calf thymus DNA was bought from Pharmacia (Uppsala, Sweden).

After restriction enzyme digestion. 7 μg of DNA fragments were separated by electrophoresis in 0.7% agarose gels in TAE buffer (40 mM Tris/acetate, pH 8.0. 1 mM EDTA) and transferred to nitrocellulose filters (BA85, Schleicher and Schüell) using 20×SSC as transfer buffer. After transfer, filters were baked at 80° C. under vacuum.

Prehybridization and hybridization were done at 65° C. in solutions containing 3×SSC (1×SSC=150 mM NaCl, 15 mM sodium citrate), 10×Denhardt's solution (1×Denhardt's=0.02% mg/ml bovine serum albumin, 0.02% polyvinyl pyrrolidone, 0.02% Ficoll), 0.1% SDS, 100 μg/ml salmon sperm DNA, and 1 mM EDTA. $^{32}$P-labelled (Feinberg and Vogelstein, supra) probes were used at 3×10$^6$ cpm/ml (Cerenkov counts). The 5' EcoRI-AccI 560 bp fragment of V$_{pre-B}$1 contains all but the last 16 bases of the putative amino acid coding region and was isolated from V$_{pre-B}$1 cDNA plasmid clone pZ121. Washing of the filters was done first at room temperature in 2×SSC, 0.1% SDS. For cross species hybridizations, final washes were done with 3 twenty-minute washes in 1×SSC 0.1% SDS at 65° C. Stringent washes were done in 0.2×SSC, 0.1% SDS at 65° C.

FIG. 26 shows the pattern of restriction fragments hybridizing at a stringency calculated to allow 30% mismatched base pairs (Wetmur et al., J. Mol. Biol. 31 349–370 [1968]; Bonner et al., J. Mol. Biol. 81, 123–135 [1973]). Under these conditions DNA from all mammalian species of this survey hybridized to the mouse V$_{pre-B}$1 probe, indicating a widespread conservation of this sequence at a surprisingly high level of homology. At least one hybridizing band was detected in every species. In mice, two V$_{pre-B}$ sequences with greater than 95% homology have been characterized. These sequences are on separate EcoRI fragments, giving rise to the two bands seen with mouse DNA in FIG. 26. These results suggest that sequences with homologies to the mouse V$_{pre-B}$ genes may be conserved in many species.

Isolation of Human Genomic DNA Clones with Sequences Homologous to Mouse V$_{preB}$ Human DNA contained a 15 kb EcoRI fragment that hybridized strongly to the mouse V$_{preB}$1 probe (FIG. 26). To determine the structure of this hybridizing fragment and its similarity to the mouse V$_{preB}$ genes, a phage clone containing this 15 kb EcoRI fragment was isolated from a genomic library constructed from the human myeloid line U937.

DNA from human myeloid line U937 was digested to completion with EcoRI. 10 μg of digested DNA were separated by electrophoresis through 1% low melting point agarose (Bethesda Research Laboratories). DNA fragments ranging from 10 to 15 kb were excised from the gel and purified by organic solvent extractions and ethanol precipitation. Purified, size-fractionated U937 DNA was used to construct a genomic phage library in the vector λgt WES•λB (ATCC No. 37028) (Leder et al., Science 196, 175–177 [1977]).

The partial human genomic library was screened with $^{32}$P-labelled EcoRI-AccI fragment of mouse V$_{preB}$1 cDNA pZ121, under conditions of hybridization and washing used or cross species hybridization of Southern blots described above. Twenty positive clones were picked up in a screen of 3×10$^6$ clones. One of these clones, termed HVPB, was further characterized by plasmid subcloning, restriction mapping and DNA sequencing. Clone HVPB was used to isolate a 2.7 kb HindIII fragment that hybridized strongly to the mouse V$_{preB}$1 cDNA probe. This fragment was inserted into the HindIII site of plasmid pUC18 to derive recombinant plasmid pHVPB-6.

DNA sequencing was performed on M13 mp18 and mp19 subclones of pHVPB-6 by the dideoxy chain termination method (Sanger et al., supra), using a universal M13 17-mer primer.

Structure and Sequence of HVPB and Comparison to Other Genes

FIG. 27 shows the restriction map determined for the genomic phage clone HVPB and the plasmid subclone pHVPB-6. A 2.7 kb HindIII fragment that hybridized strongly to mouse V$_{pre-B}$1 was subcloned in the HindIII site of pUC18. After more detailed restriction enzyme mapping, portions of this plasmid were further subcloned into M13 phage and sequenced according to the strategy shown in FIG. 27. Altogether, 0.5 kb of DNA spanning the regions of strongest homology between human V$_{pre-B}$ and mouse V$_{pre-B}$1 were sequenced.

Alignment of the human and mouse nucleotide sequences revealed an overall homology of 76% (FIG. 27). Striking features of the comparison include the identical length of the putative leader sequences which are encoded by exon I and the 5' 11 bp of exon II, and the similar lengths of intron I and exon II. The exon-intron boundaries contain characteristic splice sequences (Brethnach et al., supra). A split codon 16, with the first nucleotide separated from the second and third by intervening sequence, is present in human V$_{pre-B}$ and is a typical feature of Ig gene family V region leader sequences (Kabat et al., supra).

Particularly noteworthy is the observation that both the mouse and the human sequence diverge from typical V-region sequences at the same position i.e., at the boundary to the CDR3 region of a typical V-gene. Comparison of these divergent sequences again shows high homologies between mouse and man (FIG. 27). The most remarkable feature in the similarities between mouse and human $V_{pre-B}$ are the two stretches of identical nucleotide sequences spanning the whole putative framework 2 (nucleotide positions 250 to 299) and a 3' region of the putative framework 3 (nucleotide positions 399 to 420). This identity in nucleotide sequences is matched by an identity of the putative amino acid sequences (FIG. 27).

A computer search of a sequence data bank (GenBank ™, Genetic Sequence Data Dank. Release 1986) revealed several regions within human $V_{preB}$ homologous to portions of immunoglobulin variable region sequences. Between the putative amino acid residues one and ninety-six, which constitute the mature V-region-like sequences, stretches of human and mouse $V_H$, $V_\kappa$ and $V_\lambda$ sequences showed between 35-50% amino acid homology to human $V_{preB}$. In contrast, mouse $V_{preB}1$ and human $V_{preB}$ are 81% homologous in this region (Table IV).

TABLE IV

| $V_{preB}$ Gene Comparisons: Percent Sequence Homology | | | | |
|---|---|---|---|---|
| | Leader | Intervening Sequence | V-like | non-Ig | Overall |
| Nucleotide | 77 | 60 | 87 | 64 | 76 |
| Amino acid | 74 | — | 81 | 54 | 76 |

Nucleotide residues 400 to 430 showed 94% homology to $V\lambda$ gene 4A, subgroup VII (Anderson et al., Nucleic Acids Res 12, 6647-6661 [1984]), 87% homology to three $V_H$ subgroup II genes ($V_H32$, $V_H52$ and H11; Matthyssens et al. Proc. Natl. Acad. Sci. USA 77, 6561-6565 [1980]; Rechavi et al., Proc. Natl. Acad. Sci. USA 79, 4405-4409 [1982]) and 79% homology to the $V_H$ gene HIGI (Kudo et al., Gene 33, 181-189 [1985]).

Genomic Configuration of Human $V_{preB}$ Gene in Lymphoid Cell Lines

FIG. 28 shows that no rearrangement of the human $V_{preB}$ gene was detected in pre-B cells e.g., line 207 (Findley et al., Blood 60, 1305-1309 [1982]). Nalm-6 (Hurwitz et al. Int. J. Cancer 23, 174-180 [1979]), in the multiple myeloma cell line IM-9 (ATCC No. CCL 159) (De Meyts in "Methods in Receptor Research" Part I, M. Blecher ed, Marcel Dekker, Inc., New York, p. 309 [1976]) and the B lymphoblastoid cell line 1419 (Klobeck, Nature 309, 73-76 [1984]), or in cells from later stages of B cell differentiation, e.g., LBW 4 (Hendershot et al., J. Exp. Med. 156, 1622-1634 [1982], GM607 (Klobeck, supra), in Burkitts lymphoma cell lines, e.g., Raji (ATCC No. CCL 86) (Epstein et al., J. Natl. Cancer Inst. 34, 231-240 [1965]) and Daudi (ATCC No. CCL 213) (Klein et al., Cancer Res. 28, 1300-1310 [1968]) or in the myeloid cell line U937 (Sundström et al., supra), in the erythroid cell line K562 (Anderson et al., supra) and in the T cell line Jurkat (Schneider et al., Int. J. Cancer 19, 621-626 [1977]). All of these samples had only the germline 15 kb EcoRI hybridizing fragment. Therefore, neither mouse nor human $V_{pre-B}$ genes appear to be rearranged during B cell development.

Expression of Human $V_{pre-B}$ in Lymphoid Cell Lines

One of the important characteristics of the mouse $V_{pre-B}1$ gene is its restricted expression in mouse pre-B cell lines and, therefore, the pattern of expression of human $V_{pre-B}$ in human lymphoid lines by Northern blot analysis of poly(A)-selected RNA was examined.

Total RNA was isolated from cytoplasm after lysis of cells in 5% citric acid containing 0.1% NP-40 as described by Schibler et al. (J. Mol. Biol, 142, 93-116 [1980]) and further purified by oligo(dT) cellulose chromatography as described above. 5 µg of poly(A) enriched RNA were electrophoresed through 1% agarose gels containing 18 mM $Na_2HPO_4$, 2 mM $NaH_2PO_4$ and 6% formaldehyde. Separated RNA was then blotted onto diazotized phenylthioether (DPT) paper (Schleicher and Schüell).

Prehybridization of filters was done at 45° C. in solutions containing 5×SSPE (1×SSPE=150 mM NaCl, 10 mM $NaH_2PO_4$, 1 mM EDTA), 5×Denhardt's, 2 mM glycine, 50% deionized formamide, 100 µg/ml salmon sperm DNA, 20 µg/ml yeast tRNA and 1 µg/ml poly(A). Stringent hybridizations were done at 45° C. in prehydridization solution lacking glycine but containing 10% dextran sulfate and 3×10⁶ cpm/ml ³²P-labelled probe. Cross species hybridizations were done at 37° C. in hybridization solution containing only 30% formamide. Stringent washes were done at 65° C. in 0.2×SSC, 0.1% SDS. Cross species hybridization experiments were washed finally in 0.2×SSC, 0.1% SDS at 37° C.

Human $V_{preB}$ is expressed only in pre-B cell lines 207, 697 (Findley et al., supra), Nalm-6 (Hurwitz et al., supra) but not in the cell lines LBW-4, Raji and Jurkat (FIG. 29). The human $V_{preB}$ poly(A)+ mRNA is 0.85 kb in size, as is the mRNA of its mouse homologue, $V_{preB}1$. Under low stringency conditions the mouse $V_{preB}1$ gene also hybridizes to 0.85 kb RNA of human pre-B cell lines (FIG. 29). Similar intensities of hybridization and similar sizes of the RNAs which hybridize with the mouse $V_{preB}1$ probe and the human probe indicate that the same RNA molecules may hybridize to both probes. The upper band in FIG. 29B corresponds to the size of 28S ribosomal RNA and may be the result of crosshybridization of the mouse $V_{preB}1$ probe to human ribosomal RNA at low stringency. The pattern of RNA expression of human $V_{preB}$, so far, follows that of $V_{preB}1$ and λ5 in the mouse and indicates that human $V_{preB}$ is selectively expressed in human pre-B cell lines, but not in mature B cell or T cell lines.

Many modifications and variations of this invention may be made without departing from its spirit and scope, as will become apparent to those skilled in the art. The specific embodiments described herein are offered by way of example only, and the invention is to be limited only by the terms of the appended claims.

What is claimed is:

1. A polynucleotide which has the nucleotide sequence

GAGCTCTGCATGTCTGCACCATGTCCTGGGCT

CCTGTCCTGCTCATGCACTTTGTCTACT

GCACAGGTGAGGGAACCCCCAGATCCCAAAGA

CTCCTGCCCCTTCCTTCATCCTGCCCTG

```
CCCCCACGGGCCACATGCATCTGTGTCACCAG

GTTGTGGTCCTCAGCCGGTGCTACATCA

GCCGCCGGCCATGTCCTCGGCCCTTGGAACCA

CAATCCGCCTCACCTGCACCCTGAGGAA

CGACCATGACATCGGTGTGTACAGCGTCTACT

GGTACCAGCAGAGGCCGGGCCACCCTCC

CAGGTTCCTGCTGAGATATTTCTCACAATCAG
```

```
GGAATAGCTTTTGGCCACCAGAGGA
GGAACAATCCTTTTGCCGGGAGATCTACACTGCAAGTGAGGCTAGAGTTGACTTTGGACT
TGAGGGTCAATGAAGCTCAGAGTAGGACAGACTCTGGGCACTATCCCCAGGCAGTGTGAA
GTTCTCCTCCTGCTGCTGCTGTTGGGTCTAGTGGATGGTGTCCACCACATACTTTCCCCA
AGCTCAGCAGAAAGGAGCAGAGCTGTGGGCCCTGGAGCTTCAGTGGGAAGCAACAGGCCT
AGCCTATGGGCCCTTCCCGGCAGGCTCCTGTTCCAGATCATCCCACGGGGAGCAGGTCCC
AGGTGCTCGCCCCATAGGCTTCCATCTAAGCCCCAGTTTTGGTATGTCTTTGGTGGTGGG
ACCCAGCTCACAATCCTAGGTCAGCCCAAGTCTGACCCCTTGGTCACTCTGTTCCTGCCT
TCCTTAAAGAATCTTCAGCCAACAAGGCCACACGTAGTGTGTTTGGTGAGCGAATTCTAC
CCAGGTACTTTGGTGGTGGACTGGAAGGTAGATGGGGTCCCTGTCACTCAGGGTGTAGAG
ACAACCCAACCCTCCAAACAGACCAACAACAAATACATGGTCAGCAGCTACCTGACACTG
ATATCTGACCAGTGGATGCCTCACAGTAGATACAGCTGCCGGGTCACTCATGAAGGAAAC
ACTGTGGAGAAGAGTGTGTCACCTGCTGAGTGTTCTTAGAGCACAATCCTCCCTGAAGCC
TCAGGGGCCTGGATCTGAAGTGCCAGAAAAAGTTGTTTTTTGTTTTGTTTTTTGTTTTTT
TTCCCATTAACCATCTCACTGTCTTTCCTGTGCCTAATACTCAATAAATATCTTACCACC
AACC.
```

```
ACAAGAGCCAGGGCCCCCAGGTCCCCCC

TCGCTTCTCTGGATCCAAAGATGTGGCCAGGA

ACAGGGGGTATTTGAGCATCTCTGAGCT

GCAGCCTGAGGACGAGGCTATGTATTACTGTG

CTATGGGGGCCCGCAGCTCGGAGAAGGA

GGAGAGGGAGAGGGAGTGGGAGGAAGAAATGG

AACCCACTGCAG.
``` or a homologous or degenerate sequence thereof, or fragments of said polynucleotide, which fragments hybridize to nucleic acid sequences expressed in pre-B cells and not expressed in other types of cells.

2. A replicable microbial vector comprising a polynucleotide having the sequence of the polynucleotide of claim 1, which polynucleotide is capable of selectively hybridizing to RNA selectively expressed in pre-B cells, or fragments of said polynucleotide, which fragments selectively hybridize to RNA selectively expressed in pre-B cells.

3. The replicable microbial vector of claim 2 containing an expression control sequence operatively linked to the polynucleotide.

4. A host organism transformed with a replicable microbial vector comprising a polynucleotide having the sequence of the polynucleotide of claim 1 or a fragment of said polynucleotide, said fragment selectively hybridizing to RNA selectively expressed in pre-B cells, which organism is capable of producing copies of the polynucleotide.

5. A host organism transformed with a replicable microbial vector comprising a polynucleotide having the sequence of the polynucleotide of claim 1, or a fragment of said polynucleotide, said fragment selectively hybridizing to RNA selectively expressed in pre-B cells, operatively linked to an expression control sequence, which organism is capable of producing a polypeptide encoded by the polynucleotide.

6. A polynucleotide which has the nucleotide sequence or a homologous or degenerate sequence thereof, or fragments of said polynucleotide, which fragments hybridize to nucleic acid sequences expressed in pre-B cells and not expressed in other types of cells.

7. A replicable microbial vector comprising a polynucleotide having the sequence of the polynucleotide of claim 6, which polynucleotide is capable of selectively hybridizing to RNA selectively expressed in pre-B cells, or fragments of said polynucleotide, which fragments selectively hybridize to RNA selectively expressed in pre-B cells.

8. The replicable microbial vector of claim 7 containing an expression control sequence operatively linked to the polynucleotide.

9. A host organism transformed with a replicable microbial vector comprising a polynucleotide having the sequence of the polynucleotide of claim 6 or a fragment of said polynucleotide, said fragment selectively hybridizing to RNA selectively expressed in pre-B cells, which organism is capable of producing copies of the polynucleotide.

10. A host organism transformed with a replicable microbial vector comprising a polynucleotide having the sequence of the polynucleotide of claim 6, or a fragment of said polynucleotide, said fragment selectively hybridizing to RNA selectively expressed in pre-B cells, operatively linked to an expression control sequence, which organism is capable of producing a polypeptide encoded by the polynucleotide.

11. A polynucleotide which has the nucleotide sequence

```
CCAGAAAGCCTGGGAGGGTGGTGAGCAGGAACCAGGGGTGCAGTGAC
CCTCTCCCCAAAGCAGGGAGGAGAGTGCTTCCCAGCTGGTCAGGGCCCAGGAGCAGTGGC
TGTAGGGGGCAGGGTGCTGCAGGTCTGGAGCCATGGCCTGGACGTCTGTCCTGCTCATGC
TGCTGGCCTATCTCACAGGTTGTGGCCCTCAGCCCATGGTGCATCAGCCACCATTAGCAT
CTTCTTCCCTTGGAGCCACCATCCGCCTCTCCTGTACCCTGAGCAACGACCATAACATTG
GCATTTACAGCATTTACTGGTACCAGCAGAGGCCGGGCCACCCTCCCAGGTTCCTGCTGA
GATACTTCTCACACTCAGACAAGCACCAGGGTCCCGATATCCCACCTCGCTTCTCCGGGT
CCAAAGATACGACCAGGAACCTGGGGTATCTGAGCATCTCTGAACTGCAGCCTGAGGACG
```

-continued

```
AGGCTGTGTATTACTGTGCCGTGGGGCTCCGGAGCCAGGAAAAGAAGAGGATGGAGAGGG
AGTGGGAAGGAGAAAAGTCGTATACAGATTTGGGATCTTAGGCTCTGGAGACATTCAGAC
CCTGAACTGAAGACAGAGTTTGCTTTGCTCGGCTAGTCTGGTATGGGAAGGAGGGGTAGA
ACGTGAGGTTTTGCAGAGCCTAGAAGATGGAATTATGCAGCTTTTCCTTGTTCTGCGGTG
TTGCTATGAGCCCCCATTGGAGGCTGGATTGTAGAATTAAAGCTGTTTTTACTG.
``` or a homologous or degenerate sequence thereof, or fragments of said polynucleotide, which fragments hybridize to nucleic acid sequences expressed in pre-B cells and not expressed in other types of cells.

12. A replicable microbial vector comprising a polynucleotide having the sequence of the polynucleotide of claim 11, which polynucleotide is capable of selectively hybridizing to RNA selectively expressed in pre-B cells, or fragments of said polynucleotide, which fragments selectively hybridize to RNA selectively expressed in pre-B cells.

13. The replicable microbial vector of claim 12 containing an expression control sequence operatively linked to the polynucleotide.

14. A host organism transformed with a replicable microbial vector comprising a polynucleotide having the sequence of the polynucleotide of claim 11 or a fragment of said polynucleotide, said fragment selectively hybridizing to RNA selectively expressed in pre-B cells, which organism is capable of producing copies of the polynucleotide.

15. A host organism transformed with a replicable microbial vector comprising a polynucleotide having the sequence of the polynucleotide of claim 11, or a fragment of said polynucleotide, said fragment selectively hybridizing to RNA selectively expressed in pre-B cells, operatively linked to an expression control sequence, which organism is capable of producing a polypeptide encoded by the polynucleotide.

* * * * *